United States Patent
Iwasaki et al.

(10) Patent No.: US 11,119,161 B2
(45) Date of Patent: Sep. 14, 2021

(54) MAGNETIC SENSOR AND DIAGNOSTIC DEVICE

(71) Applicant: KABUSHIKI KAISHA TOSHIBA, Tokyo (JP)

(72) Inventors: Hitoshi Iwasaki, Nerima Tokyo (JP); Akira Kikitsu, Yokohama Kanagawa (JP); Yoshihiro Higashi, Komatsu Ishikawa (JP); Satoshi Shirotori, Yokohama Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 16/816,401

(22) Filed: Mar. 12, 2020

(65) Prior Publication Data
US 2021/0080519 A1    Mar. 18, 2021

(30) Foreign Application Priority Data

Sep. 13, 2019  (JP) .............................. JP2019-167630
Mar. 9, 2020   (JP) ................................ 2020-040055

(51) Int. Cl.
*G01R 33/09*   (2006.01)
*G01R 33/00*   (2006.01)

(52) U.S. Cl.
CPC ....... *G01R 33/093* (2013.01); *G01R 33/0094* (2013.01)

(58) Field of Classification Search
CPC ... G01R 33/0094; G01R 33/09; G01R 33/098
See application file for complete search history.

(56) References Cited

U.S. PATENT DOCUMENTS 5,994,898 A * 11/1999 DiMarzio .......... G01R 33/0325
                                                     324/142
2011/0062956 A1* 3/2011 Edelstein ........... G01R 33/0286
                                                     324/251
(Continued)

FOREIGN PATENT DOCUMENTS

JP           2018-155719 A      10/2018

OTHER PUBLICATIONS

Valadeiro et al., "Strategies for pTesla Field Detection Using Magnetoresistive Sensors With a Soft Pinned Sensing Layer," IEEE Transactons on Magnetics, vol. 51, No. 1 (Jan. 2015), 4 pages.

*Primary Examiner* — Alvaro E Fortich
(74) *Attorney, Agent, or Firm* — Finnegan, Henderson, Farabow, Garrett & Dunner L.L.P.

(57) ABSTRACT

According to one embodiment, a magnetic sensor includes a first element. The first element includes a first magnetic part, a first magnetic layer, a first nonmagnetic portion, and a first intermediate magnetic layer. The first magnetic part includes first to third portions. The first portion is between the second and third portions. The first portion has a first length and a second length. The second portion has at least one of a third length longer than the first length or a fourth length longer than the second length. The third portion has at least one of a fifth length longer than the first length or a sixth length longer than the second length. The first nonmagnetic portion is provided between the first portion and the first magnetic layer. The first intermediate magnetic layer is provided between the first portion and the first nonmagnetic portion.

16 Claims, 40 Drawing Sheets

(56) References Cited

U.S. PATENT DOCUMENTS

| | | | |
|---|---|---|---|
| 2017/0178781 A1* | 6/2017 | O'Donnell | H01F 17/0033 |
| 2018/0003776 A1* | 1/2018 | Suess | G01R 33/0011 |
| 2018/0271395 A1 | 9/2018 | Iwasaki et al. | |

* cited by examiner

|  | L4(μm) | L2(μm) | t1(μm) | t2(μm) | t2/t1 | L4/L2 | G |
|---|---|---|---|---|---|---|---|
| MD1 | 2000 | 2000 | 0.02 | 0 | 0 | 1 | 1 |
| MD2 | 2000 | 500 | 0.02 | 0 | 0 | 4 | 1.3 |
| MD3 | 2000 | 20 | 0.02 | 0 | 0 | 100 | 2.6 |
| MD4 | 2000 | 5 | 0.02 | 0 | 0 | 400 | 3.1 |
| MD5 | 2000 | 20 | 0.02 | 0.2 | 10 | 100 | 22 |
| MD6 | 2000 | 20 | 0.02 | 0.5 | 25 | 100 | 56 |
| MD7 | 2000 | 20 | 0.02 | 1 | 50 | 100 | 95 |
| MD8 | 2000 | 20 | 0.05 | 2 | 40 | 100 | 103 |

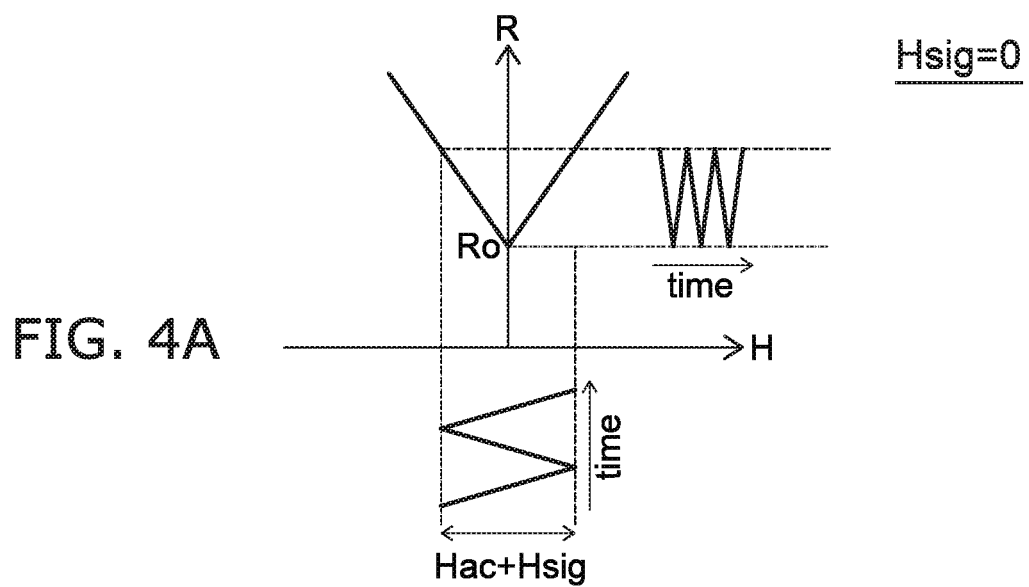
FIG. 4A
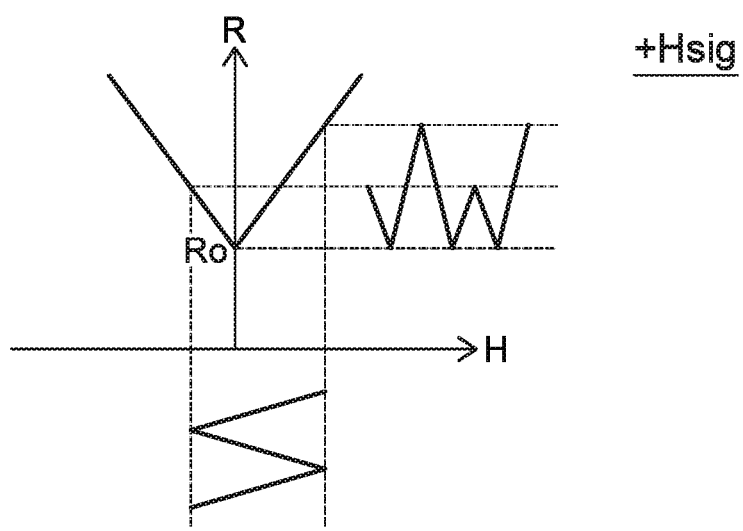
FIG. 4B
FIG. 4C

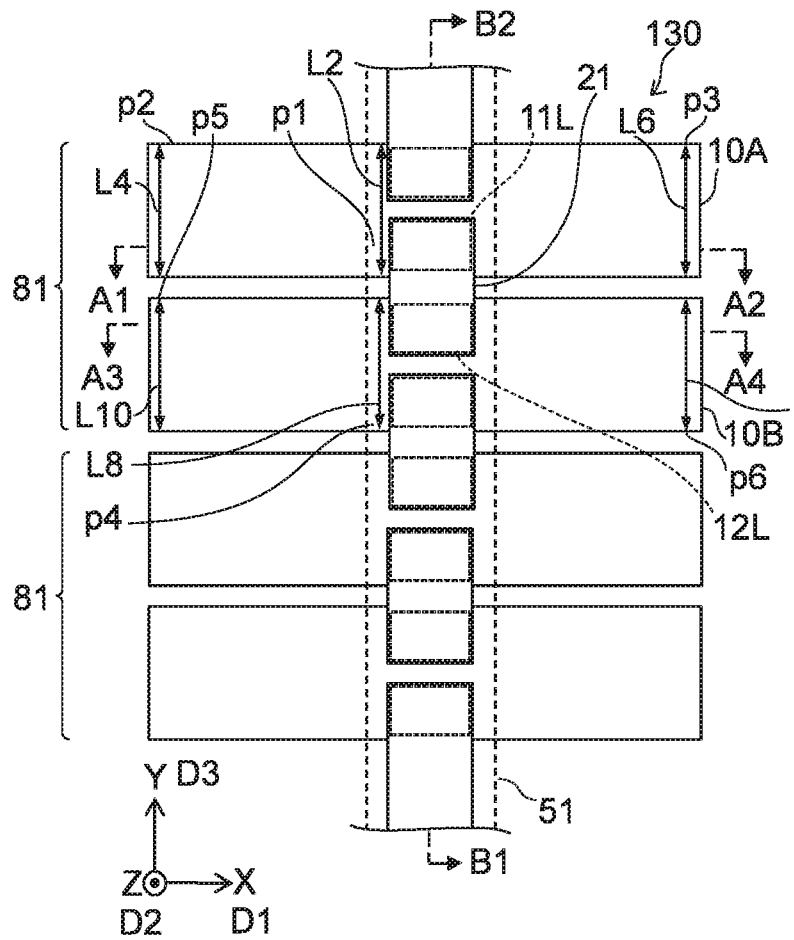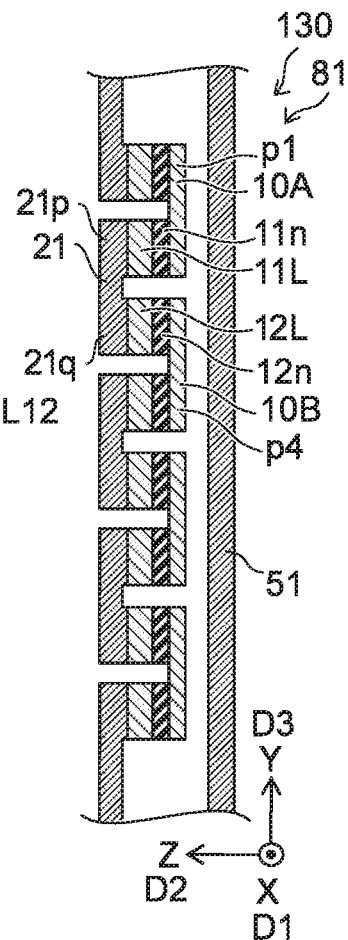
FIG. 29A   FIG. 29B
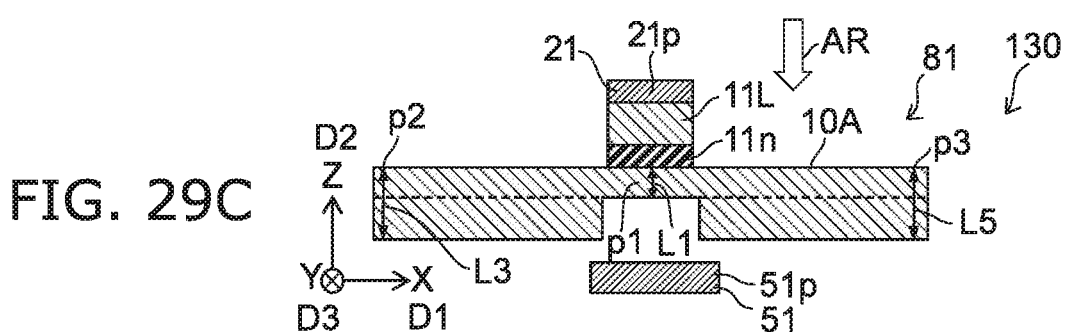
FIG. 29C
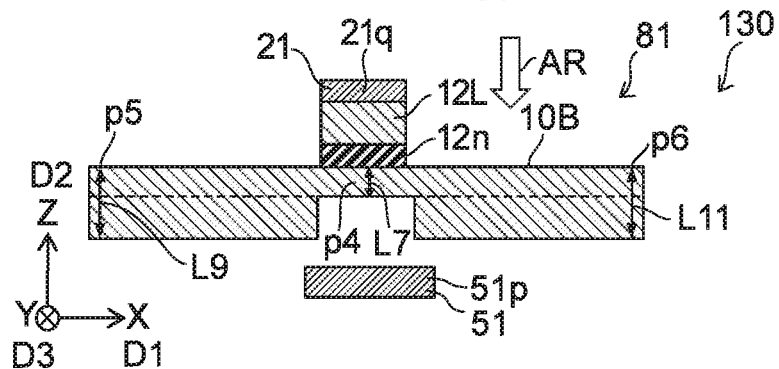
FIG. 29D

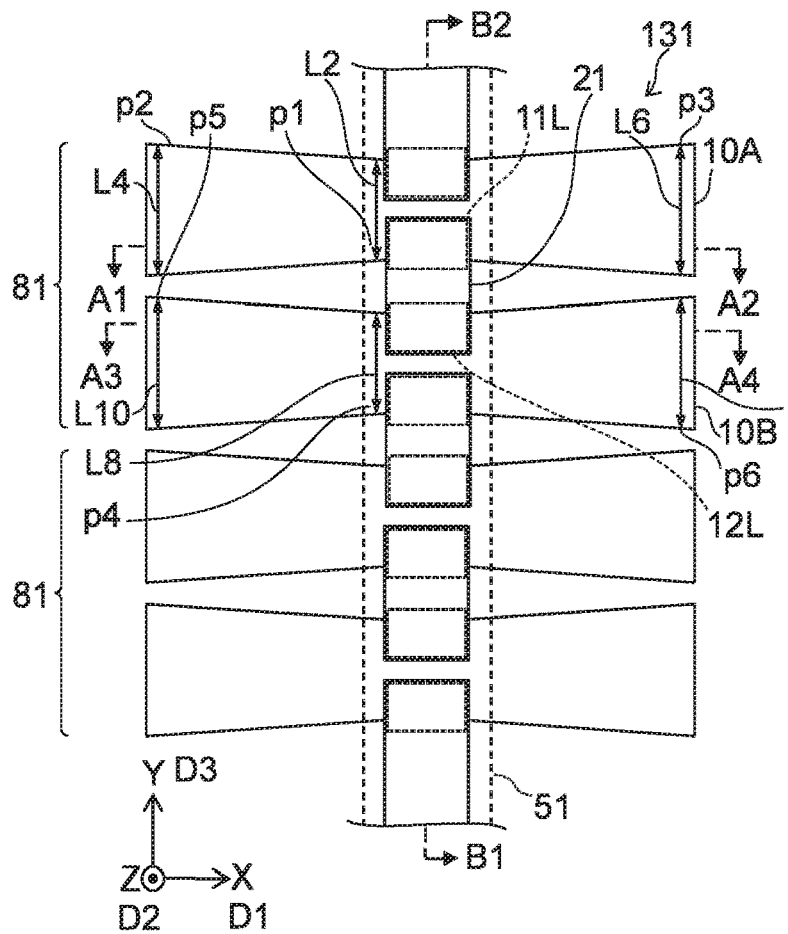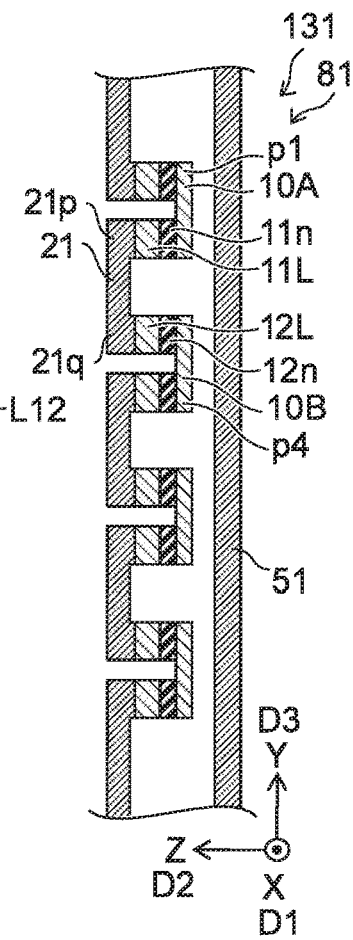
FIG. 30A  FIG. 30B
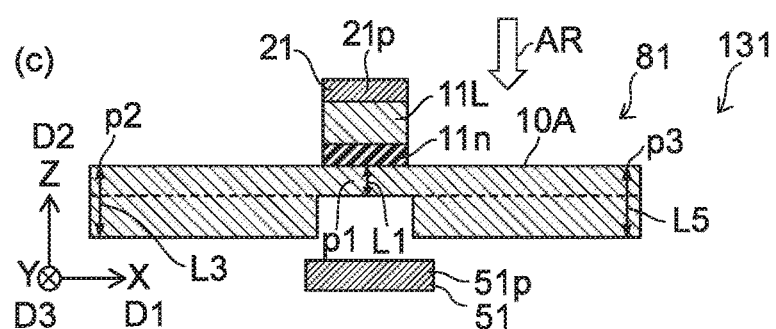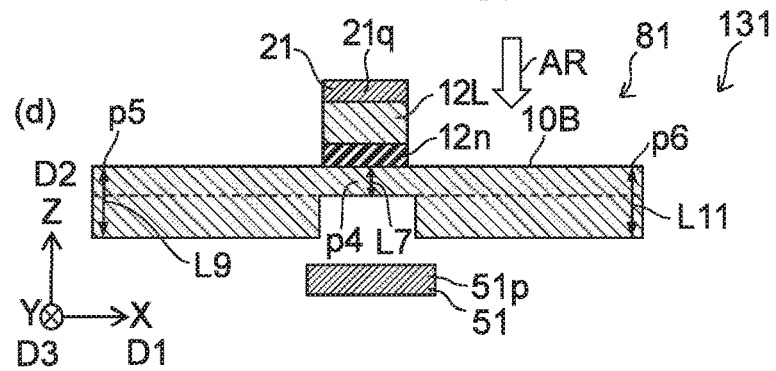
FIG. 30C
FIG. 30D

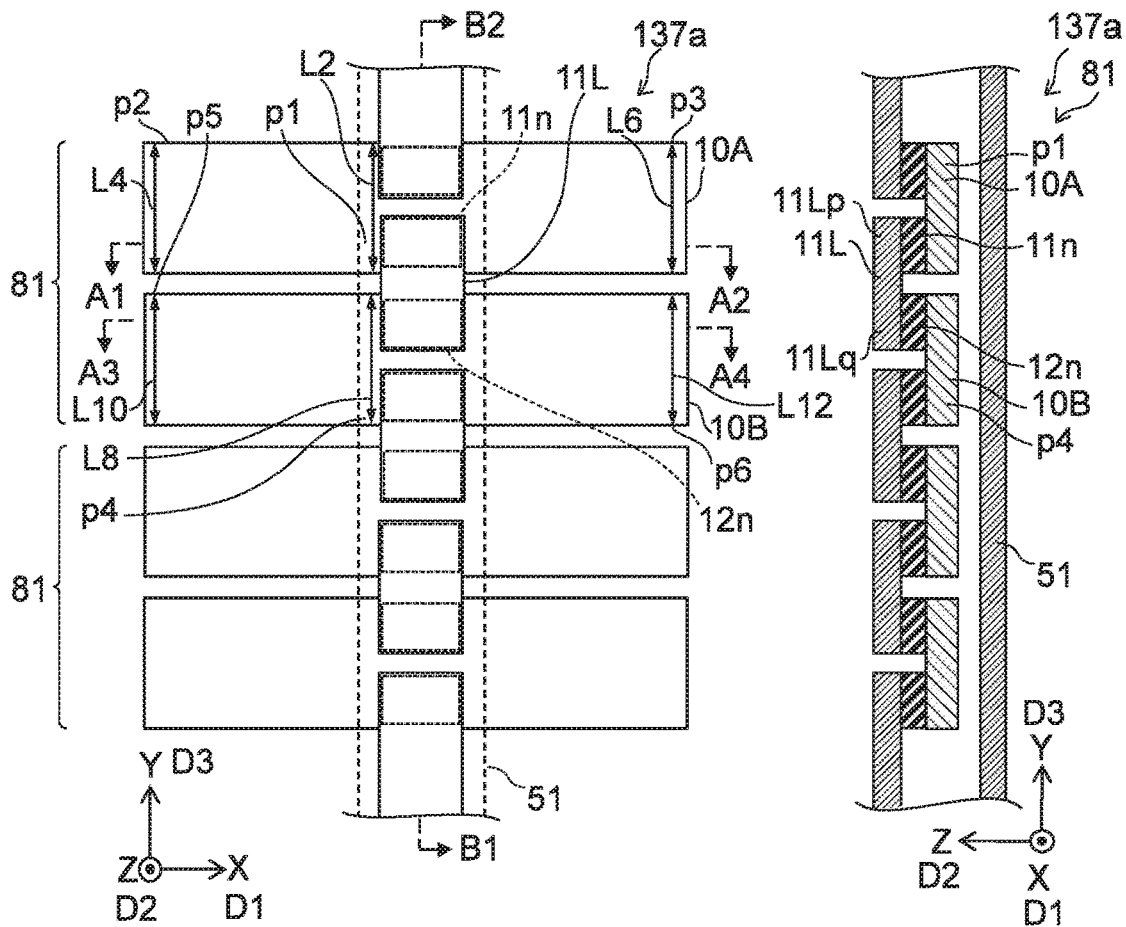
FIG. 39A  FIG. 39B
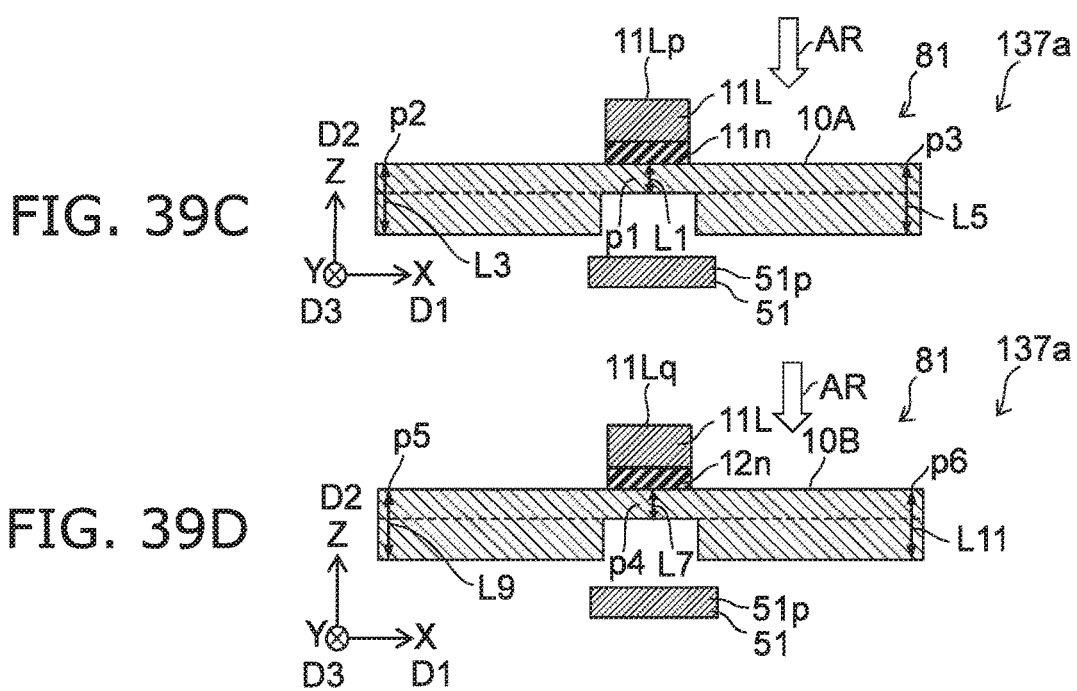
FIG. 39C
FIG. 39D

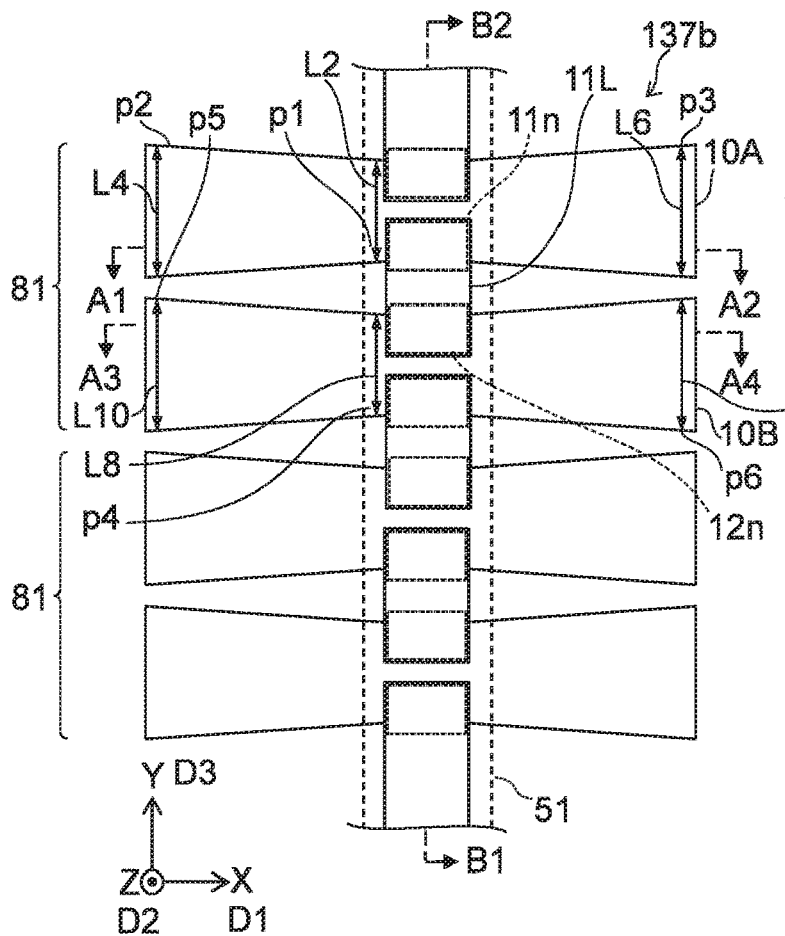
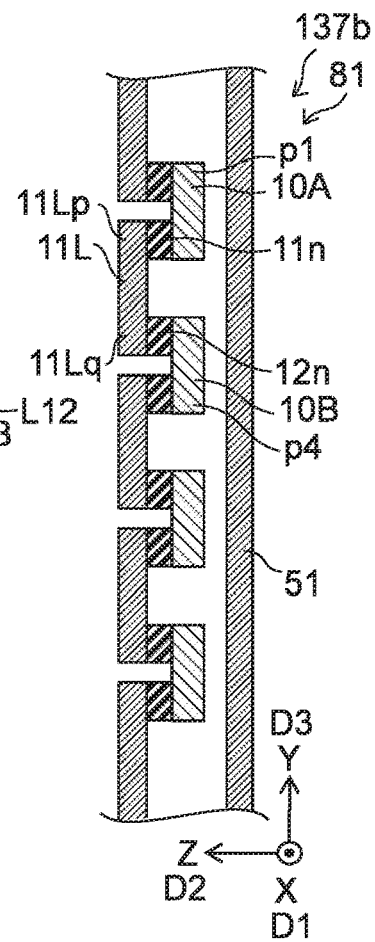
FIG. 40A  FIG. 40B
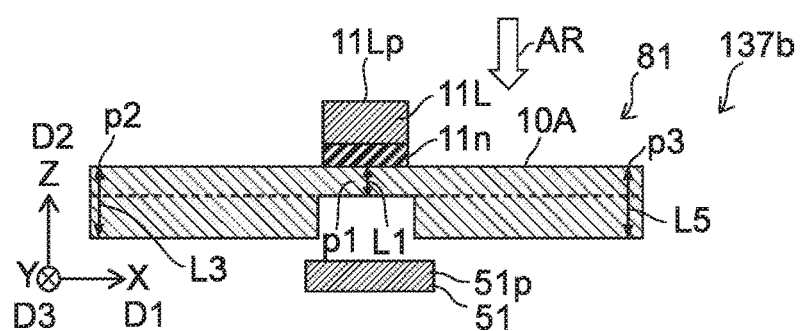
FIG. 40C
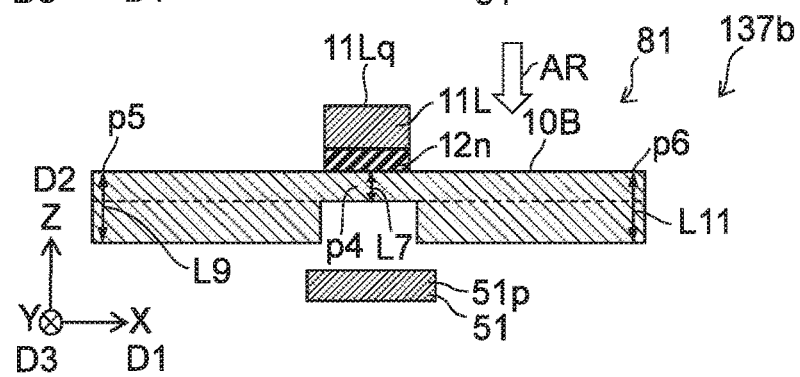
FIG. 40D

MAGNETIC SENSOR AND DIAGNOSTIC DEVICE

CROSS-REFERENCE TO RELATED APPLICATIONS

This application is based upon and claims the benefit of priority from Japanese Patent Application No. 2019-167630, filed on Sep. 13, 2019, and Japanese Patent Application No. 2020-040055, filed on Mar. 9, 2020; the entire contents of which are incorporated herein by reference.

FIELD

Embodiments described herein relate generally to a magnetic sensor and a diagnostic device.

BACKGROUND

There is a magnetic sensor using a magnetic layer. There is a diagnostic device using the magnetic sensor. It is desirable to increase the sensitivity of the magnetic sensor.

BRIEF DESCRIPTION OF THE DRAWINGS

FIG. 4A to FIG. 4C are graphs illustrating characteristics of the magnetic sensor according to the first embodiment;

FIG. 29A to FIG. 29D are schematic views illustrating a magnetic sensor according to a fourth embodiment;

FIG. 30A to FIG. 30D are schematic views illustrating a magnetic sensor according to the fourth embodiment;

FIG. 39A to FIG. 39D are schematic views illustrating a magnetic sensor according to the fourth embodiment;

FIG. 40A to FIG. 40D are schematic views illustrating a magnetic sensor according to the fourth embodiment;

DETAILED DESCRIPTION

Figure 1A:
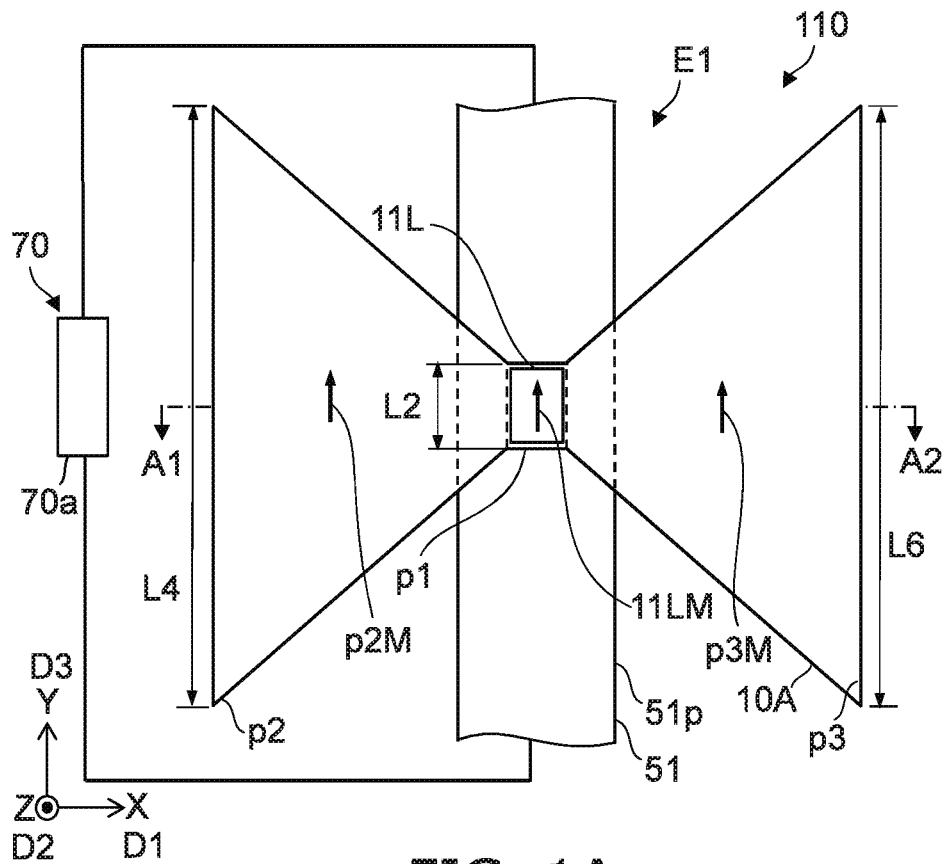
FIG. 1A and FIG. 1B are schematic views illustrating a magnetic sensor according to a first embodiment.

According to one embodiment, a magnetic sensor comprises a first structure body. The first structure body including a first magnetic part, a second magnetic part, a first conductive member, a first magnetic layer, a second magnetic layer, a first nonmagnetic portion, and a second nonmagnetic portion. The first magnetic part includes a first portion, a second portion, and a third portion. A direction from the second portion toward the third portion is aligned with a first direction. The first portion is between the second portion and the third portion in the first direction. The first portion has a first length and a second length. The first length is along a second direction crossing the first direction. The second length is along a third direction crossing a plane including the first direction and the second direction. The second portion has at least one of a third length along the second direction or a fourth length along the third direction. The third length is longer than the first length. The fourth length is longer than the second length. The third portion has at least one of a fifth length along the second direction or a sixth length along the third direction. The fifth length is longer than the first length. The sixth length is longer than the second length. The second magnetic part includes a fourth portion, a fifth portion, and a sixth portion. A direction from the fifth portion toward the sixth portion is aligned with the first direction. The fourth portion is between the fifth portion and the sixth portion in the first direction. The fourth portion has a seventh length along the second direction and an eighth length along the third direction. The fifth portion has at least one of a ninth length along the second direction or a tenth length along the third direction. The ninth length is longer than the seventh length. The tenth length is longer than the eighth length. The sixth portion has at least one of an eleventh length along the second direction or a twelfth length along the third direction. The eleventh length is longer than the seventh length. The twelfth length is longer than the eighth length. A direction from a portion of the first portion toward a portion of the first conductive member is aligned with the second direction. A direction from a portion of the fourth portion toward an other portion of the first conductive member is aligned with the second direction. The first magnetic layer is provided between the portion of the first portion and the portion of the first conductive member. The second magnetic layer is provided between the portion of the fourth portion and the other portion of the first conductive member. The first nonmagnetic portion is provided between the first magnetic layer and the portion of the first portion. The second nonmagnetic portion is provided between the second magnetic layer and the portion of the fourth portion.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
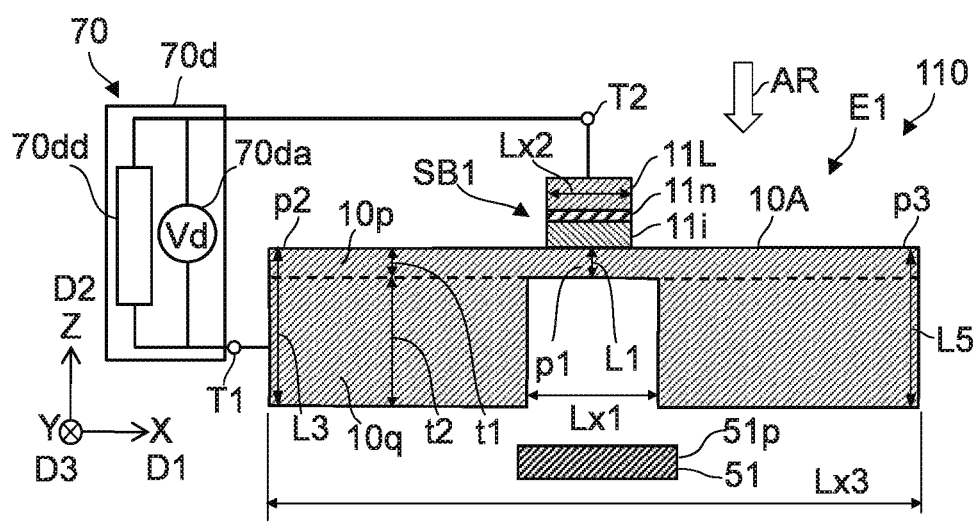

FIG. 1A and FIG. 1B are schematic views illustrating a magnetic sensor according to a first embodiment.

FIG. 1A is a plan view as viewed along arrow AR of FIG. 1B. FIG. 1B is a line A1-A2 cross-sectional view of FIG. 1A.

As shown in FIG. 1A and FIG. 1B, the magnetic sensor 110 according to the embodiment includes a first element E1. The first element E1 includes a first magnetic part 10A, a first magnetic layer 11L, a first nonmagnetic portion 11n, and a first intermediate magnetic layer 11i.

The first magnetic part 10A includes a first portion p1, a second portion p2, and a third portion p3. The direction from the second portion p2 toward the third portion p3 is aligned with a first direction D1.

The first direction D1 is taken as an X-axis direction. One direction perpendicular to the X-axis direction is taken as a Z-axis direction. A direction perpendicular to the X-axis direction and the Z-axis direction is taken as a Y-axis direction.

The first portion p1 is between the second portion p2 and the third portion p3 in the first direction D1. The first portion p1 has a first length L1 and a second length L2. The first length L1 is the length along a second direction D2 of the first portion p1.

The second direction D2 crosses the first direction D1. The second direction D2 is, for example, the Z-axis direction. Hereinbelow, the second direction D2 is taken as the Z-axis direction.

The second length L2 is the length along a third direction D3 of the first portion p1. The third direction D3 crosses a plane including the first direction D1 and the second direction D2. The third direction D3 is, for example, the Y-axis direction. Hereinbelow, the third direction D3 is taken as the Y-axis direction.

The second portion p2 has at least one of a third length L3 along the second direction D2 that is longer than the first length L1, or a fourth length L4 along the third direction D3 that is longer than the second length L2. In the example, the third length L3 is longer than the first length L1; and the fourth length L4 is longer than the second length L2.

The third portion p3 has at least one of a fifth length L5 along the second direction D2 that is longer than the first length L1, or a sixth length L6 along the third direction D3 that is longer than the second length L2. In the example, the fifth length L5 is longer than the first length L1; and the sixth length L6 is longer than the second length L2.

The direction from the first portion p1 toward the first magnetic layer 11L is aligned with the second direction D2. The first nonmagnetic portion 11n is provided between the first portion p1 and the first magnetic layer 11L. The first nonmagnetic portion 11n includes, for example, MgO. The first intermediate magnetic layer 11i is provided between the first portion p1 and the first nonmagnetic portion 11n. The first intermediate magnetic layer 11i includes, for example, CoFeB. For example, the magnetization of the first intermediate magnetic layer 11i is aligned with the magnetization of the first magnetic part 10A. For example, the magnetization of the first intermediate magnetic layer 11i and the magnetization of the first magnetic part 10A are aligned with the third direction D3 when the external magnetic field is substantially zero. The first intermediate magnetic layer 11i, the first nonmagnetic portion 11n, and the first magnetic layer 11L are included in a first stacked body SB1.

The external magnetic field which is the detection object is applied along the first direction D1 to the first element E1. The external magnetic field enters the first magnetic part 10A; and the magnetic field concentrates in the first portion p1. The magnetization of the first intermediate magnetic layer 11i is affected by the first portion p1 where the concentration occurs. On the other hand, a magnetization 11LM of the first magnetic layer 11L is substantially fixed. The angle between the magnetization of the first intermediate magnetic layer 11i and the magnetization 11LM of the first magnetic layer 11L change due to the external magnetic field. The electrical resistance between the first magnetic part 10A and the first magnetic layer 11L changes according to the magnetic field (the external magnetic field) applied to the first element E1. The external magnetic field that is applied to the first element E1 can be detected by detecting the electrical resistance between the first magnetic part 10A and the first magnetic layer 11L.

For example, the first magnetic part 10A functions as a MFC (Magnetic Field Concentrator). For example, the first stacked body SB1 which includes the first intermediate magnetic layer 11i, the first nonmagnetic portion 11n, and the first magnetic layer 11L functions as a TMR (Tunnel Magneto Resistance Effect) element.

The first magnetic part 10A includes, for example, at least one selected from the group consisting of a Co-based amorphous alloy and a NiFe alloy. The soft magnetic properties of these materials are good. For example, a high permeability is obtained by using these materials. For example, the first intermediate magnetic layer 11i is magnetically coupled with the first magnetic part 10A. For example, the first intermediate magnetic layer 11i is in contact with the first magnetic part 10A.

As recited above, a change of the length (the width or the thickness) is provided in the first magnetic part 10A. Thereby, the magnetic field concentrates easily in the first portion p1. High sensitivity is obtained thereby. According to the embodiment, a magnetic sensor can be provided in which the sensitivity can be increased.

As shown in FIG. 1B, the first magnetic part 10A may include a first layer portion 10p and a second layer portion 10q. The second portion p2 and the third portion p3 include the first layer portion 10p and the second layer portion 10q. The first portion p1 includes the first layer portion 10p but does not include the second layer portion 10q. Multiple portions that have mutually-different thicknesses (lengths in the second direction D2) are obtained using the first layer portion 10p and the second layer portion 10q. The boundary between the first layer portion 10p and the second layer portion 10q may be indistinct.

An example of simulation results of characteristics of the magnetic sensor will now be described. In the model of the simulation, a length Lx1 in the first direction D1 of the first portion p1 (referring to FIG. 1B) is 5 µm. The length Lx1 corresponds to the distance between the second portion p2 and the third portion p3. A length Lx2 along the first direction D1 of the stacked body SB1 (referring to FIG. 1B) is 4 µm. A length Lx3 along the first direction D1 of the first magnetic part 10A is 2000 µm. A thickness t1 of the first layer portion 10p (referring to FIG. 1B) is 0.02 µm. A thickness t2 of the second layer portion 10q (referring to FIG. 1B) is modified. The thickness t1 corresponds to the first length L1 of the first portion p1. The sum of the thickness t1 and the thickness t2 corresponds to the third length L3 of the second portion p2. The fifth length L5 is the same as the third length L3. The fourth length L4 of the second portion p2 (referring to FIG. 1A) is 1000 µm. The sixth length L6 of the third portion p3 is the same as the fourth length L4 of the second portion p2. The second length L2 of the first portion p1 (referring to FIG. 1A) is modified. The length changes linearly between the fourth length L4 and the second length L2. The length changes linearly between the sixth length L6 and the second length L2.

The relative permeability of the first magnetic part 10A is 2000. The magnetic properties of NiFe are applied to the magnetic properties of the first magnetic part 10A. The thickness of the first intermediate magnetic layer 11i is 2 nm. The ratio of the thickness t1 (20 nm) of the first layer portion 10p of the first magnetic part 10A to the thickness of the first intermediate magnetic layer 11i is 10. For example, when the thickness of the first intermediate magnetic layer 11i is thin and the ratio of the thickness t1 of the first layer portion 10p of the first magnetic part 10A to the thickness of the first intermediate magnetic layer 11i is high (about 10 times or more), a high permeability similar to that of NiFe is obtained even when the first intermediate magnetic layer 11i includes CoFeB because the first intermediate magnetic layer 11i is magnetically coupled with the first magnetic part 10A.

Figures 2, 3:
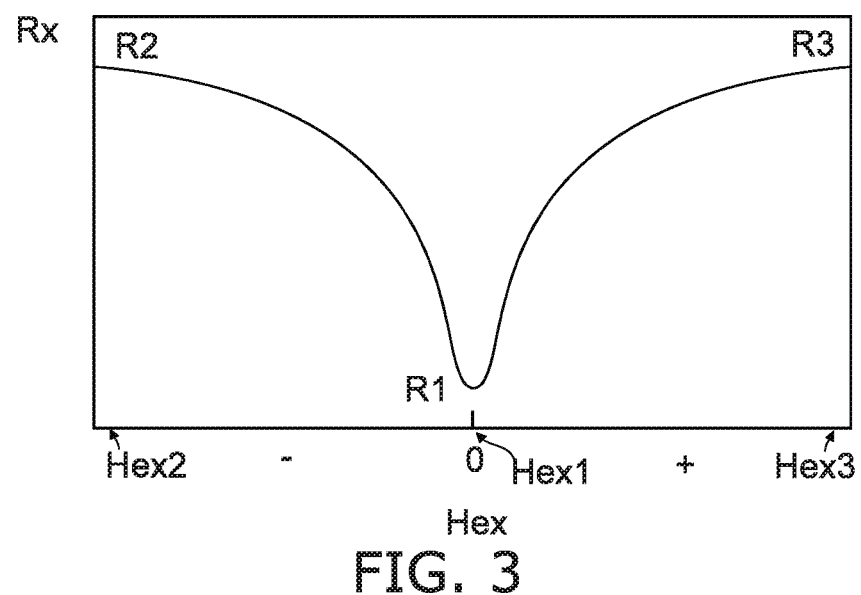
FIG. 2 is a table illustrating characteristics of the magnetic sensor.
FIG. 3 is a graph illustrating a characteristic of the magnetic sensor according to the first embodiment.

FIG. 2 is a table illustrating characteristics of the magnetic sensor.

The fourth length L4, the second length L2, the thickness t1, and the thickness t2 for first to eighth models MD1 to MD8 are shown in FIG. 2. In the first model MD1, the fourth length L4 is the same as the second length L2; and the thickness t2 is 0. A gain G that is referenced to the rotation rate of the magnetization of the first intermediate magnetic layer 11i is used for the first model MD1. The gain G corresponds to the increase factor of the rotation rate increase. The gain G of the first model MD1 is 1.

It can be seen from the first to fourth models MD1 to MD4 that the gain G increases as the second length L2 shortens. It can be seen from the fifth to eighth models MD5 to MD8 that the gain G increases as the thickness t2 increases. An extremely large gain G is obtained for the eighth model MD8. The gain G of the eighth model MD8 is 103.

According to the embodiment, a large gain G is obtained. A magnetic sensor is obtained in which the sensitivity can be increased.

In the embodiment, the change of the length between the third length L3 and the first length L1 may be continuous or step-like. For example, the length increases monotonously from the first length L1 toward the third length L3. The change of the length between the fourth length L4 and the second length L2 may be continuous or step-like. For example, the length increases monotonously from the second length L2 toward the fourth length L4.

In the embodiment, the change of the length between the fifth length L5 and the first length L1 may be continuous or step-like. For example, the length increases monotonously from the first length L1 toward the fifth length L5. The change of the length between the sixth length L6 and the second length L2 may be continuous or step-like. For example, the length increases monotonously from the second length L2 toward the sixth length L6.

For example, the magnetization 11LM of the first magnetic layer 11L is aligned with the third direction D3.

The magnetization of the first portion p1 is aligned with the orientation of a magnetization p2M of the second portion p2 and aligned with the orientation of a magnetization p3M of the third portion p3. For example, when the external magnetic field is substantially zero, the orientation of the magnetization p2M of the second portion p2 is aligned with the third direction D3. The orientation of the magnetization p3M of the third portion p3 is aligned with the third direction D3.

For example, the external magnetic field is aligned with the X-axis direction. The orientation of the magnetization of the first magnetic part 10A changes due to the external magnetic field. Thereby, the orientation of the magnetization of the first intermediate magnetic layer 11i changes. For example, when the external magnetic field is 0, the angle between the magnetization of the first intermediate magnetic layer 11i and the magnetization 11LM of the first magnetic layer 11L is substantially 0. At this time, the resistance (the electrical resistance between the first magnetic part 10A and the first magnetic layer 11L) is low. When the external magnetic field is not 0, the angle between the magnetization of the first intermediate magnetic layer 11i and the magnetization 11LM of the first magnetic layer 11L increases. At this time, the resistance is high.

For example, the first element E1 includes a first terminal T1 and a second terminal T2. The first terminal T1 is electrically connected to the first magnetic part 10A. The second terminal T2 is electrically connected to the first magnetic layer 11L.

As shown in FIG. 1B, the magnetic sensor 110 may further include a circuit part 70. The circuit part 70 includes, for example, a detection circuit 70d. The detection circuit 70d is configured to detect a value corresponding to the electrical resistance between the first magnetic part 10A and the first magnetic layer 11L. The detection circuit 70d includes, for example, a bias voltage application part 70da and a detector 70dd. For example, the bias voltage application part 70da applies a bias voltage Vb between the first terminal T1 and the second terminal T2. The detector 70dd detects a value (a signal) corresponding to the electrical resistance between the first terminal T1 and the second terminal T2.

For example, the first element E1 includes a first interconnect 51. The first interconnect 51 includes a portion 51p extending along the third direction D3. For example, at least a portion of the first interconnect 51 overlaps at least a portion of the first portion p1 in the second direction D2. A current magnetic field that is based on a current flowing in the first interconnect 51 is applied efficiently to the first stacked body SB1.

As shown in FIG. 1A, the circuit part 70 may include a current supply circuit 70a. The current supply circuit 70a is configured to supply an alternating current to the first interconnect 51. The external magnetic field and the current magnetic field due to the alternating current flowing in the first interconnect 51 are applied to the first intermediate magnetic layer 11i. A change of the electrical resistance occurs according to the current magnetic field and the external magnetic field. As described below, the noise can be reduced by processing a signal corresponding to the change of the electrical resistance.

FIG. 3 is a graph illustrating a characteristic of the magnetic sensor according to the first embodiment.

The horizontal axis of FIG. 3 is the intensity of an external magnetic field Hex applied to the first element E1. The vertical axis is an electrical resistance Rx between the first magnetic part 10A and the first magnetic layer 11L. For example, the electrical resistance Rx corresponds to the electrical resistance between the first terminal T1 and the second terminal T2. FIG. 3 corresponds to the R-H characteristic.

As shown in FIG. 3, the electrical resistance Rx between the first magnetic part 10A and the first magnetic layer 11L has an even-function characteristic of a magnetic field (the external magnetic field Hex; e.g., a magnetic field in the first direction D1) applied to the first element E1. For example, the electrical resistance Rx has a first value R1 when a first magnetic field Hex1 is applied to the first element E1. The electrical resistance Rx has a second value R2 when a second magnetic field Hex2 is applied to the first element E1. The electrical resistance Rx has a third value R3 when a third magnetic field Hex3 is applied to the first element E1. The absolute value of the first magnetic field Hex1 is less than the absolute value of the second magnetic field Hex2 and less than the absolute value of the third magnetic field Hex3. For example, the first magnetic field Hex1 is substantially 0. The orientation of the second magnetic field Hex2 is the reverse of the orientation of the third magnetic field Hex3. The first value R1 is smaller than the second value R2 and smaller than the third value R3.

An example of the change of the electrical resistance Rx when an alternating current is supplied to the first interconnect 51 and an alternating-current magnetic field due to the alternating current is applied to the first element E1 will now be described.

FIG. 4A to FIG. 4C are graphs illustrating characteristics of the magnetic sensor according to the first embodiment.

FIG. 4A shows characteristics when a signal magnetic field Hsig (the external magnetic field) applied to the first element E1 is 0. FIG. 4B shows characteristics when the signal magnetic field Hsig is positive. FIG. 4C shows characteristics when the signal magnetic field Hsig is negative. These figures show the relationship between a magnetic field H and a resistance R (corresponding to the electrical resistance Rx).

As shown in FIG. 4A, when the signal magnetic field Hsig is 0, the resistance R has a characteristic that is symmetric with respect to the positive and negative magnetic field H. When an alternating-current magnetic field Hac is zero, the resistance R is a low resistance Ro. The magnetization of the first intermediate magnetic layer 11i (e.g., a free layer) rotates substantially identically to the positive and negative magnetic field H. Therefore, a symmetric resistance increase characteristic is obtained. The fluctuation of the resistance R with respect to the alternating-current magnetic field Hac has the same value between the positive and negative polarities. The period of the change of the resistance R is 2 times the period of the alternating-current magnetic field Hac. The change of the resistance R substantially does not include the frequency component of the alternating-current magnetic field Hac.

As shown in FIG. 4B, the characteristic of the resistance R shifts to the positive magnetic field H side when a positive signal magnetic field Hsig is applied. The resistance R becomes large for the alternating-current magnetic field Hac on the positive side. The resistance R becomes small for the alternating-current magnetic field Hac on the negative side.

As shown in FIG. 4C, the characteristic of the resistance R shifts to the negative magnetic field H side when a negative signal magnetic field Hsig is applied. The resistance R becomes small for the alternating-current magnetic field Hac on the positive side. The resistance R becomes large for the alternating-current magnetic field Hac on the negative side.

Resistances R having mutually-different fluctuation occur for the positive and negative alternating-current magnetic field Hac when a signal magnetic field Hsig of a prescribed magnitude is applied. The period of the fluctuation of the resistance R with respect to the positive and negative alternating-current magnetic field Hac is the same as the period of the alternating-current magnetic field Hac. An output voltage that has an alternating current frequency component corresponding to the signal magnetic field Hsig is generated.

The characteristics recited above are obtained in the case where the signal magnetic field Hsig does not change temporally. The case where the signal magnetic field Hsig changes temporally is as follows. The frequency of the signal magnetic field Hsig is taken as a signal frequency fsig. The frequency of the alternating-current magnetic field Hac is taken as an alternating current frequency fac. In such a case, an output that corresponds to the signal magnetic field Hsig at frequencies of fac±fsig is generated.

In the case where the signal magnetic field Hsig changes temporally, the signal frequency fsig is, for example, 1 kHz or less. On the other hand, the alternating current frequency fac is sufficiently higher than the signal frequency fsig. For example, the alternating current frequency fac is not less than 10 times the signal frequency fsig.

For example, there is an application in which the magnetic field generated from a living body is detected using the magnetic sensor 110. When detecting such a biological magnetic field (e.g., neuromagnetism, cardiomagnetism, a neuron, etc.), the signal frequency fsig is 1 kHz or less. In such a case, the alternating current frequency fac is, for example, 100 kHz or more.

In the magnetic sensor 110 according to the embodiment, the external magnetic field Hex (the signal magnetic field Hsig) which is the detection object can be detected with high sensitivity by using such characteristics. An example of the detection will now be described.

Figure 5A:
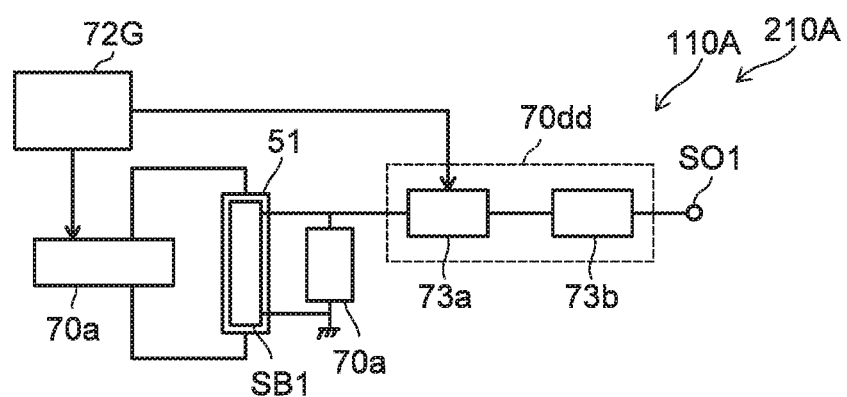
FIG. 5A and FIG. 5B are schematic views illustrating detection circuits of magnetic sensors according to the first embodiment.
Figure 5B:
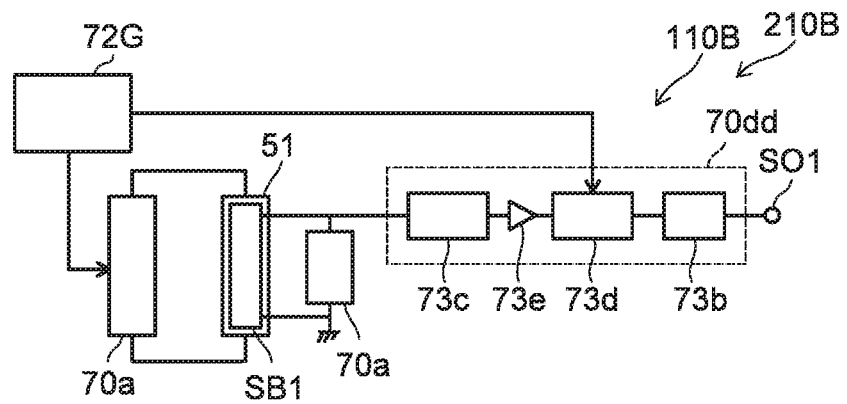

FIG. 5A and FIG. 5B are schematic views illustrating detection circuits of magnetic sensors according to the first embodiment.

A frequency generator 72G is provided in a magnetic sensor 110A and a magnetic sensor device 210A shown in FIG. 5A. The frequency generator 72G generates a signal having the alternating current frequency fac (a first frequency). This signal is supplied to the current supply circuit 70a. The current supply circuit 70a supplies, to the first interconnect 51, an alternating current having the alternating current frequency fac (the first frequency).

On the other hand, a direct current is supplied by the bias voltage application part 70da applying the bias voltage Vb to the first stacked body SB1.

In the example, the detector 70dd includes a lock-in amplifier 73a. The signal that is generated by the frequency generator 72G and has the alternating current frequency fac (the first frequency) is input to the lock-in amplifier 73a. For example, the lock-in amplifier 73a detects an alternating current signal having a frequency in a range including the first frequency (the alternating current frequency fac). In the example, the output of the lock-in amplifier 73a is output as an output signal SO1 via a low-pass filter 73b. Thereby, the output signal SO1 is a signal corresponding to the signal magnetic field Hsig.

A band-pass filter 73c and a PSD (phase sensitive detector) circuit 73d are provided in a magnetic sensor 110B and a magnetic sensor device 210B shown in FIG. 5B. A signal that corresponds to the electrical resistance Rx is input to the band-pass filter 73c. For example, the band-pass filter 73c attenuates signals of frequencies not less than 2 times the first frequency (the alternating current frequency fac). The output of the band-pass filter 73c is input to the PSD circuit 73d. In the example, the output of the band-pass filter 73c is input to an amplifier 73e; and the output of the amplifier 73e is input to the PSD circuit 73d. The signal that is generated by the frequency generator 72G and has the alternating current frequency fac (the first frequency) is input to the PSD circuit 73d.

For example, the highest frequency of the signal magnetic field Hsig is taken as a maximum frequency fsigm. In such a case, for example, the band-pass filter 73c transmits frequencies in the range of fac±fsigm. Also, the band-pass filter 73c attenuates (e.g., cuts) frequency components that are not less than 2 times the alternating current frequency fac.

In such a case as well, the output of the PSD circuit 73d is output as the output signal SO1 via the low-pass filter 73b. Thereby, the output signal SO1 is a signal corresponding to the signal magnetic field Hsig.

In the embodiment, the detector 70dd and the detection circuit 70d may have any configuration.

Figure 6:
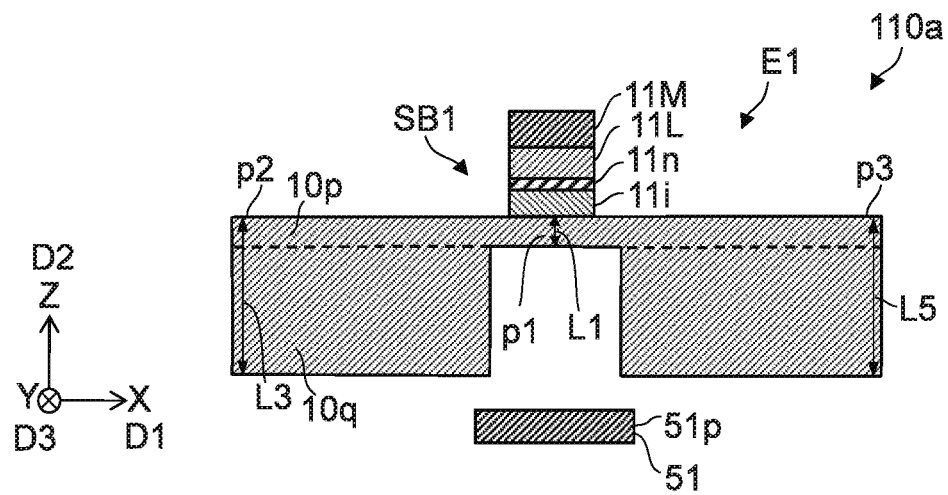
FIG. 6 is a schematic cross-sectional view illustrating a magnetic sensor according to the first embodiment.

FIG. 6 is a schematic cross-sectional view illustrating a magnetic sensor according to the first embodiment.

In the magnetic sensor 110a as shown in FIG. 6, the first element E1 may further include a first magnetic member 11M. Otherwise, the configuration of the magnetic sensor 110a may be similar to the configuration of the magnetic sensor 110.

The first magnetic member 11M is, for example, an antiferromagnetic body. The first magnetic layer 11L is between the first nonmagnetic portion 11n and the first magnetic member 11M in the second direction D2. The magnetization of the first magnetic layer 11L is substantially fixed by the first magnetic member 11M.

The first magnetic member 11M includes, for example, at least one selected from the group consisting of Ir—Mn, Pt—Mn, and NiMn.

Figure 7:
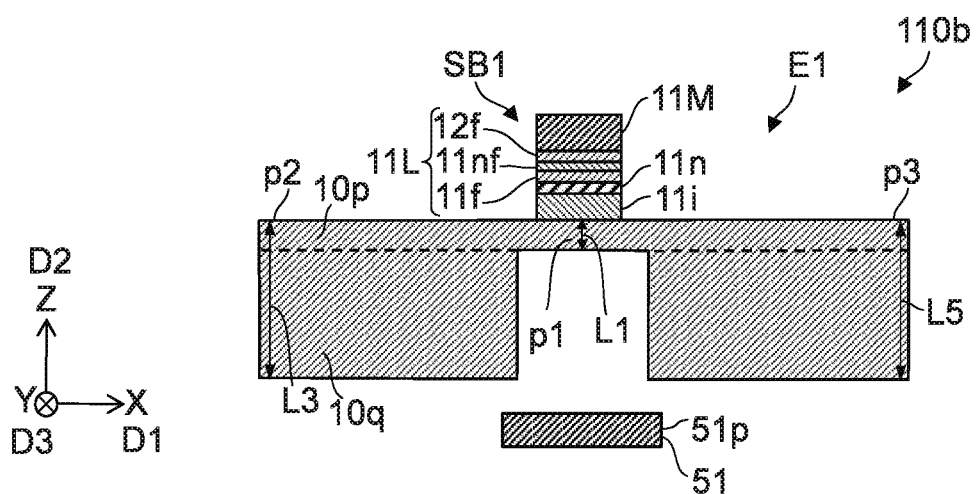
FIG. 7 is a schematic cross-sectional view illustrating a magnetic sensor according to the first embodiment.

FIG. 7 is a schematic cross-sectional view illustrating a magnetic sensor according to the first embodiment.

In the magnetic sensor 110b as shown in FIG. 7, the first magnetic layer 11L includes a first magnetic film 11f, a second magnetic film 12f, and a first nonmagnetic film 11nf. Otherwise, the configuration of the magnetic sensor 110b may be similar to the configuration of the magnetic sensor 110a.

The second magnetic film 12f is provided between the first magnetic film 11f and the first magnetic member 11M in the second direction D2. The first nonmagnetic film 11nf is provided between the first magnetic film 11f and the second magnetic film 12f. For example, the first magnetic film 11f and the second magnetic film 12f have antiferromagnetic coupling with each other. A stable magnetization 11LM of the first magnetic layer 11L is easier to obtain.

For example, the second magnetic film 12f includes a CoFe alloy, etc. The first nonmagnetic film 11nf includes, for example, Ru, etc. The first magnetic film 11f includes, for example, a stacked film including a CoFeB alloy film and a CoFe alloy film. The CoFe alloy film is provided between the CoFeB alloy film and the first nonmagnetic film 11nf.

Figure 8:
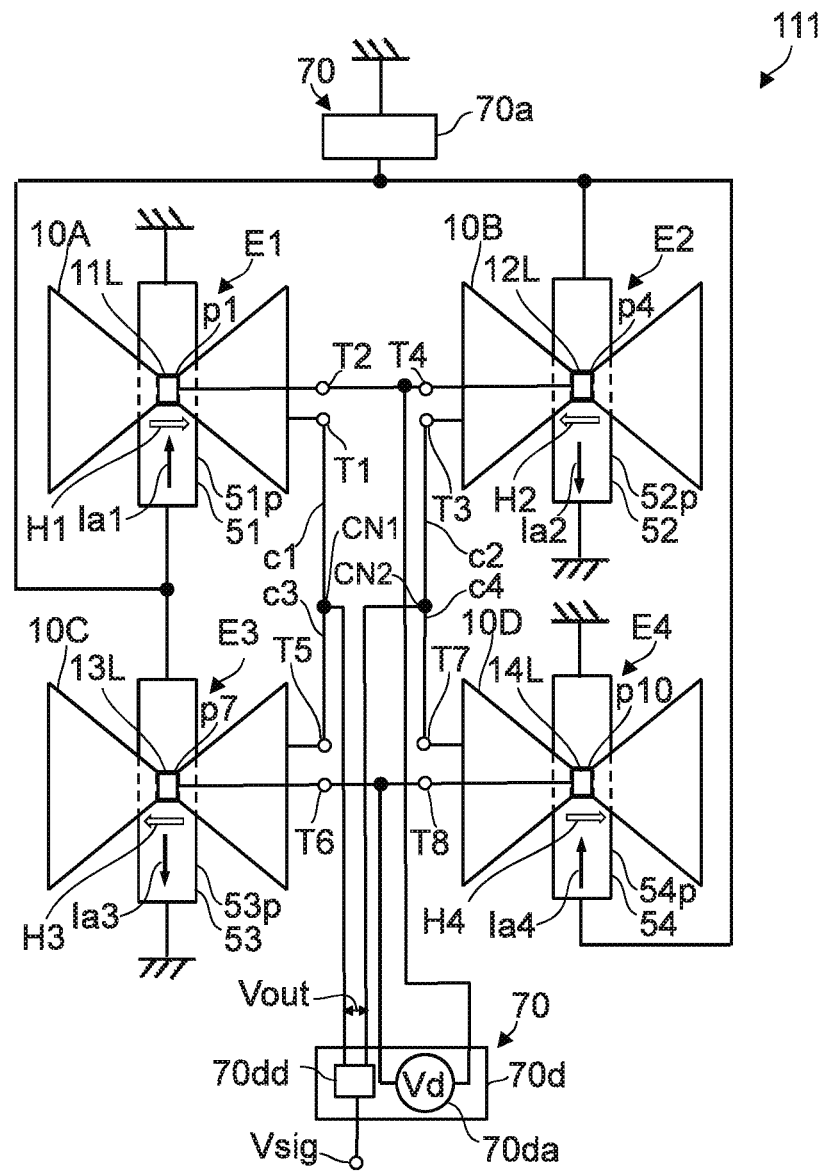
FIG. 8 is a schematic plan view illustrating a magnetic sensor according to the first embodiment.

FIG. 8 is a schematic plan view illustrating a magnetic sensor according to the first embodiment.

FIG. 9A, FIG. 9B, FIG. 10A, FIG. 10B, FIG. 11A, and FIG. 11B are schematic views illustrating the magnetic sensor according to the first embodiment.

Figure 9A:
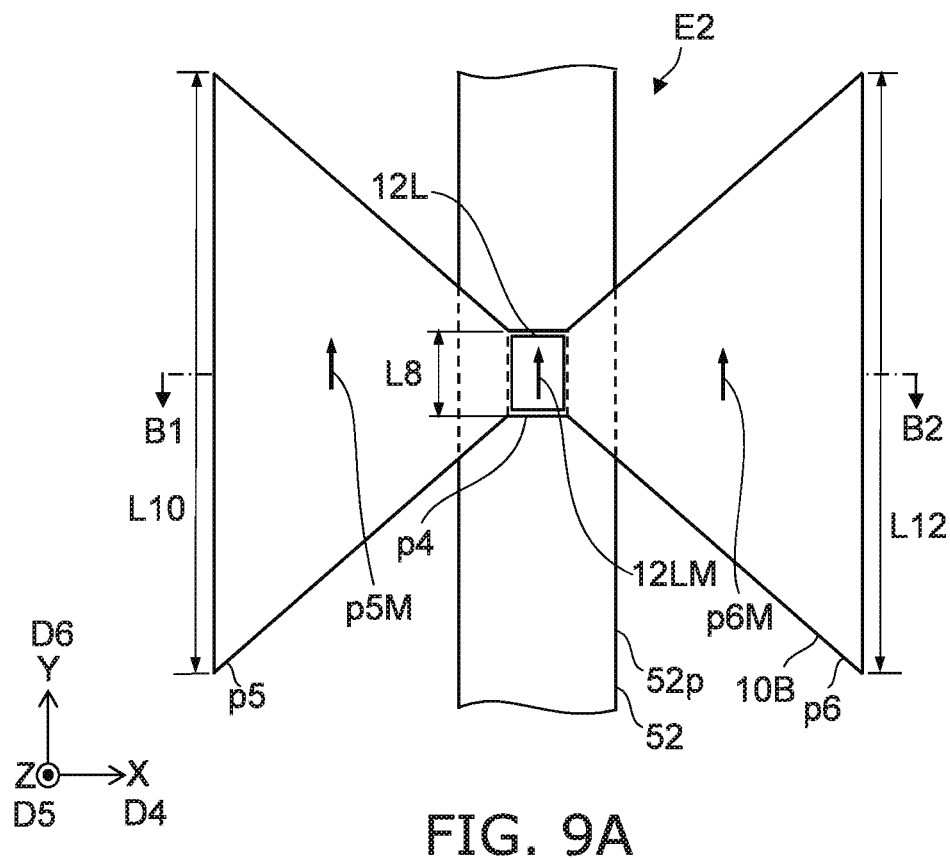
FIG. 9A and FIG. 9B are schematic views illustrating the magnetic sensor according to the first embodiment.
Figure 9B:
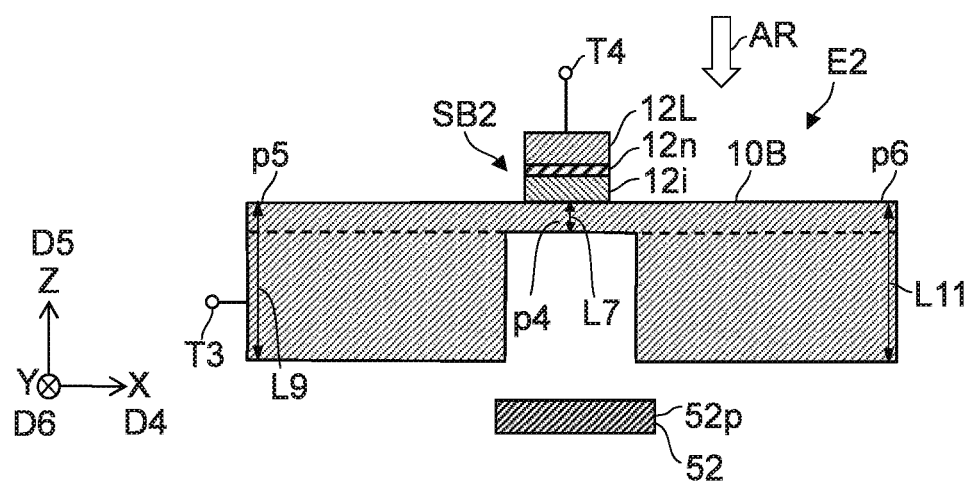
Figure 10A:
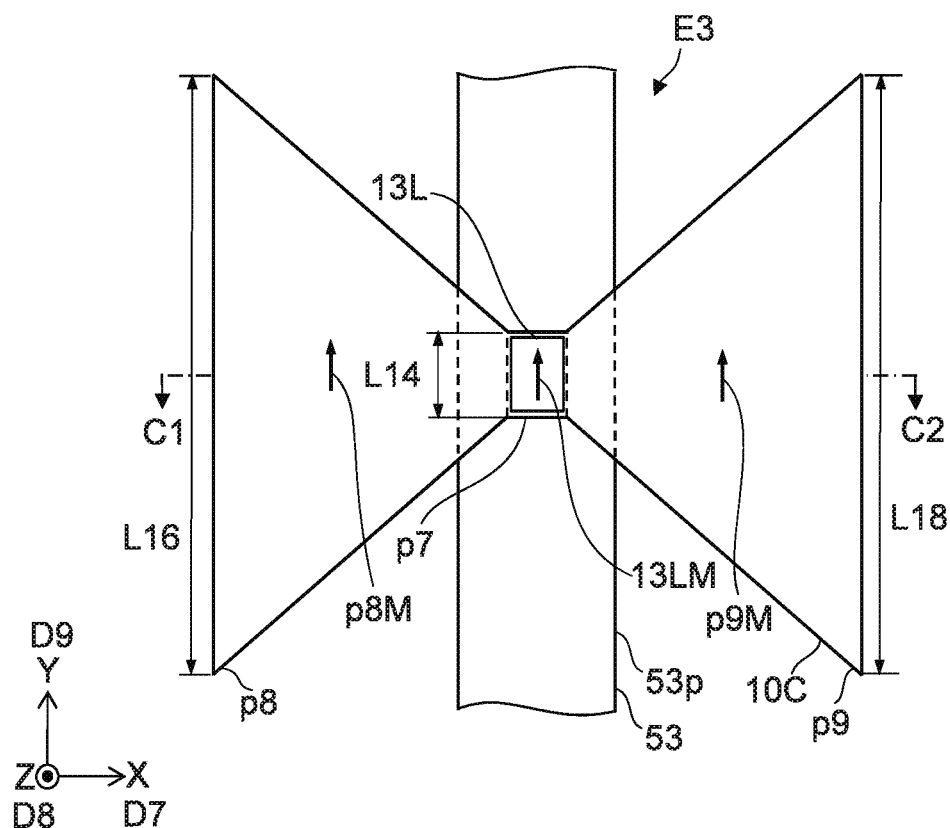
FIG. 10A and FIG. 10B are schematic views illustrating the magnetic sensor according to the first embodiment.
Figure 10B:
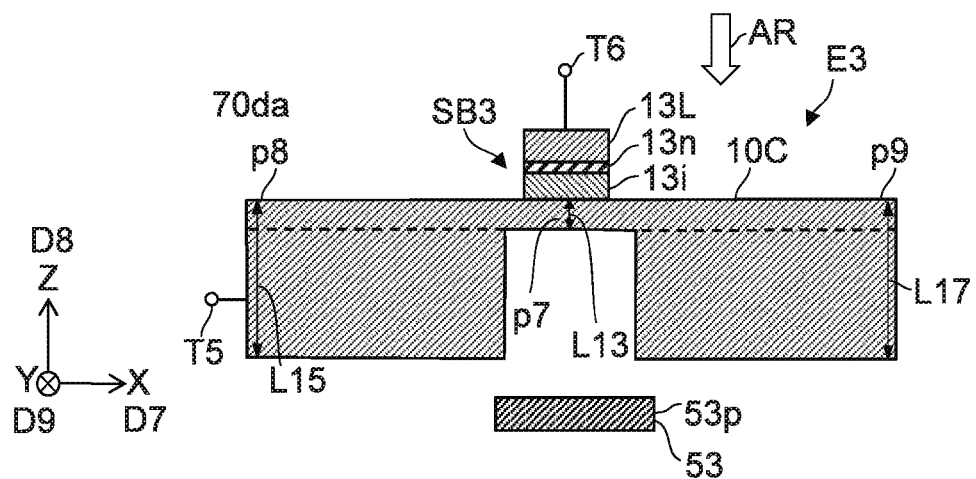
Figure 11A:
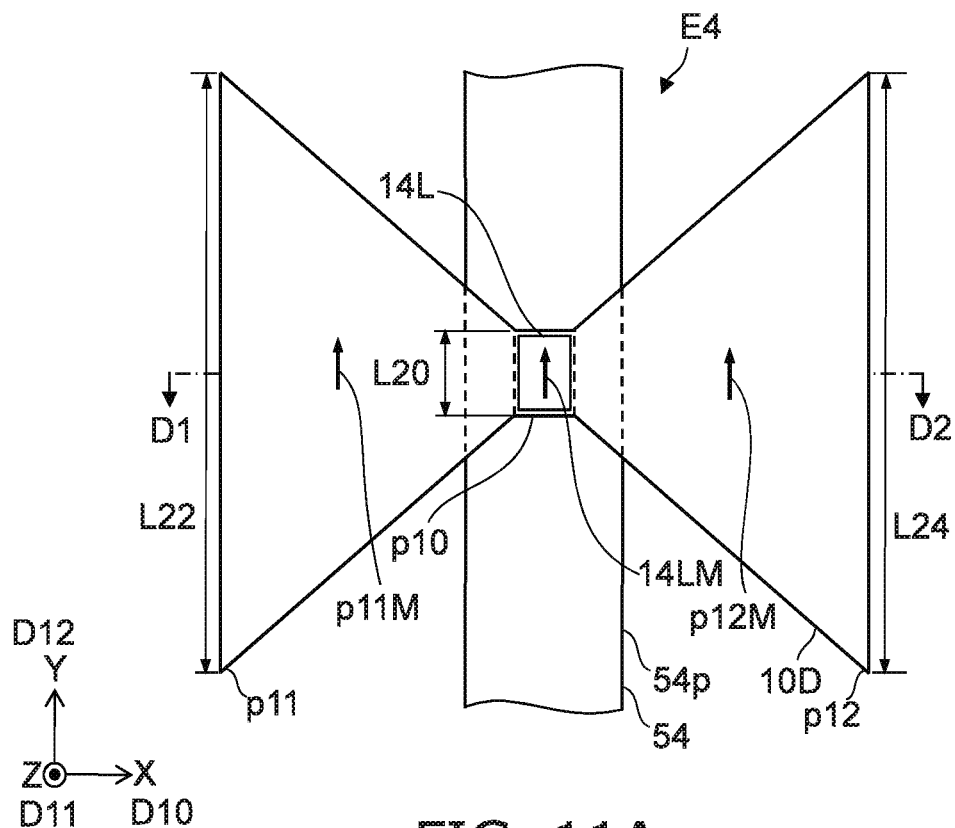
FIG. 11A and FIG. 11B are schematic views illustrating the magnetic sensor according to the first embodiment.
Figure 11B:
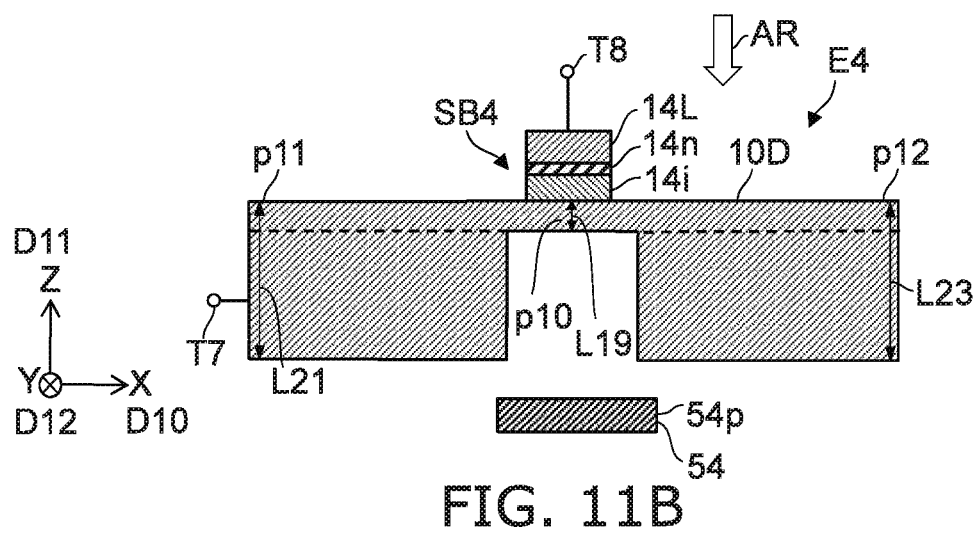

FIG. 9A is a plan view as viewed along arrow AR of FIG. 9B. FIG. 9B is a line B1-B2 cross-sectional view of FIG. 9A. FIG. 10A is a plan view as viewed along arrow AR of FIG. 10B. FIG. 10B is a line C1-C2 cross-sectional view of FIG. 10A. FIG. 11A is a plan view as viewed along arrow AR of FIG. 11B. FIG. 11B is a line D1-D2 cross-sectional view of FIG. 11A.

As shown in FIG. 8, the magnetic sensor 111 according to the embodiment further includes a second element E2, a third element E3, and a fourth element E4 in addition to the first element E1. Configurations similar to the configurations of the first element E1 in the magnetic sensors 110, 110a, and 110b are applicable to the first element E1 of the magnetic sensor 111. Configurations similar to the configurations of the first element E1 in the magnetic sensors 110, 110a, and 110b are applicable to the second element E2, the third element E3, and the fourth element E4.

As shown in FIG. 9A and FIG. 9B, the second element E2 includes a second magnetic part 10B, a second magnetic layer 12L, a second nonmagnetic portion 12n, a second intermediate magnetic layer 12i, and a second interconnect 52.

The second magnetic part 10B includes a fourth portion p4, a fifth portion p5, and a sixth portion p6. The direction from the fifth portion p5 toward the sixth portion p6 is aligned with a fourth direction D4. The fourth direction D4 is, for example, the X-axis direction. The fourth portion p4 is between the fifth portion p5 and the sixth portion p6 in the fourth direction D4. The fourth portion p4 has a seventh length L7 along a fifth direction D5 crossing the fourth direction D4, and an eighth length L8 along a sixth direction D6 crossing a plane including the fourth direction D4 and the fifth direction D5. The fifth direction D5 is, for example, the Z-axis direction. The sixth direction D6 is, for example, the Y-axis direction.

The fifth portion p5 has at least one of a ninth length L9 along the fifth direction D5 that is longer than the seventh length L7, or a tenth length L10 along the sixth direction D6 that is longer than the eighth length L8. The sixth portion p6 has at least one of an eleventh length L11 along the fifth direction D5 that is longer than the seventh length L7, or a twelfth length L12 along the sixth direction D6 that is longer than the eighth length L8.

The direction from the fourth portion p4 toward the second magnetic layer 12L is aligned with the fifth direction D5. The second nonmagnetic portion 12n is provided between the fourth portion p4 and the second magnetic layer 12L. The second intermediate magnetic layer 12i is provided between the fourth portion p4 and the second nonmagnetic portion 12n. The second interconnect 52 includes a portion 52p extending along the sixth direction D6.

The second intermediate magnetic layer 12i, the second nonmagnetic portion 12n, and the second magnetic layer 12L are included in a second stacked body SB2. The electrical resistance of the second stacked body SB2 changes according to a magnetic field applied to the second element E2.

As shown in FIG. 10A and FIG. 10B, the third element E3 includes a third magnetic part 10C, a third magnetic layer 13L, a third nonmagnetic portion 13n, a third intermediate magnetic layer 13i, and a third interconnect 53.

The third magnetic part 10C includes a seventh portion p7, an eighth portion p8, and a ninth portion p9. The direction from the eighth portion p8 toward the ninth portion p9 is aligned with a seventh direction D7. The seventh direction D7 is, for example, the X-axis direction. The seventh portion p7 is between the eighth portion p8 and the ninth portion p9 in the seventh direction D7. The seventh portion p7 has a thirteenth length L13 along an eighth direction D8 crossing the seventh direction D7, and a fourteenth length L14 along a ninth direction D9 crossing a plane including the seventh direction D7 and the eighth direction D8. The eighth direction D8 is, for example, the Z-axis direction. The ninth direction D9 is, for example, the Y-axis direction.

The eighth portion p8 has at least one of a fifteenth length L15 along the eighth direction D8 that is longer than the thirteenth length L13, or a sixteenth length L16 along the ninth direction D9 that is longer than the fourteenth length L14.

The ninth portion p9 has at least one of a seventeenth length L17 along the eighth direction D8 that is longer than the thirteenth length L13, or an eighteenth length L18 along the ninth direction D9 that is longer than the fourteenth length L14.

The direction from the seventh portion p7 toward the third magnetic layer 13L is aligned with the eighth direction D8. The third nonmagnetic portion 13n is provided between the seventh portion p7 and the third magnetic layer 13L. The third intermediate magnetic layer 13i is provided between the seventh portion p7 and the third nonmagnetic portion 13n. The third interconnect 53 includes a portion 53p extending along the ninth direction D9.

The third intermediate magnetic layer 13i, the third nonmagnetic portion 13n, and the third magnetic layer 13L are included in a third stacked body SB3. The electrical resistance of the third stacked body SB3 changes according to a magnetic field applied to the third element E3.

As shown in FIG. 11A and FIG. 11B, the fourth element E4 includes a fourth magnetic part 10D, a fourth magnetic layer 14L, a fourth nonmagnetic portion 14n, a fourth intermediate magnetic layer 14i, and a fourth interconnect 54.

The fourth magnetic part 10D includes a tenth portion p10, an eleventh portion p11, and a twelfth portion p12. The direction from the eleventh portion p11 toward the twelfth portion p12 is aligned with a tenth direction D10. The tenth direction D10 is, for example, the X-axis direction. The tenth portion p10 is between the eleventh portion p11 and the twelfth portion p12 in the tenth direction D10.

The tenth portion p10 has a nineteenth length L19 along an eleventh direction D11 crossing the tenth direction D10, and a twentieth length L20 along a twelfth direction D12 crossing a plane including the tenth direction D10 and the eleventh direction D11. The eleventh direction D11 is, for example, the Z-axis direction. The twelfth direction D12 is, for example, the Y-axis direction.

The eleventh portion p11 has at least one of a twenty-first length L21 along the eleventh direction D11 that is longer than the nineteenth length L19, or a twenty-second length L22 along the twelfth direction D12 that is longer than the twentieth length L20.

The twelfth portion p12 has at least one of a twenty-third length L23 along the eleventh direction D11 that is longer than the nineteenth length L19, or a twenty-fourth length L24 along the twelfth direction D12 that is longer than the twentieth length L20.

The direction from the tenth portion p10 toward the fourth magnetic layer 14L is aligned with the eleventh direction D11. The fourth nonmagnetic portion 14n is provided between the tenth portion p10 and the fourth magnetic layer 14L. The fourth intermediate magnetic layer 14i is provided between the tenth portion p10 and the fourth nonmagnetic portion 14n. The fourth interconnect 54 includes a portion 54p extending along the twelfth direction D12.

The fourth intermediate magnetic layer 14i, the fourth nonmagnetic portion 14n, and the fourth magnetic layer 14L are included in a fourth stacked body SB4. The electrical resistance of the fourth stacked body SB4 changes according to a magnetic field applied to the fourth element E4.

As shown in FIG. 9A, for example, a magnetization 12LM of the second magnetic layer 12L is aligned with the orientation of a magnetization p5M of the fifth portion p5 or the reverse orientation of the magnetization p5M. The magnetization 12LM of the second magnetic layer 12L is aligned with the orientation of a magnetization p6M of the sixth portion p6 or the reverse orientation of the magnetization p6M.

The magnetization of the fourth portion p4 is aligned with the orientation of the magnetization p5M of the fifth portion p5 and aligned with the orientation of the magnetization p6M of the sixth portion p6. For example, the orientation of the magnetization p5M of the fifth portion p5 is aligned with the third direction D3. The orientation of the magnetization p6M of the sixth portion p6 is aligned with the third direction D3. For example, the electrical resistance between the second magnetic part 10B and the second magnetic layer 12L has an even-function characteristic of the magnetic field applied to the second element E2.

As shown in FIG. 10A, for example, a magnetization 13LM of the third magnetic layer 13L is aligned with the orientation of a magnetization p8M of the eighth portion p8 or the reverse orientation of the magnetization p8M. The magnetization 13LM of the third magnetic layer 13L is aligned with the orientation of a magnetization p9M of the ninth portion p9 or the reverse orientation of the magnetization p9M.

The magnetization of the seventh portion p7 is aligned with the orientation of the magnetization p8M of the eighth portion p8 and aligned with the orientation of the magnetization p9M of the ninth portion p9. For example, the orientation of the magnetization p8M of the eighth portion p8 is aligned with the third direction D3. The orientation of the magnetization p9M of the ninth portion p9 is aligned with the third direction D3. For example, the electrical resistance between the third magnetic part 10C and the third magnetic layer 13L has an even-function characteristic of the magnetic field applied to the third element E3.

As shown in FIG. 11A, for example, a magnetization 14LM of the fourth magnetic layer 14L is aligned with the orientation of a magnetization p11M of the eleventh portion p11 or the reverse orientation of the magnetization p11M. The magnetization 14LM of the fourth magnetic layer 14L is aligned with the orientation of a magnetization p12M of the twelfth portion p12 or the reverse orientation of the magnetization p12M.

The magnetization of the tenth portion p10 is aligned with the orientation of the magnetization p11M of the eleventh portion p11 and aligned with the orientation of the magnetization p12M of the twelfth portion p12. For example, the orientation of the magnetization p11M of the eleventh portion p11 is aligned with the third direction D3. The orientation of the magnetization p12M of the twelfth portion p12 is aligned with the third direction D3. For example, the electrical resistance between the fourth magnetic part 10D and the fourth magnetic layer 14L has an even-function characteristic of the magnetic field applied to the fourth element E4.

As shown in FIG. 9B, for example, a third terminal T3 is electrically connected to the second magnetic part 10B. A fourth terminal T4 is electrically connected to the second magnetic layer 12L. As shown in FIG. 10B, for example, a fifth terminal T5 is electrically connected to the third magnetic part 10C. A sixth terminal T6 is electrically connected to the third magnetic layer 13L. As shown in FIG. 11B, for example, a seventh terminal T7 is electrically connected to the fourth magnetic part 10D. An eighth terminal T8 is electrically connected to the fourth magnetic layer 14L.

As shown in FIG. 8, the magnetic sensor 111 includes the circuit part 70. The circuit part 70 includes the current supply circuit 70a. The current supply circuit 70a supplies a first alternating current Ia1 to the first interconnect 51. The current supply circuit 70a supplies a second alternating current Ia2 to the second interconnect 52. The current supply circuit 70a supplies a third alternating current Ia3 to the third interconnect 53. The current supply circuit 70a supplies a fourth alternating current Ia4 to the fourth interconnect 54.

At the same time, the orientation of the first alternating current Ia1 and the orientation of the second alternating current Ia2 are reverse orientations. At the same time, the orientation of a first current magnetic field H1 generated by the first alternating current Ia1 and applied to the first portion p1 is the reverse of the orientation of a second current magnetic field H2 generated by the second alternating current Ia2 and applied to the fourth portion p4.

At the same time, the orientation of the third alternating current Ia3 and the orientation of the first alternating current Ia1 are reverse orientations. At the same time, the orientation of a third current magnetic field H3 generated by the third alternating current Ia3 and applied to the seventh portion p7 is the reverse of the orientation of the first current magnetic field H1 generated by the first alternating current Ia1 and applied to the first portion p1.

At the same time, the orientation of the fourth alternating current Ia4 and the orientation of the first alternating current Ia1 are the same orientation. At the same time, the orientation of a fourth current magnetic field H4 generated by the fourth alternating current Ia4 and applied to the tenth portion p10 is the same as the orientation of the first current magnetic field H1 generated by the first alternating current Ia1 and applied to the first portion p1.

For example, the bias voltage application part 70da applies the bias voltage Vb to the first to fourth stacked bodies SB1 to SB4. The first element E1 and the third element E3 are connected in series by a current path including the second terminal T2, the first terminal T1, the fifth terminal T5, and the sixth terminal T6. The second element E2 and the fourth element E4 are connected in series by a current path including the fourth terminal T4, the third terminal T3, the seventh terminal T7, and the eighth terminal T8. For example, the bias voltage application part 70da supplies a direct current to the current path of the first element E1 and the third element E3 and the current path of the second element E2 and the fourth element E4.

For example, the detector 70dd detects a potential difference Vout between an intermediate portion (a first connection point CN1) of the first terminal T1 and the fifth terminal T5 and an intermediate portion (a second connection point CN2) of the third terminal T3 and the seventh terminal T7 as a signal Vsig. The resistances of the first to fourth elements E1 to E4 are the same resistance when the signal magnetic field Hsig is zero. At this time, a potential is not generated between the first connection point CN1 and the second connection point CN2. When the signal magnetic field Hsig is applied, the same resistance fluctuation occurs in the first element E1 and the fourth element E4. The same resistance fluctuation occurs in the second element E2 and the third element E3. The resistance fluctuation of the first element E1 and the fourth element E4 and the resistance fluctuation of the second element E2 and the third element E3 are the reverse of each other. The potential difference Vout is generated thereby.

The orientation of the first current magnetic field H1 generated by the first alternating current Ia1 and applied to the first portion p1 has a reverse component of the orientation of the second current magnetic field H2 generated by the second alternating current Ia2 and applied to the fourth portion p4, and has a reverse component of the orientation of the third current magnetic field H3 generated by the third alternating current Ia3 and applied to the seventh portion p7.

The orientation of the fourth current magnetic field H4 generated by the fourth alternating current Ia4 and applied to the tenth portion p10 has a reverse component of the orientation of the second current magnetic field H2, and has a reverse component of the orientation of the third current magnetic field H3.

The circuit part 70 further includes the detection circuit 70d. In the example, for example, the detection circuit 70d is electrically connected to the first connection point CN1 and the second connection point CN2. The detection circuit 70d outputs the signal Vsig corresponding to the potential difference Vout between the first connection point CN1 and the second connection point CN2. At the first connection point CN1, a first current path c1 which includes the first magnetic part 10A and the first magnetic layer 11L and a third current path c3 which includes the third magnetic part 10C and the third magnetic layer 13L are electrically connected to each other in series. At the second connection point CN2, a second current path c2 which includes the second magnetic part 10B and the second magnetic layer 12L and a fourth current path c4 which includes the fourth magnetic part 10D and the fourth magnetic layer 14L are electrically connected to each other in series.

The first current path c1 which includes the first magnetic part 10A and the first magnetic layer 11L and the third current path c3 which includes the third magnetic part 10C and the third magnetic layer 13L are connected in series to each other. The detection circuit 70d applies the bias voltage Vb to the first current path c1 and the third current path c3 connected in series. The second current path c2 which includes the second magnetic part 10B and the second magnetic layer 12L and the fourth current path c4 which includes the fourth magnetic part 10D and the fourth magnetic layer 14L are connected in series to each other. The detection circuit 70d applies the bias voltage Vb to the second current path c2 and the fourth current path c4 connected in series.

Thus, a bridge circuit is formed of the first to fourth elements E1 to E4. The potential difference between the first connection point CN1 and the second connection point CN2 corresponds to the potential difference Vout. The detection circuit 70d is configured to output the signal Vsig corresponding to the potential difference Vout. The signal Vsig includes a signal corresponding to the external magnetic field which is the detection object.

As recited above, the orientation of the first current magnetic field H1 and the orientation of the fourth current magnetic field H4 have a reverse component of the orientation of the second current magnetic field H2, and have a reverse component of the orientation of the third current magnetic field H3. For example, the phase of the alternating-current magnetic field applied to the first portion p1 and the tenth portion p10 is the reverse of the phase of the alternating-current magnetic field applied to the fourth portion p4 and the seventh portion p7. For example, when only the alternating-current magnetic field due to the first interconnect 51 is applied to the element (the magnetic field from the outside such as the signal magnetic field Hsig or the like is zero), the voltage that is generated at the first connection point CN1 can be suppressed drastically (zero if the resistances of the elements are the same); therefore, for example, the unnecessary voltage of the alternating current frequency component due to the detector 70dd can be reduced. The potential difference Vout of the first connection point CN1 generated according to the signal magnetic field Hsig in the magnetic sensor 111 is 2 times that of the magnetic sensor 110.

Thus, for example, the detection circuit 70d detects the electrical signal of the connection point CN1 at which the first current path c1, the second current path c2, the third current path c3, and the fourth current path c4 are connected to each other. For the signal Vsig output from the detection circuit 70d, the output is increased; and the noise is suppressed. High sensitivity is obtained in the magnetic sensor 111.

Figure 12A:
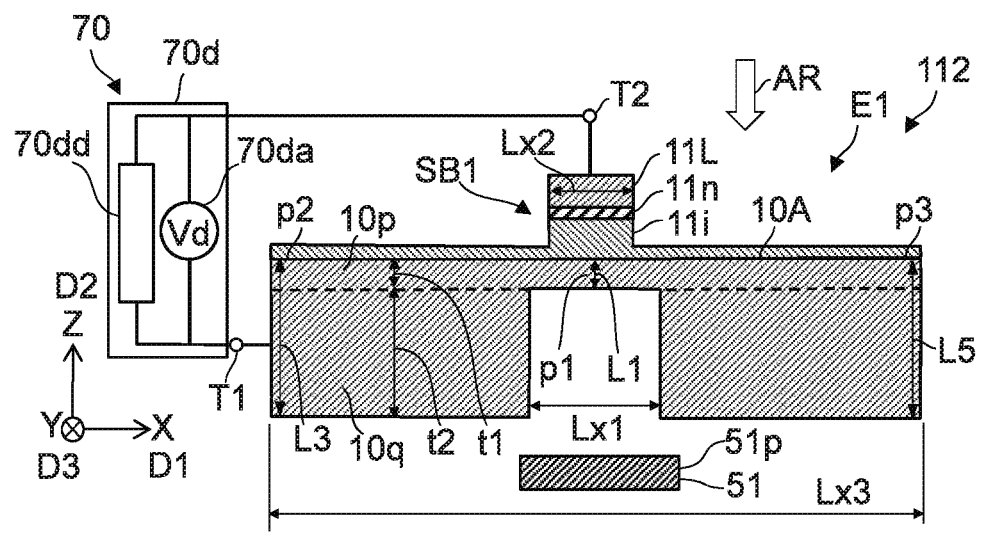
FIG. 12A and FIG. 12B are schematic cross-sectional views illustrating magnetic sensors according to the first embodiment.
Figure 12B:
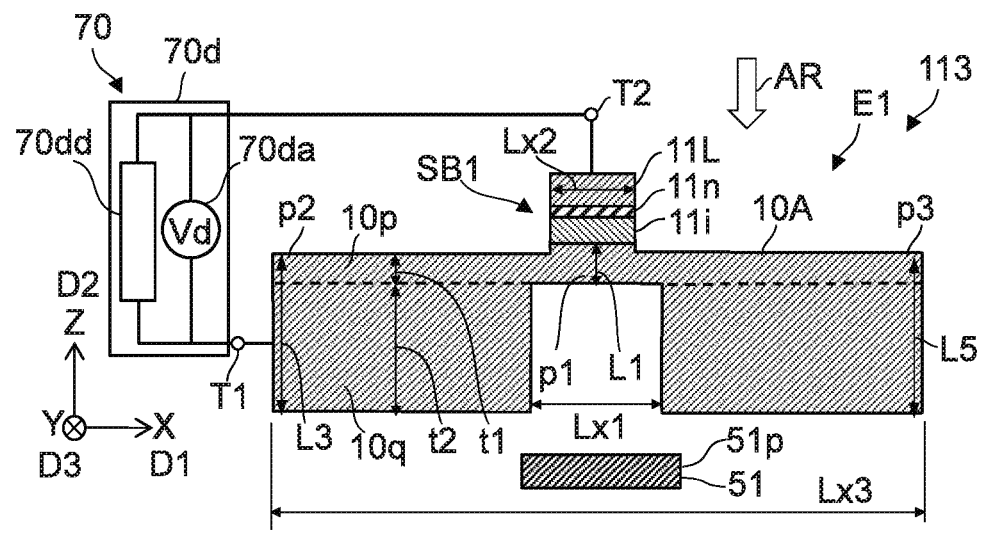

FIG. 12A and FIG. 12B are schematic cross-sectional views illustrating magnetic sensors according to the first embodiment.

FIG. 12A and FIG. 12B correspond to FIG. 1B.

In a magnetic sensor 112 as shown in FIG. 12A, a portion of the first intermediate magnetic layer 11i overlaps the second portion p2 and the third portion p3 in the second direction D2. Another portion of the first intermediate magnetic layer 11i overlaps the first portion p1 in the second direction D2. The thickness of the portion of the first intermediate magnetic layer 11i recited above may be thinner than the thickness of the other portion of the first intermediate magnetic layer 11i recited above. Otherwise, the configuration of the magnetic sensor 112 may be similar to that of the magnetic sensor 110.

In a magnetic sensor 113 as shown in FIG. 12B as well, the first magnetic part 10A includes the first portion p1. The first portion p1 includes a portion overlapping the first magnetic layer 11L in the second direction D2, and a portion not overlapping the first magnetic layer 11L in the second direction D2. The thickness (the length along the second direction D2) of the portion overlapping the first magnetic layer 11L in the second direction D2 is thicker than the thickness (the length along the second direction D2) of the portion not overlapping the first magnetic layer 11L in the second direction D2. Thus, the first portion p1 may include portions having mutually-different thicknesses. In such a case, the thickness (the length along the second direction D2) of the portion overlapping the first magnetic layer 11L in the second direction D2 may be used as the thickness (the first length L1) of the first portion p1. Otherwise, the configuration of the magnetic sensor 113 may be similar to that of the magnetic sensor 110.

In the magnetic sensors 112 and 113 as well, a magnetic sensor can be provided in which the sensitivity can be increased.

Second Embodiment

Figure 13A:
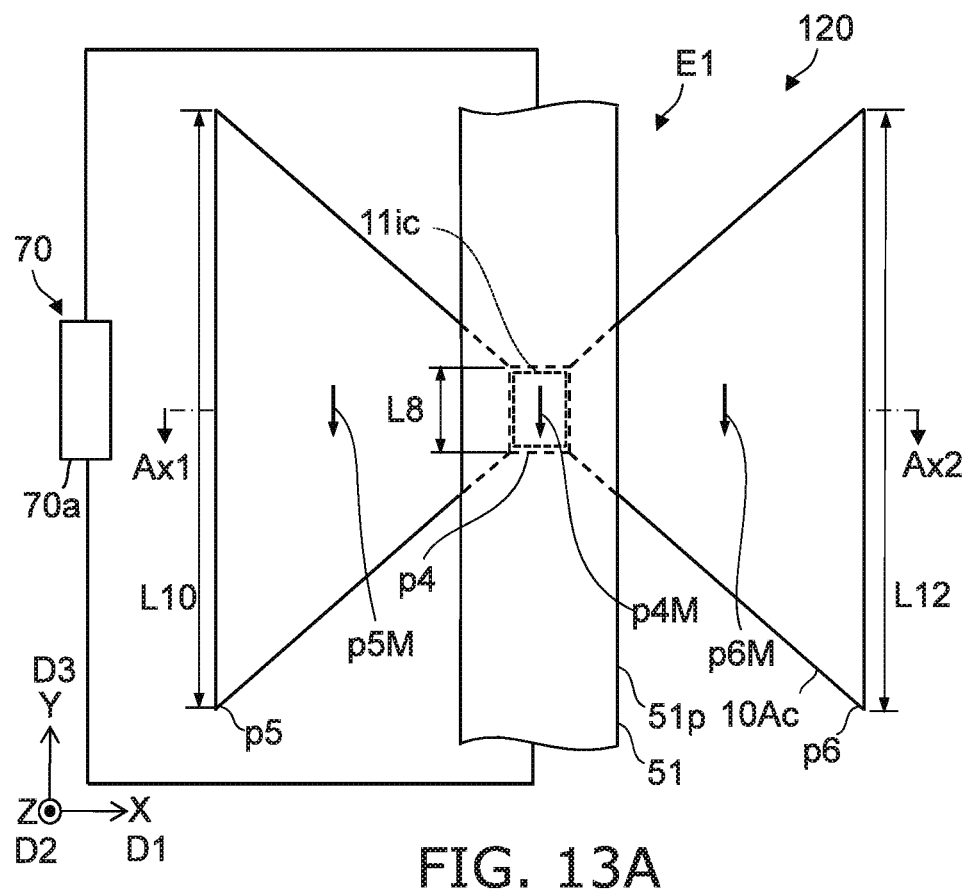
FIG. 13A and FIG. 13B are schematic views illustrating a magnetic sensor according to a second embodiment.
Figure 13B:
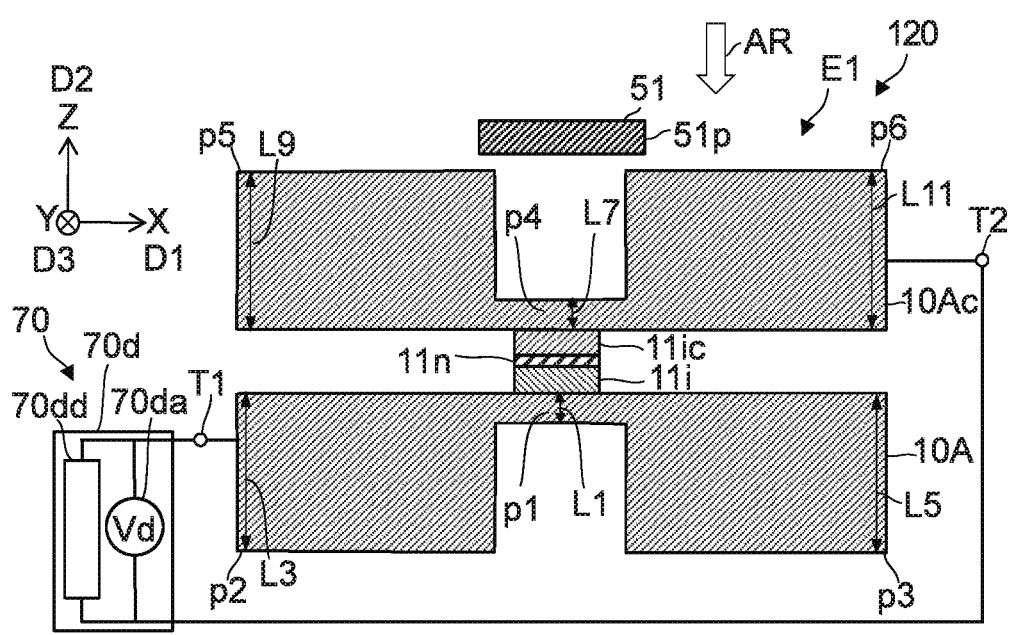

FIG. 13A and FIG. 13B are schematic views illustrating a magnetic sensor according to a second embodiment.

Figure 14:
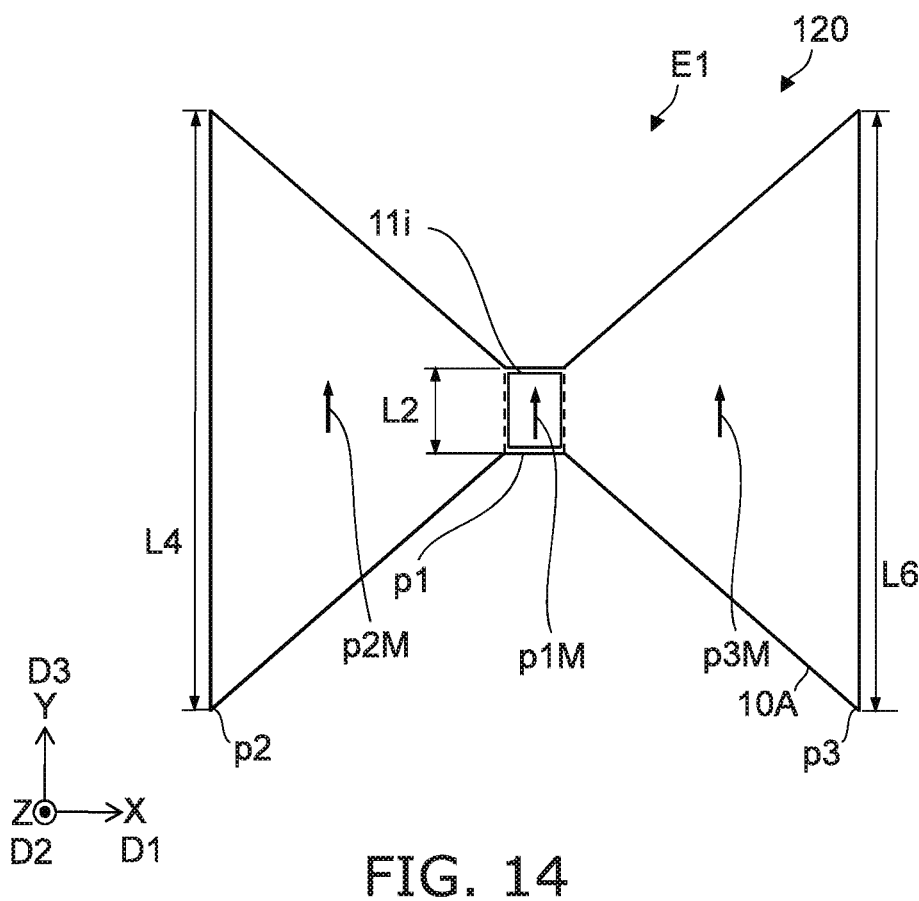
FIG. 14 is a schematic plan view illustrating the magnetic sensor according to the second embodiment.

FIG. 14 is a schematic plan view illustrating the magnetic sensor according to the second embodiment.

FIG. 13A is a plan view as viewed along arrow AR of FIG. 13B. FIG. 13B is an Ax1-Ax2 line cross-sectional view of FIG. 13A. FIG. 14 illustrates a portion of the magnetic sensor 120.

As shown in FIG. 13A and FIG. 13B, the magnetic sensor 120 according to the embodiment includes the first element E1. The first element E1 includes the first magnetic part 10A, a first counter magnetic part 10Ac, the first nonmagnetic portion 11n, the first intermediate magnetic layer 11i, and a first counter intermediate magnetic layer 11ic.

The first magnetic part 10A includes the first portion p1, the second portion p2, and the third portion p3. The direction from the second portion p2 toward the third portion p3 is aligned with the first direction D1. The first direction D1 is, for example, the X-axis direction. The first portion p1 is between the second portion p2 and the third portion p3 in the first direction D1.

The first portion p1 has the first length L1 along the second direction D2 crossing the first direction D1, and the second length L2 along the third direction D3 crossing a plane including the first direction D1 and the second direction D2. The second direction D2 is, for example, the Z-axis direction. The third direction D3 is, for example, the Y-axis direction.

The second portion p2 has at least one of the third length L3 along the second direction D2 that is longer than the first length L1, or the fourth length L4 along the third direction D3 that is longer than the second length L2. The third portion p3 has at least one of the fifth length L5 along the second direction D2 that is longer than the first length L1, or the sixth length L6 along the third direction D3 that is longer than the second length L2.

The first counter magnetic part 10Ac includes the fourth portion p4, the fifth portion p5, and the sixth portion p6. The direction from the first portion p1 toward the fourth portion p4 is aligned with the second direction D2. The direction from the second portion p2 toward the fifth portion p5 is aligned with the second direction D2. The direction from the third portion p3 toward the sixth portion p6 is aligned with the second direction D2. The fourth portion p4 is between the fifth portion p5 and the sixth portion p6 in the first direction D1.

The fourth portion p4 has the seventh length L7 along the second direction D2 and the eighth length L8 along the third direction D3. The fifth portion p5 has at least one of the ninth length L9 along the second direction D2 that is longer than the seventh length L7, or the tenth length L10 along the third direction D3 that is longer than the eighth length L8. The sixth portion p6 has at least one of the eleventh length L11 along the second direction D2 that is longer than the seventh length L7, or the twelfth length L12 along the third direction D3 that is longer than the eighth length L8.

The first nonmagnetic portion 11n is provided between the first portion p1 and the fourth portion p4. The first intermediate magnetic layer 11i is provided between the first portion p1 and the first nonmagnetic portion 11n. The first counter intermediate magnetic layer 11ic is provided between the first nonmagnetic portion 11n and the fourth portion p4.

In the magnetic sensor 120, by using the first magnetic part 10A and the first counter magnetic part 10Ac having the configurations recited above, the external magnetic field Hex which is the detection object can be concentrated efficiently in the first portion p1 and the fourth portion p4. According to the embodiment, a magnetic sensor can be provided in which the sensitivity can be increased.

For example, a magnetization p1M of the first portion p1 is aligned with the orientation of the magnetization p2M of the second portion p2 and the orientation of the magnetization p3M of the third portion p3. For example, a magnetization p4M of the fourth portion p4 is aligned with the orientation of the magnetization p5M of the fifth portion p5 and the orientation of the magnetization p6M of the sixth portion p6.

For example, the magnetization p5M of the fifth portion p5 is aligned with the reverse orientation of the magnetization p2M of the second portion p2. The magnetization p6M of the sixth portion p6 is aligned with the reverse orientation of the magnetization p3M of the third portion p3.

For example, the first terminal T1 is electrically connected to the first magnetic part 10A. The second terminal T2 is electrically connected to the first counter magnetic part 10Ac. The electrical resistance between the first magnetic part 10A and the first counter magnetic part 10Ac corresponds to the electrical resistance between the first terminal T1 and the second terminal T2.

For example, the electrical resistance Rx between the first magnetic part 10A and the first counter magnetic part 10Ac has an even-function characteristic of the magnetic field (e.g., the magnetic field along the first direction D1) applied to the first element E1.

Figure 15:
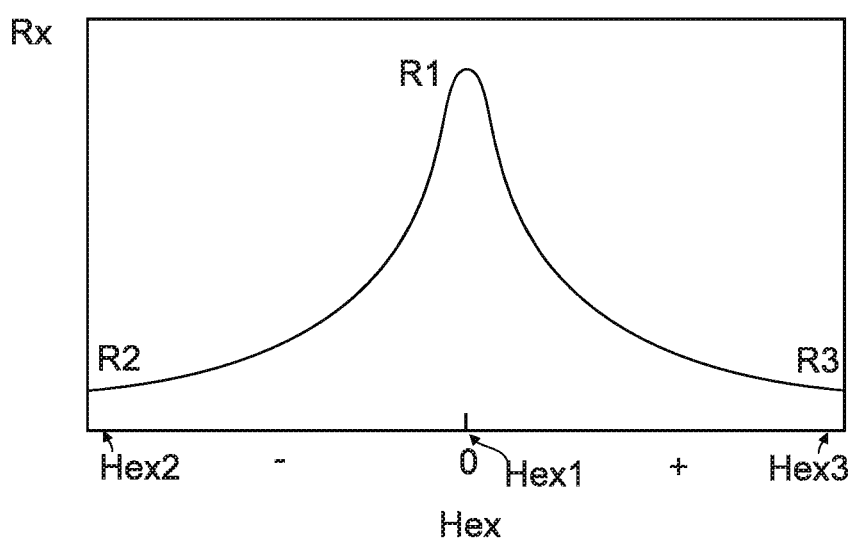
FIG. 15 is a graph illustrating a characteristic of the magnetic sensor according to the second embodiment.

FIG. 15 is a graph illustrating a characteristic of the magnetic sensor according to the second embodiment.

The horizontal axis of FIG. 15 is the intensity of the external magnetic field Hex applied to the first element E1. The vertical axis is the electrical resistance Rx between the first magnetic part 10A and the first magnetic layer 11L. For example, the electrical resistance Rx corresponds to the electrical resistance between the first terminal T1 and the second terminal T2. FIG. 15 corresponds to the R-H characteristic.

As shown in FIG. 15, for example, the electrical resistance Rx between the first magnetic part 10A and the first counter magnetic part 10Ac has the first value R1 when the first magnetic field Hex1 is applied to the first element E1, has the second value R2 when the second magnetic field Hex2 is applied to the first element E1, and has the third value R3 when the third magnetic field Hex3 is applied to the first element E1. The absolute value of the first magnetic field Hex1 is less than the absolute value of the second magnetic field Hex2 and less than the absolute value of the third magnetic field Hex3. The orientation of the second magnetic field Hex2 is the reverse of the orientation of the third magnetic field Hex3. The first value R1 is larger than the second value R2 and larger than the third value R3.

For example, the first element E1 further includes the first interconnect 51. The first interconnect 51 includes the portion 51p extending along the third direction D3. For example, at least a portion of the first interconnect 51 overlaps at least a portion of the first portion p1 in the second direction D2. At least a portion of the first interconnect 51 overlaps at least a portion of the fourth portion p4 in the second direction D2.

The magnetic sensor 120 further includes the circuit part 70. The circuit part 70 includes the current supply circuit 70a and the detection circuit 70d. The current supply circuit 70a is configured to supply an alternating current to the first interconnect 51. The detection circuit 70d is configured to detect a value corresponding to the electrical resistance Rx.

The noise can be suppressed by utilizing the electrical resistance Rx having an even-function characteristic of the magnetic field applied to the first element E1. In the magnetic sensor 120, for example, the magnetization of the first intermediate magnetic layer 11i and the magnetization of the first counter intermediate magnetic layer 11ic rotate according to the signal magnetic field Hsig. For example, the angle difference between the magnetization of the first intermediate magnetic layer 11i and the magnetization of the first counter intermediate magnetic layer 11ic in the magnetic sensor 120 is 2 times the change of the angle of the magnetization in the magnetic sensor 110. Thereby, the output of the magnetic sensor 120 is 2 times that of the magnetic sensor 110. For example, the magnetic field detection sensitivity of the magnetic sensor 120 is 2 times.

FIG. 16A to FIG. 16D and FIG. 17A to FIG. 17D are schematic views illustrating portions of the magnetic sensor according to the second embodiment.

Figure 16A:
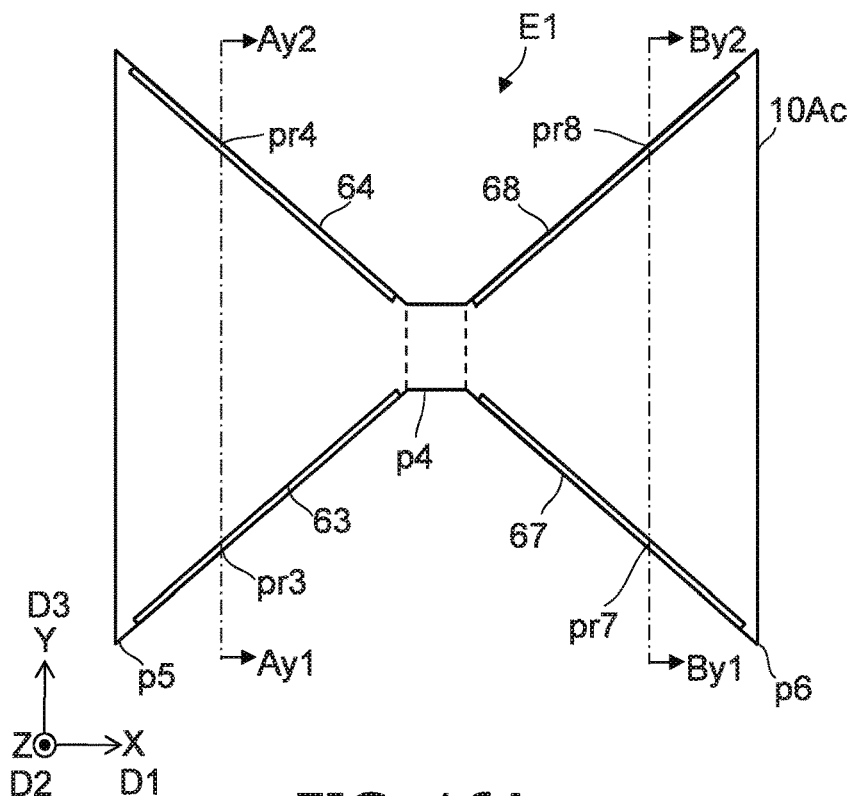
FIG. 16A to FIG. 16D are schematic views illustrating portions of the magnetic sensor according to the second embodiment.
Figure 16B:
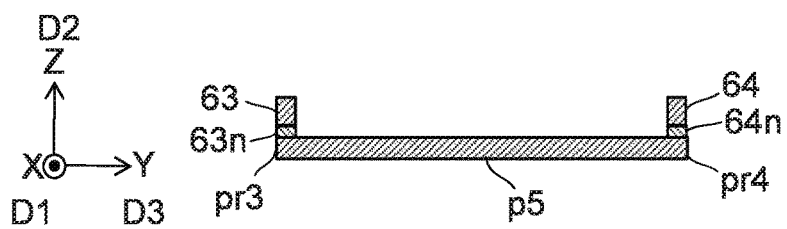
Figure 16C:
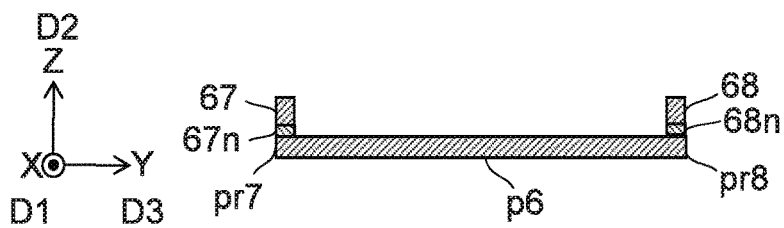
Figure 17A:
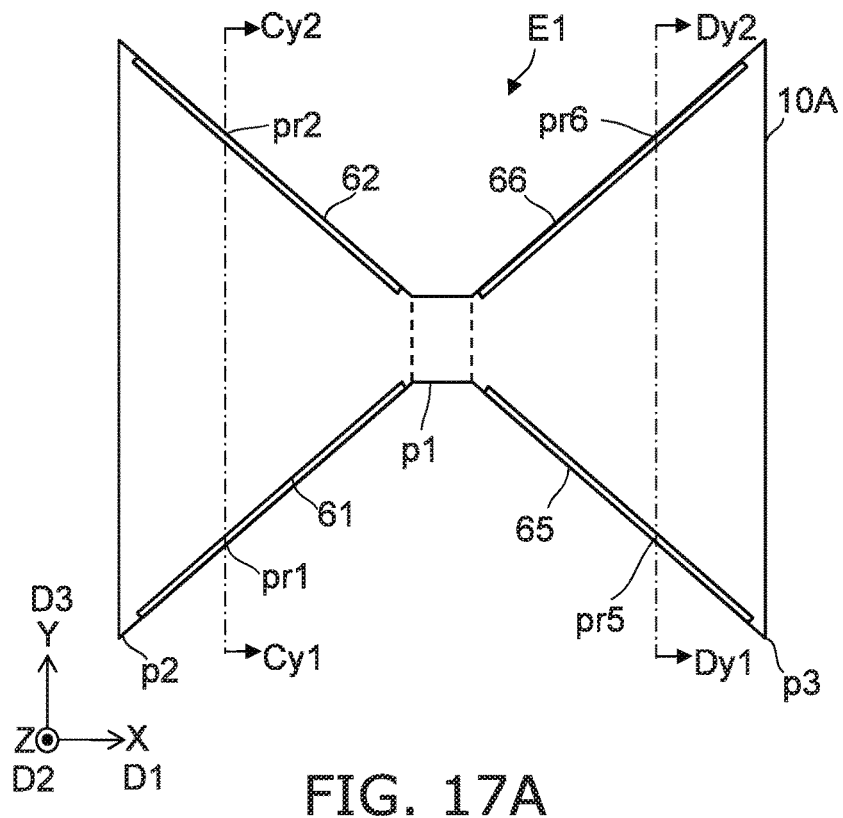
FIG. 17A to FIG. 17D are schematic views illustrating portions of the magnetic sensor according to the second embodiment.
Figure 17B:
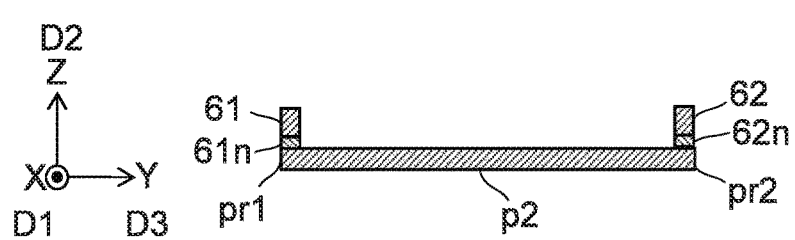
Figure 17C:
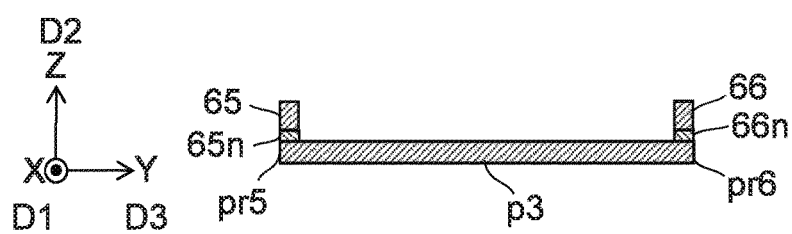

FIG. 16A is a plan view. FIG. 16B is an Ay1-Ay2 line cross section of FIG. 16A. FIG. 16C is a By1-By2 line cross section of FIG. 16A. FIG. 17A is a plan view. FIG. 17B is a Cy1-Cy2 line cross section of FIG. 17A. FIG. 17C is a Dy1-Dy2 line cross section of FIG. 17A.

As shown in FIG. 17A and FIG. 17B, the second portion p2 includes a first partial region pr1 and a second partial region pr2. The direction from the first partial region pr1 toward the second partial region pr2 is aligned with the third direction D3. For example, the first partial region pr1 is an end portion of the second portion p2 in the third direction D3. For example, the second partial region pr2 is another end portion of the second portion p2 in the third direction D3.

As shown in FIG. 16A and FIG. 16B, the fifth portion p5 includes a third partial region pr3 and a fourth partial region pr4. The direction from the third partial region pr3 toward the fourth partial region pr4 is aligned with the third direction D3. For example, the third partial region pr3 is an end portion of the fifth portion p5 in the third direction D3. For example, the fourth partial region pr4 is another end portion of the fifth portion p5 in the third direction D3.

The first element E1 further includes a first magnetic member 61, a second magnetic member 62, a third magnetic member 63, and a fourth magnetic member 64. The first magnetic member 61, the second magnetic member 62, the third magnetic member 63, and the fourth magnetic member 64 include at least one selected from the group consisting of Ir—Mn, Pt—Mn, and Ni—Mn.

The direction from the first partial region pr1 toward the first magnetic member 61, the direction from the second partial region pr2 toward the second magnetic member 62, the direction from the third partial region pr3 toward the third magnetic member 63, and the direction from the fourth partial region pr4 toward the fourth magnetic member 64 are aligned with the second direction D2.

As shown in FIG. 17B, the first element E1 includes a first film 61n and a second film 62n. The first film 61n is provided between the first partial region pr1 and the first magnetic member 61. The second film 62n is provided between the second partial region pr2 and the second magnetic member 62.

As shown in FIG. 16B, the first element E1 includes a third film 63n and a fourth film 64n. The third film 63n is provided between the third partial region pr3 and the third magnetic member 63. The fourth film 64n is provided between the fourth partial region pr4 and the fourth magnetic member 64.

The first film 61n and the second film 62n include one of a first material or a second material. The third film 63n and the fourth film 64n include the other of the first material or the second material. The first material includes at least one of Ru, Ir, or Rh. The second material includes at least one of Co, Fe, or Ni. The second material is a ferromagnetic material.

For example, when the first film 61n and the second film 62n include the first material recited above, the thicknesses of the first film 61n and the second film 62n each are, for example, about 0.8 nm (e.g., not less than 0.5 nm and not more than 1.1 nm). In such a case, for example, the first partial region pr1 and the first magnetic member 61 are magnetically coupled antiferromagnetically with each other. For example, the second partial region pr2 and the second magnetic member 62 are magnetically coupled antiferromagnetically with each other. For example, a CoFe film is provided at the interface with the first partial region pr1; and a CoFe film is provided at the interface with the first magnetic member 61. Thereby, the first partial region pr1 and the first magnetic member 61 are magnetically coupled antiferromagnetically with each other. A CoFe film is provided at the interface with the second partial region pr2; and a CoFe film is provided at the interface with the second magnetic member 62. Thereby, for example, the second partial region pr2 and the second magnetic member 62 are magnetically coupled antiferromagnetically with each other.

Figure 17D:
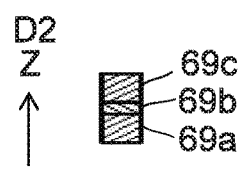

For example, the first film 61n and the second film 62n each include a first CoFe film 69a, a second CoFe film 69c, and a Ru film 69b (a film of the first material) provided between the first CoFe film 69a and the second CoFe film 69c (referring to FIG. 17D).

The first film 61n and the second film 62n are, for example, antiferromagnetically-coupled films. The third film 63n and the fourth film 64n are, for example, ferro-magnetically-coupled films. The materials of the first film 61n and the second film 62n are different from the materials of the third film 63n and the fourth film 64n.

For example, heat treatment at 250° C. to 300° C. is performed while applying a magnetic field along the third direction D3. Thereby, the magnetization of the third partial region pr3 and the magnetization of the fourth partial region pr4 are fixed by the first to fourth magnetic members 61 to 64 to the same orientation as the magnetic field of the heat treatment. The magnetization of the first partial region pr1 and the magnetization of the second partial region pr2 are fixed to the reverse orientation of the magnetic field of the heat treatment.

As a result, when there is no external magnetic field, magnetizations of reverse orientations are obtained easily in the first magnetic part 10A and the first counter magnetic part 10Ac.

As shown in FIG. 17C, for example, the third portion p3 includes a fifth partial region pr5 and a sixth partial region pr6. The direction from the fifth partial region pr5 toward the sixth partial region pr6 is aligned with the third direction D3.

As shown in FIG. 16C, for example, the sixth portion p6 includes a seventh partial region pr7 and an eighth partial region pr8. The direction from the seventh partial region pr7 toward the eighth partial region pr8 is aligned with the third direction D3.

The first element E1 further includes a fifth magnetic member 65, a sixth magnetic member 66, a seventh magnetic member 67, and an eighth magnetic member 68. The fifth magnetic member 65, the sixth magnetic member 66, the seventh magnetic member 67, and the eighth magnetic member 68 include at least one selected from the group consisting of Ir—Mn, Pt—Mn, and Ni—Mn.

As shown in FIG. 17C, the first element E1 further includes a fifth film 65n and a sixth film 66n. The fifth film 65n is provided between the fifth partial region pr5 and the fifth magnetic member 65. The sixth film 66n is provided between the sixth partial region pr6 and the sixth magnetic member 66.

As shown in FIG. 16C, the first element E1 further includes a seventh film 67n and an eighth film 68n. The seventh film 67n is provided between the seventh partial region pr7 and the seventh magnetic member 67. The eighth film 68n is provided between the eighth partial region pr8 and the eighth magnetic member 68.

The fifth film 65n and the sixth film 66n include the one of the first material or the second material recited above. The seventh film 67n and the eighth film 68n include the other of the first material or the second material recited above. The fifth film 65n and the sixth film 66n include the same material as the first film 61n and the second film 62n. The seventh film 67n and the eighth film 68n include the same material as the third film 63n and the fourth film 64n.

For example, when the fifth film 65n and the sixth film 66n include the first material recited above, the thicknesses of the fifth film 65n and the sixth film 66n each are, for example, about 0.8 nm (e.g., not less than 0.5 nm and not more than 1.1 nm). In such a case, for example, the fifth partial region pr5 and the fifth magnetic member 65 are magnetically coupled antiferromagnetically with each other. For example, the sixth partial region pr6 and the sixth magnetic member 66 are magnetically coupled antiferromagnetically with each other.

Figure 16D:
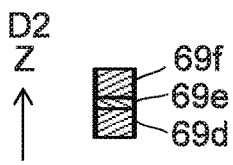

For example, as shown in FIG. 16D, the fifth film 65n and the sixth film 66n each include, for example, a first CoFe film 69d, a second CoFe film 69f, and a Ru film 69e (a film of the first material) provided between the first CoFe film 69d and the second CoFe film 69f. In such a case, the seventh film 67n and the eighth film 68n each include, for example, CoFe (the second material).

The fifth film 65n and the sixth film 66n are, for example, antiferromagnetically-coupled films. The seventh film 67n and the eighth film 68n are, for example, ferromagnetically-coupled films. The materials of the fifth film 65n and the sixth film 66n are different from the materials of the seventh film 67n and the eighth film 68n.

For example, the third film 63n, the fourth film 64n, the seventh film 67n, and the eighth film 68n each may include, for example, the first CoFe film 69d, the second CoFe film 69f, and the Ru film 69e (a film of the first material) provided between the first CoFe film 69d and the second CoFe film 69f. In such a case, the first film 61n, the second film 62n, the fifth film 65n, and the sixth film 66n each include CoFe.

By such a configuration, a stable magnetization is easier to obtain in the third portion p3; and a stable magnetization is easier to obtain in the sixth portion p6. The magnetization p6M of the sixth portion p6 easily is aligned with the reverse orientation of the magnetization p3M of the third portion p3.

Figure 18:
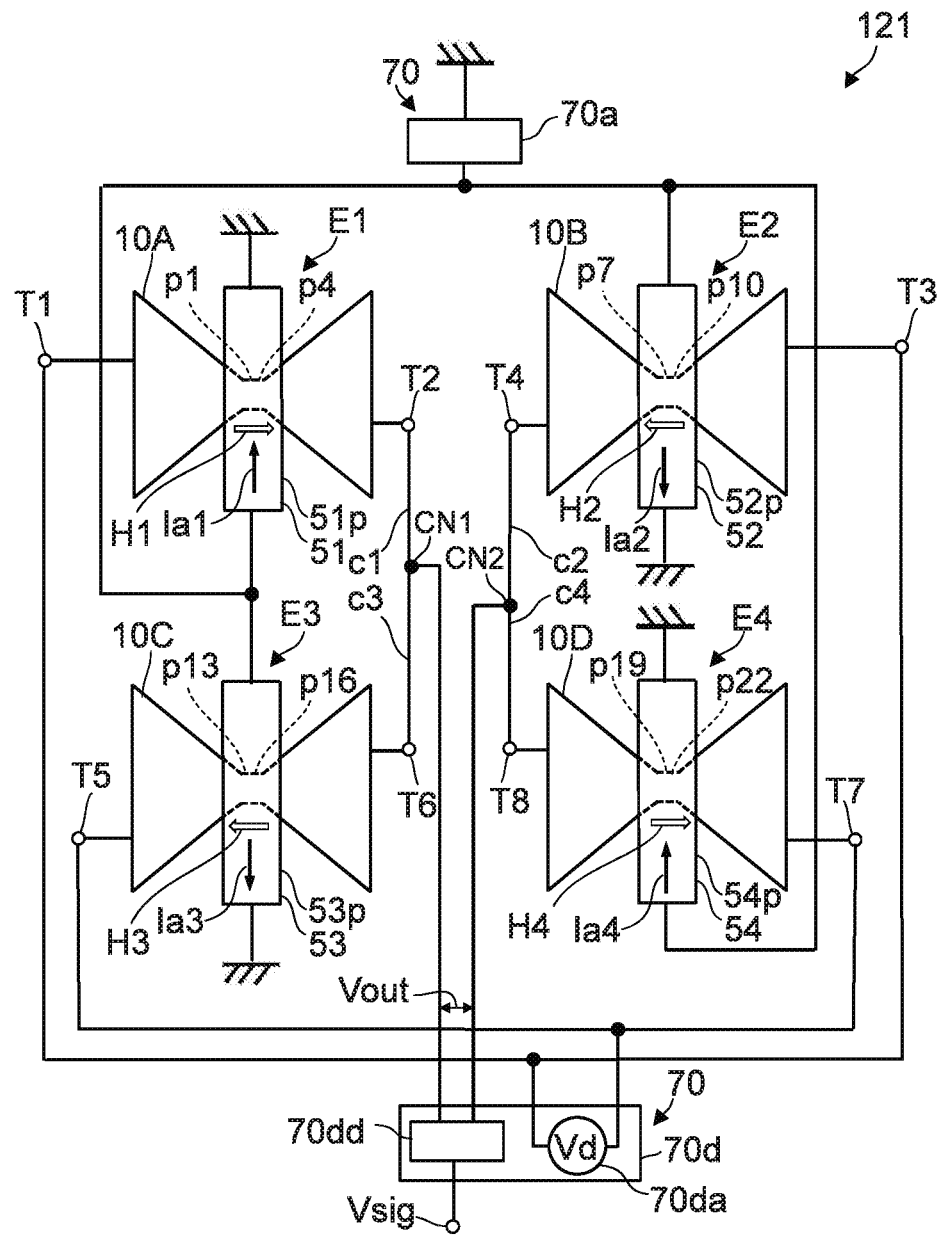
FIG. 18 is a schematic plan view illustrating a magnetic sensor according to the second embodiment.

FIG. 18 is a schematic plan view illustrating a magnetic sensor according to the second embodiment.

FIG. 19A, FIG. 19B, FIG. 20, FIG. 21A, FIG. 21B, FIG. 22, FIG. 23A, FIG. 23B, and FIG. 24 are schematic views illustrating the magnetic sensor according to the second embodiment.

Figure 19A:
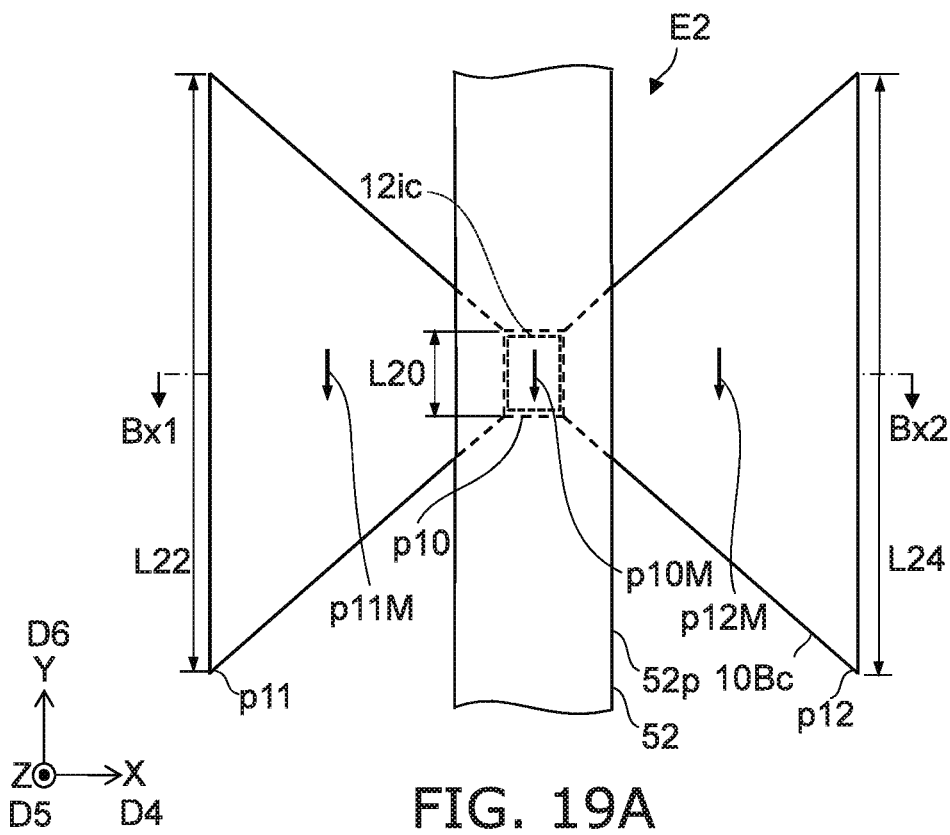
FIG. 19A and FIG. 19B are schematic views illustrating the magnetic sensor according to the second embodiment.
Figure 19B:
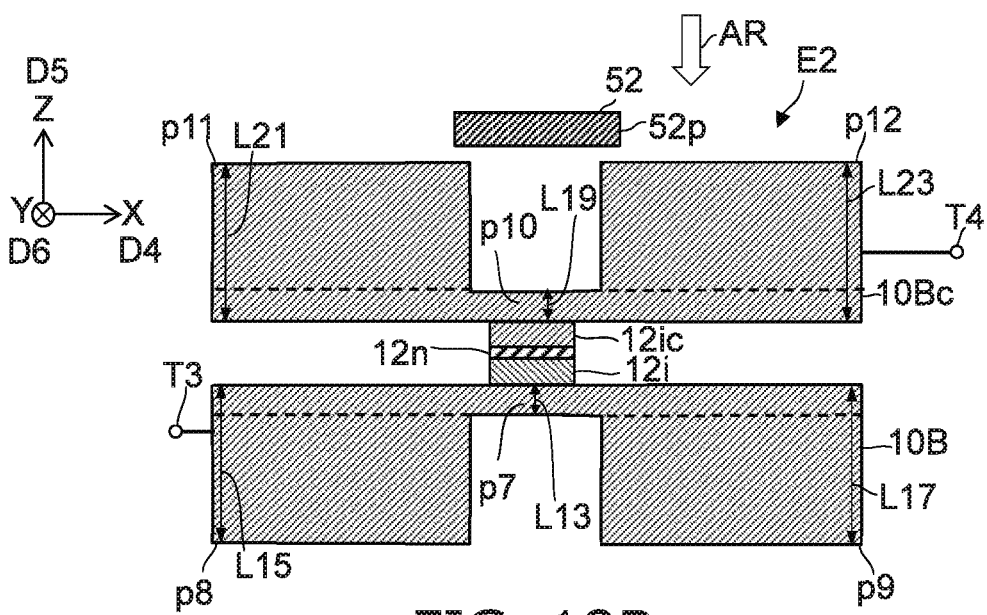
Figure 20:
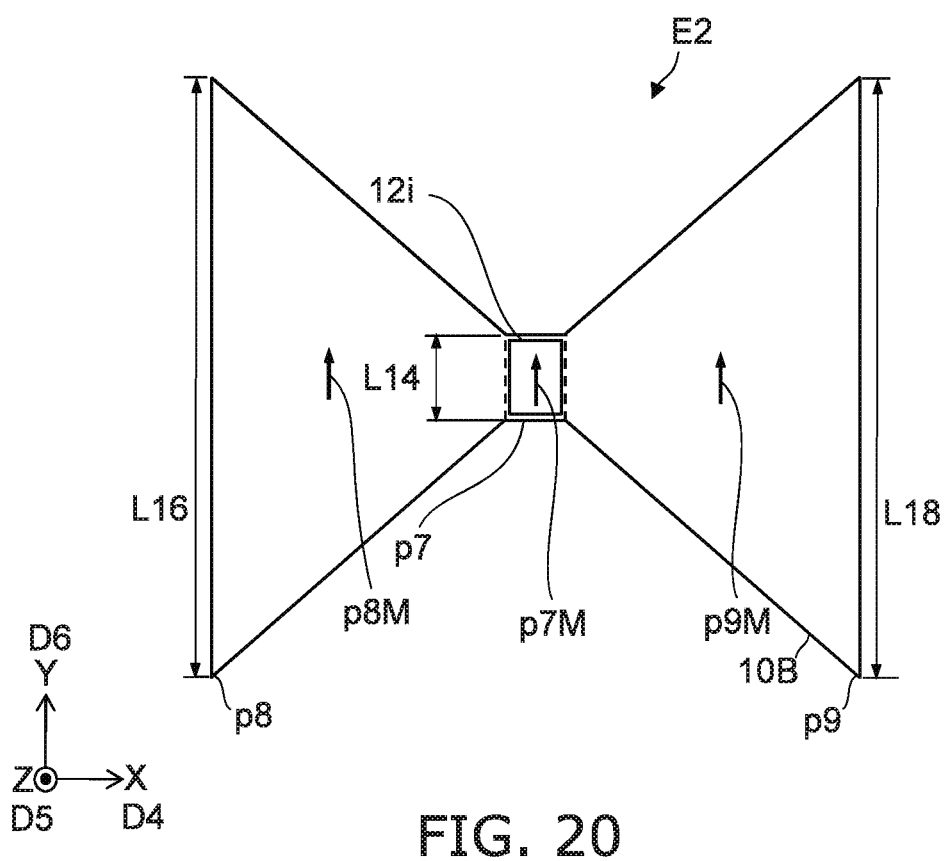
FIG. 20 is a schematic view illustrating the magnetic sensor according to the second embodiment.
Figure 21A:
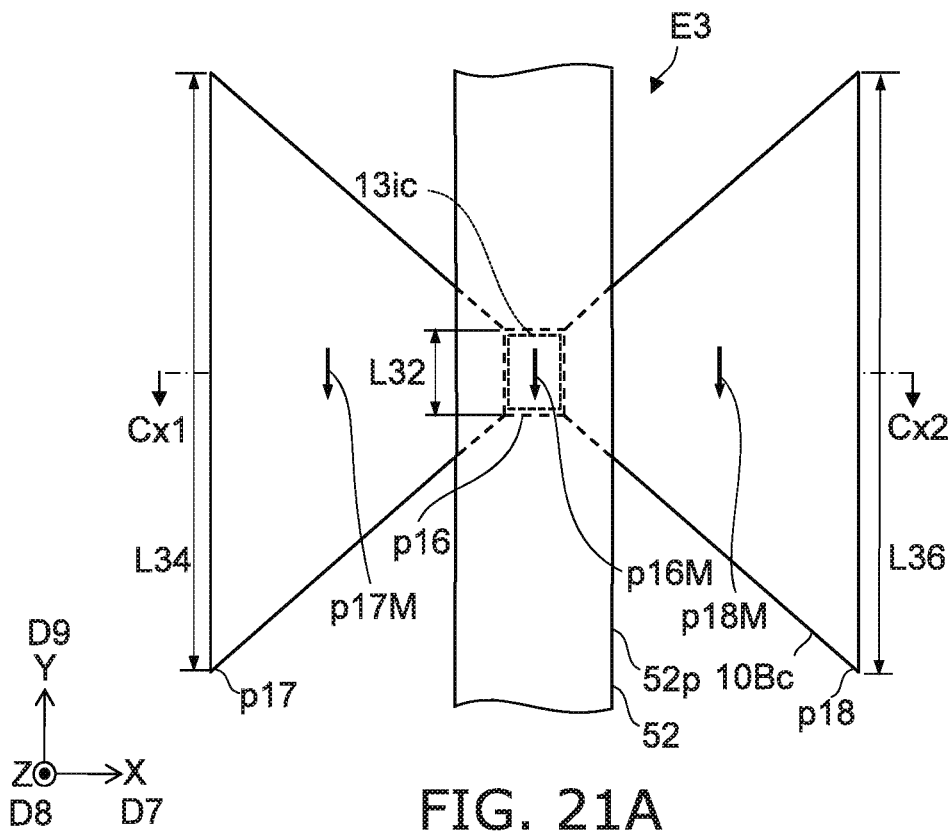
FIG. 21A and FIG. 21B are schematic views illustrating the magnetic sensor according to the second embodiment.
Figure 21B:
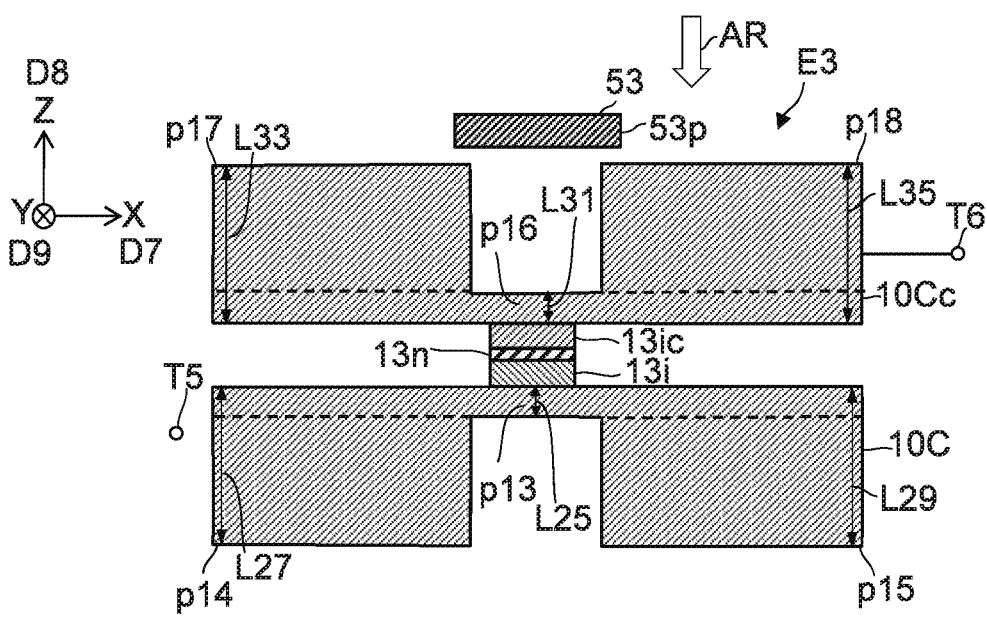
Figure 22:
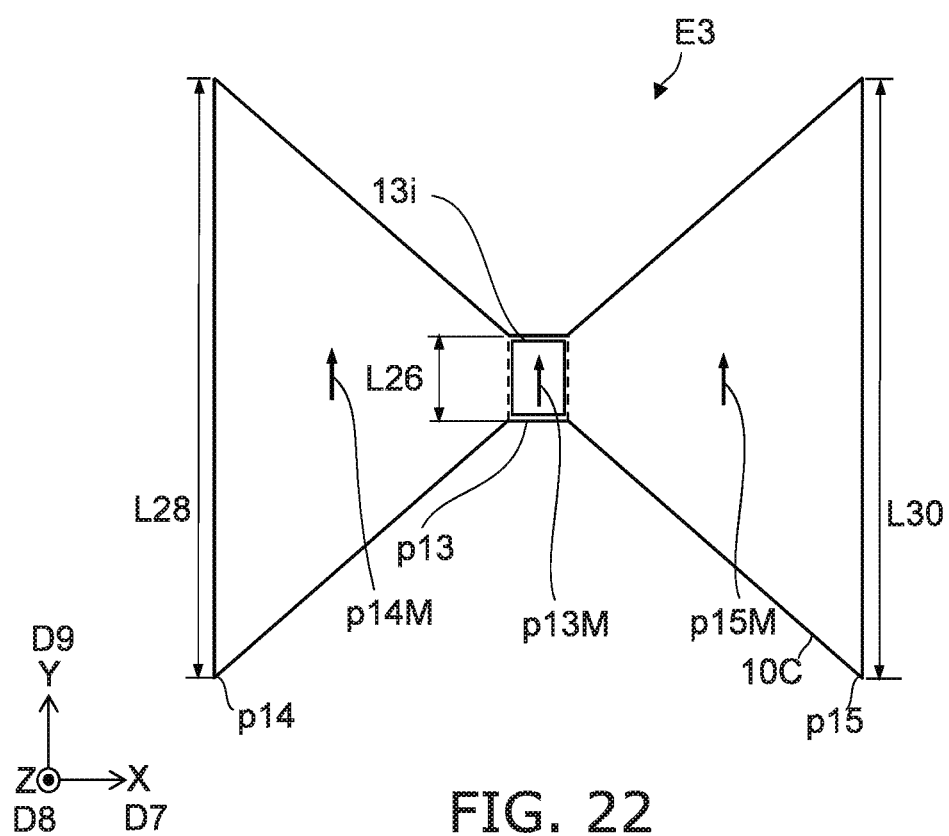
FIG. 22 is a schematic view illustrating the magnetic sensor according to the second embodiment.
Figure 23A:
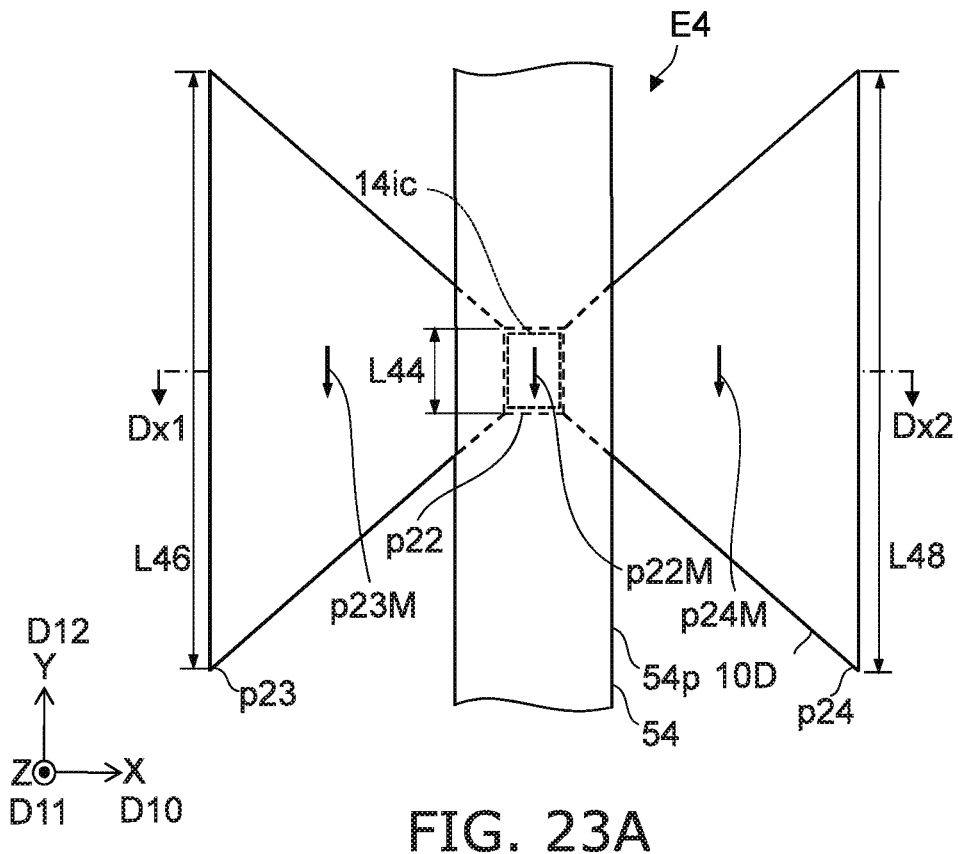
FIG. 23A and FIG. 23B are schematic views illustrating the magnetic sensor according to the second embodiment.
Figure 23B:
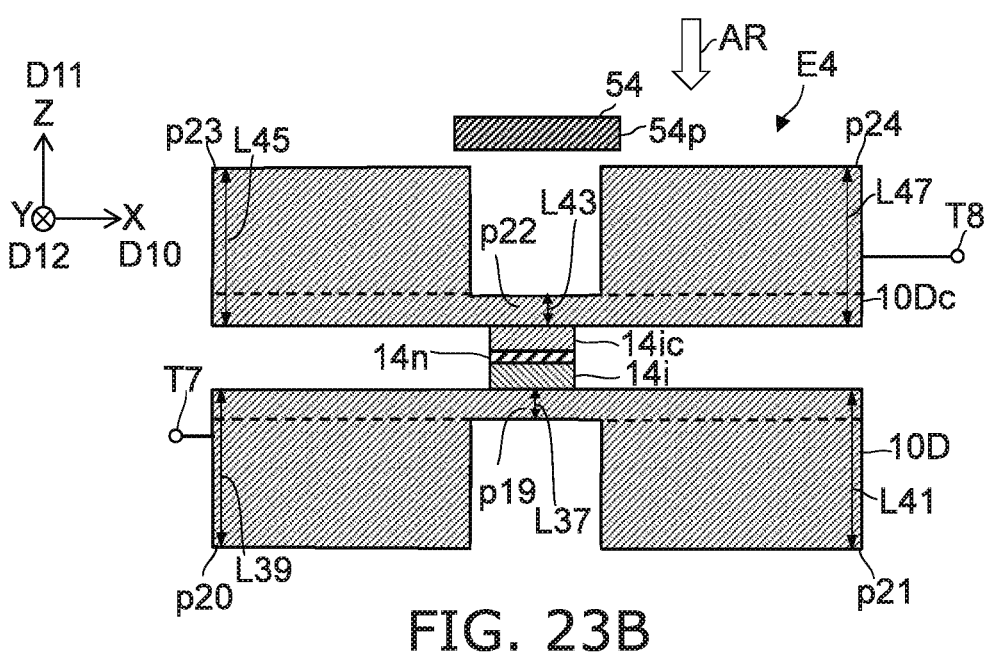
Figure 24:
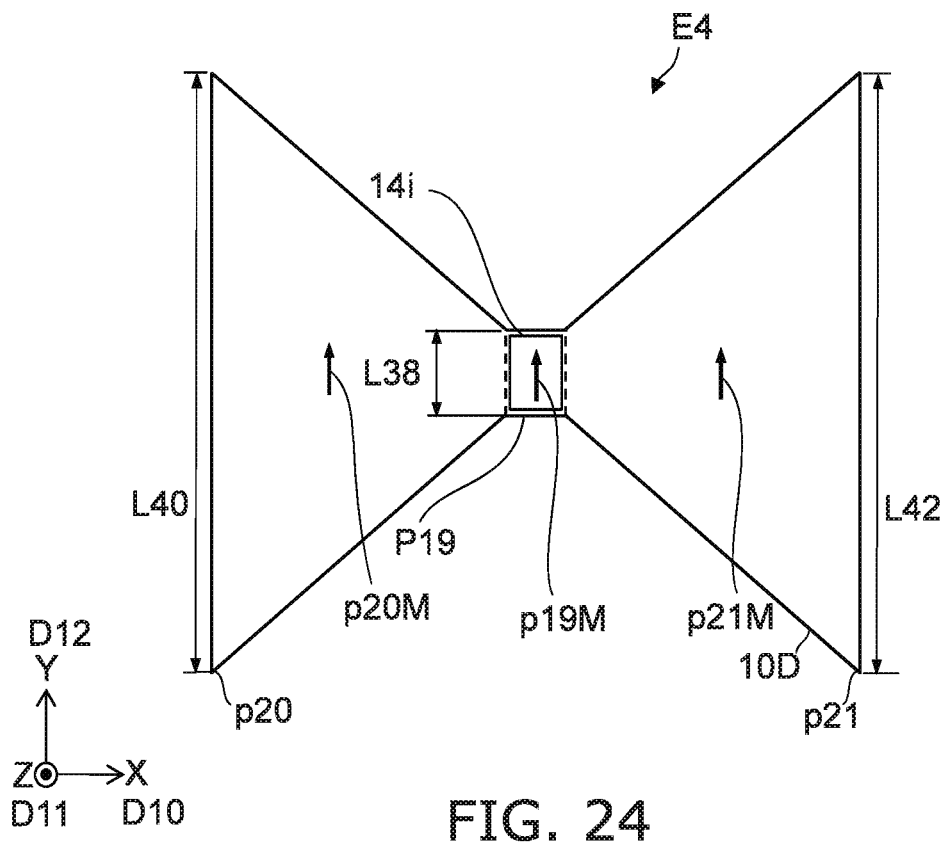
FIG. 24 is a schematic view illustrating the magnetic sensor according to the second embodiment.

FIG. 19A is a plan view as viewed along arrow AR of FIG. 19B. FIG. 19B is a Bx1-Bx2 line cross-sectional view of FIG. 19A. FIG. 20 is a plan view illustrating a portion of the magnetic sensor. FIG. 21A is a plan view as viewed along arrow AR of FIG. 21B. FIG. 21B is a Cx1-Cx2 line cross-sectional view of FIG. 21A. FIG. 22 is a plan view illustrating a portion of the magnetic sensor. FIG. 23A is a plan view as viewed along arrow AR of FIG. 23B. FIG. 23B is a Dx1-Dx2 line cross-sectional view of FIG. 23A. FIG. 24 is a plan view illustrating a portion of the magnetic sensor.

As shown in FIG. 18, the magnetic sensor 121 according to the embodiment includes the second element E2, the third element E3, and the fourth element E4 in addition to the first element E1. The magnetic sensor 121 further includes the circuit part 70. As described above, the first element E1 includes the portion 51p extending along the third direction D3. The configurations of the first element E1 described in reference to the magnetic sensors 120 and 121 are applicable to the second element E2, the third element E3, and the fourth element E4.

The magnetic sensor 121 includes, for example, the current supply circuit 70a. The current supply circuit 70a supplies the first alternating current Ia1 to the first interconnect 51. The current supply circuit 70a supplies the second alternating current Ia2 to the second interconnect 52. The current supply circuit 70a supplies the third alternating current Ia3 to the third interconnect 53.

At the same time, the orientation of the first alternating current Ia1 and the orientation of the second alternating current Ia2 are reversed. At the same time, the orientation of the first current magnetic field H1 generated by the first alternating current Ia1 and applied to the first portion p1 is the reverse of the orientation of the second current magnetic field H2 generated by the second alternating current Ia2 and applied to the fourth portion p4.

At the same time, the orientation of the third alternating current Ia3 and the orientation of the first alternating current Ia1 are reversed. At the same time, the orientation of the third current magnetic field H3 generated by the third alternating current Ia3 and applied to the seventh portion p7 is the reverse of the orientation of the first current magnetic field H1 generated by the first alternating current Ia1 and applied to the first portion p1.

At the same time, the orientation of the fourth alternating current Ia4 and the orientation of the first alternating current Ia1 are the same. At the same time, the orientation of the fourth current magnetic field H4 generated by the fourth alternating current Ia4 and applied to the tenth portion p10 is the same as the orientation of the first current magnetic field H1 generated by the first alternating current Ia1 and applied to the first portion p1.

For example, the second element E2 includes the second magnetic part 10B, a second counter magnetic part 10Bc, the second nonmagnetic portion 12n, the second intermediate magnetic layer 12i, a second counter intermediate magnetic layer 12ic, and the second interconnect 52.

The second magnetic part 10B includes the seventh portion p7, the eighth portion p8, and the ninth portion p9. The direction from the eighth portion p8 toward the ninth portion p9 is aligned with the fourth direction D4. The seventh portion p7 is between the eighth portion p8 and the ninth portion p9 in the fourth direction D4. The seventh portion p7 has the thirteenth length L13 along the fifth direction D5 crossing the fourth direction D4, and the fourteenth length L14 along the sixth direction D6 crossing a plane including the fourth direction D4 and the fifth direction D5.

The eighth portion p8 has at least one of the fifteenth length L15 along the fifth direction D5 that is longer than the thirteenth length L13, or the sixteenth length L16 along the sixth direction D6 that is longer than the fourteenth length L14. The ninth portion p9 has at least one of the seventeenth length L17 along the fifth direction D5 that is longer than the thirteenth length L13, or the eighteenth length L18 along the sixth direction D6 that is longer than the fourteenth length L14. For example, the fourth direction D4 is aligned with the first direction D1; the fifth direction D5 is aligned with the second direction D2; and the sixth direction D6 is aligned with the third direction D3.

The second counter magnetic part 10Bc includes the tenth portion p10, the eleventh portion p11, and the twelfth portion p12. The direction from the seventh portion p7 toward the tenth portion p10 is aligned with the fifth direction D5. The direction from the eighth portion p8 toward the eleventh portion p11 is aligned with the fifth direction D5. The direction from the ninth portion p9 toward the twelfth portion p12 is aligned with the fifth direction D5. The tenth portion p10 is between the eleventh portion p11 and the twelfth portion p12 in the fourth direction D4.

The tenth portion p10 has the nineteenth length L19 along the fifth direction D5 and the twentieth length L20 along the sixth direction D6. The eleventh portion p11 has at least one of the twenty-first length L21 along the fifth direction D5 that is longer than the nineteenth length L19, or the twenty-second length L22 along the sixth direction D6 that is longer than the twentieth length L20. The twelfth portion p12 has at least one of the twenty-third length L23 along the fifth direction D5 that is longer than the nineteenth length L19, or the twenty-fourth length L24 along the sixth direction D6 that is longer than the twentieth length L20.

The second nonmagnetic portion 12n is provided between the seventh portion p7 and the tenth portion p10. The second intermediate magnetic layer 12i is provided between the seventh portion p7 and the second nonmagnetic portion 12n. The second counter intermediate magnetic layer 12ic is provided between the second nonmagnetic portion 12n and the tenth portion p10. The second interconnect 52 includes the portion 52p extending along the sixth direction D6. For example, at least a portion of the second interconnect 52 overlaps at least a portion of the seventh portion p7 in the fifth direction D5. At least a portion of the second interconnect 52 overlaps at least a portion of the tenth portion p10 in the fifth direction D5.

For example, a magnetization p7M of the seventh portion p7 is aligned with the orientation of the magnetization p8M of the eighth portion p8 and the orientation of the magnetization p9M of the ninth portion p9. For example, a magnetization p10M of the tenth portion p10 is aligned with the orientation of the magnetization p11M of the eleventh portion p11 and the orientation of the magnetization p12M of the twelfth portion p12.

For example, the magnetization p11M of the eleventh portion p11 is aligned with the reverse orientation of the magnetization p8M of the eighth portion p8. The magnetization p12M of the twelfth portion p12 is aligned with the reverse orientation of the magnetization p9M of the ninth portion p9.

The third element E3 includes the third magnetic part 10C, a third counter magnetic part 10Cc, the third nonmagnetic portion 13n, the third intermediate magnetic layer 13i, a third counter intermediate magnetic layer 13ic, and the third interconnect 53.

The third magnetic part 10C includes a thirteenth portion p13, a fourteenth portion p14, and a fifteenth portion p15. The direction from the fourteenth portion p14 toward the fifteenth portion p15 is aligned with the seventh direction D7. The thirteenth portion p13 is between the fourteenth portion p14 and the fifteenth portion p15 in the seventh direction D7.

The thirteenth portion p13 has a twenty-fifth length L25 along the eighth direction D8 crossing the seventh direction D7, and a twenty-sixth length L26 along the ninth direction D9 crossing a plane including the seventh direction D7 and the eighth direction D8.

The fourteenth portion p14 has at least one of a twenty-seventh length L27 along the eighth direction D8 that is longer than the twenty-fifth length L25, or a twenty-eighth length L28 along the ninth direction D9 that is longer than the twenty-sixth length L26. The fifteenth portion p15 has at least one of a twenty-ninth length L29 along the eighth direction D8 that is longer than the twenty-fifth length L25, or a thirtieth length L30 along the ninth direction D9 that is longer than the twenty-sixth length L26. For example, the seventh direction D7 is aligned with the first direction D1; the eighth direction D8 is aligned with the second direction D2; and the ninth direction D9 is aligned with the third direction D3.

The third counter magnetic part 10Cc includes a sixteenth portion p16, a seventeenth portion p17, and an eighteenth portion p18. The direction from the thirteenth portion p13 toward the sixteenth portion p16 is aligned with the eighth direction D8. The direction from the fourteenth portion p14 toward the seventeenth portion p17 is aligned with the eighth direction D8. The direction from the fifteenth portion p15 toward the eighteenth portion p18 is aligned with the eighth direction D8. The sixteenth portion p16 is between the seventeenth portion p17 and the eighteenth portion p18 in the seventh direction D7.

The sixteenth portion p16 has a thirty-first length L31 along the eighth direction D8 and a thirty-second length L32 along the ninth direction D9. The seventeenth portion p17 has at least one of a thirty-third length L33 along the eighth direction D8 that is longer than the thirty-first length L31, or a thirty-fourth length L34 along the ninth direction D9 that is longer than the thirty-second length L32. The eighteenth portion p18 has at least one of a thirty-fifth length L35 along the eighth direction D8 that is longer than the thirty-first length L31, or a thirty-sixth length L36 along the ninth direction D9 that is longer than the thirty-second length L32.

The third nonmagnetic portion 13n is provided between the thirteenth portion p13 and the sixteenth portion p16. The third intermediate magnetic layer 13i is provided between the thirteenth portion p13 and the third nonmagnetic portion 13n. The third counter intermediate magnetic layer 13ic is provided between the third nonmagnetic portion 13n and the sixteenth portion p16. The third interconnect 53 includes the portion 53p extending along the ninth direction D9. For example, at least a portion of the third interconnect 53 overlaps at least a portion of the thirteenth portion p13 in the eighth direction D8. At least a portion of the third interconnect 53 overlaps at least a portion of the sixteenth portion p16 in the eighth direction D8.

For example, a magnetization p13M of the thirteenth portion p13 is aligned with the orientation of a magnetization p14M of the fourteenth portion p14 and the orientation of a magnetization p15M of the fifteenth portion p15. For example, a magnetization p16M of the sixteenth portion p16 is aligned with the orientation of a magnetization p17M of the seventeenth portion p17 and the orientation of a magnetization p18M of the eighteenth portion p18.

For example, the magnetization p17M of the seventeenth portion p17 is aligned with the reverse orientation of the magnetization p14M of the fourteenth portion p14. The magnetization p18M of the eighteenth portion p18 is aligned with the reverse orientation of the magnetization p15M of the fifteenth portion p15.

The fourth element E4 includes the fourth magnetic part 10D, a fourth counter magnetic part 10Dc, the fourth nonmagnetic portion 14n, the fourth intermediate magnetic layer 14i, a fourth counter intermediate magnetic layer 14ic, and the fourth interconnect 54.

The fourth magnetic part 10D includes a nineteenth portion p19, a twentieth portion p20, and a twenty-first portion p21. The direction from the twentieth portion p20 toward the twenty-first portion p21 is aligned with the tenth direction D10. The nineteenth portion p19 is between the twentieth portion p20 and the twenty-first portion p21 in the tenth direction D10. The nineteenth portion p19 has a thirty-seventh length L37 along the eleventh direction D11 crossing the tenth direction D10, and a thirty-eighth length L38 along the twelfth direction D12 crossing a plane including the tenth direction D10 and the eleventh direction D11. For example, the tenth direction D10 is aligned with the first direction D1; the eleventh direction D11 is aligned with the second direction D2; and the twelfth direction D12 is aligned with the third direction D3.

The twentieth portion p20 has at least one of a thirty-ninth length L39 along the eleventh direction D11 that is longer than the thirty-seventh length L37, or a fortieth length L40 along the twelfth direction D12 that is longer than the thirty-eighth length L38. The twenty-first portion p21 has at least one of a forty-first length L41 along the eleventh direction D11 that is longer than the thirty-seventh length L37, or a forty-second length L42 along the twelfth direction D12 that is longer than the thirty-eighth length L38.

The fourth counter magnetic part 10Dc includes a twenty-second portion p22, a twenty-third portion p23, and a twenty-fourth portion p24. The direction from the nineteenth portion p19 toward the twenty-second portion p22 is aligned with the eleventh direction D11. The direction from the twentieth portion p20 toward the twenty-third portion p23 is aligned with the eleventh direction D11. The direction from the twenty-first portion p21 toward the twenty-fourth portion p24 is aligned with the eleventh direction D11. The twenty-second portion p22 is between the twenty-third portion p23 and the twenty-fourth portion p24 in the tenth direction D10.

The twenty-second portion p22 has a forty-third length L43 along the eleventh direction D11 and a forty-fourth length L44 along the twelfth direction D12. The twenty-third portion p23 has at least one of a forty-fifth length L45 along the eleventh direction D11 that is longer than the forty-third length L43, or a forty-sixth length L46 along the twelfth direction D12 that is longer than the forty-fourth length L44. The twenty-fourth portion p24 has at least one of a forty-seventh length L47 along the eleventh direction D11 that is longer than the forty-third length L43, or a forty-eighth length L48 along the twelfth direction D12 that is longer than the forty-fourth length L44.

The fourth nonmagnetic portion 14n is provided between the nineteenth portion p19 and the twenty-second portion p22. The fourth intermediate magnetic layer 14i is provided between the nineteenth portion p19 and the fourth nonmagnetic portion 14n. The fourth counter intermediate magnetic layer 14ic is provided between the fourth nonmagnetic portion 14n and the twenty-second portion p22. The fourth interconnect 54 includes the portion 54p extending along the twelfth direction D12. For example, at least a portion of the fourth interconnect 54 overlaps at least a portion of the nineteenth portion p19 in the eleventh direction D11. At least a portion of the fourth interconnect 54 overlaps at least a portion of the twenty-second portion p22 in the eleventh direction D11.

For example, a magnetization p19M of the nineteenth portion p19 is aligned with the orientation of a magnetization p20M of the twentieth portion p20 and the orientation of a magnetization p21M of the twenty-first portion p21. For example, a magnetization p22M of the twenty-second portion p22 is aligned with the orientation of a magnetization p23M of the twenty-third portion p23 and the orientation of a magnetization p24M of the twenty-fourth portion p24.

For example, the magnetization p23M of the twenty-third portion p23 is aligned with the reverse orientation of the magnetization p20M of the twentieth portion p20. The magnetization p24M of the twenty-fourth portion p24 is aligned with the reverse orientation of the magnetization p21M of the twenty-first portion p21.

For example, the third terminal T3 is electrically connected to the second magnetic part 10B. The fourth terminal T4 is electrically connected to the second counter magnetic part 10Bc. The electrical resistance between the second magnetic part 10B and the second counter magnetic part 10Bc corresponds to the electrical resistance between the third terminal T3 and the fourth terminal T4.

For example, the fifth terminal T5 is electrically connected to the third magnetic part 10C. The sixth terminal T6 is electrically connected to the third counter magnetic part 10Cc. The electrical resistance between the third magnetic part 10C and the third counter magnetic part 10Cc corresponds to the electrical resistance between the fifth terminal T5 and the sixth terminal T6.

For example, the seventh terminal T7 is electrically connected to the fourth magnetic part 10D. The eighth terminal T8 is electrically connected to the fourth counter magnetic part 10Dc. The electrical resistance between the fourth magnetic part 10D and the fourth counter magnetic part 10Dc corresponds to the electrical resistance between the seventh terminal T7 and the eighth terminal T8.

The bias voltage Vb is applied to the first to fourth elements E1 to E4 by the bias voltage application part 70da. The first element E1 and the third element E3 are connected in series by a current path including the second terminal T2, the first terminal T1, the fifth terminal T5, and the sixth terminal T6. The second element E2 and the fourth element E4 are connected in series by a current path including the fourth terminal T4, the third terminal T3, the seventh terminal T7, and the eighth terminal T8. For example, the bias voltage application part 70da supplies a direct current to the current path of the first element E1 and the third element E3 and the current path of the second element E2 and the fourth element E4.

For example, the detector 70dd detects, as the signal Vsig, the potential difference Vout between an intermediate portion (the first connection point CN1) of the first terminal T1 and the fifth terminal T5 and an intermediate portion (the second connection point CN2) of the third terminal T3 and the seventh terminal T7. When the signal magnetic field Hsig is zero, the resistances of the first to fourth elements E1 to E4 are the same resistance. At this time, a potential is not generated between the first connection point CN1 and the second connection point CN2. When the signal magnetic field Hsig is applied, the same resistance fluctuation occurs in the first element E1 and the fourth element E4. The same resistance fluctuation occurs in the second element E2 and the third element E3. The resistance fluctuation of the first element E1 and the fourth element E4 and the resistance fluctuation of the second element E2 and the third element E3 are the reverse of each other. The potential difference Vout is generated thereby.

As shown in FIG. 18, for example, the circuit part 70 includes the current supply circuit 70a. The current supply circuit 70a is configured to supply the first alternating current Ia1 to the first interconnect 51. The current supply circuit 70a is configured to supply the second alternating current Ia2 to the second interconnect 52. The current supply circuit 70a is configured to supply the third alternating current Ia3 to the third interconnect 53. The current supply circuit 70a is configured to supply the fourth alternating current Ia4 to the fourth interconnect 54.

The orientation of the first current magnetic field H1 generated by the first alternating current Ia1 and applied to the first portion p1 has a reverse component of the orientation of the second current magnetic field H2 generated by the second alternating current Ia2 and applied to the seventh portion p7. The orientation of the first current magnetic field H1 has a reverse component of the orientation of the third current magnetic field H3 generated by the third alternating current Ia3 and applied to the thirteenth portion p13. The orientation of the fourth current magnetic field H4 generated by the fourth alternating current Ia4 and applied to the nineteenth portion p19 has the reverse component of the orientation of the second current magnetic field H2. The orientation of the fourth current magnetic field H4 has a reverse component of the orientation of the third current magnetic field H3. The effects of the noise can be suppressed by using such an alternating current and by using a bridge circuit such as that shown in FIG. 18.

As shown in FIG. 18, a bridge circuit is formed of the first to fourth elements E1 to E4. For example, the circuit part 70 includes the detection circuit 70d. For example, the detection circuit 70d is electrically connected to the first connection point CN1 and the second connection point CN2. The detection circuit 70d outputs the signal Vsig corresponding to the potential difference Vout between the first connection point CN1 and the second connection point CN2. At the first connection point CN1, the first current path c1 which includes the first magnetic part 10A and the first magnetic layer 11L and the third current path c3 which includes the third magnetic part 10C and the third magnetic layer 13L are electrically connected to each other in series. At the second connection point CN2, the second current path c2 which includes the second magnetic part 10B and the second magnetic layer 12L and the fourth current path c4 which includes the fourth magnetic part 10D and the fourth magnetic layer 14L are electrically connected to each other in series.

In the first embodiment and the second embodiment, for example, at least one of the first to fourth nonmagnetic portions 11n to 14n includes magnesium and oxygen. For example, at least one of the first to fourth nonmagnetic portions 11n to 14n includes MgO. For example, a high MR ratio is obtained; and high sensitivity is obtained.

An example of simulation results of characteristics of the magnetic sensor 121 will now be described.

In the simulation, the sensor has the bridge configuration illustrated in FIG. 8. One element has the configuration of the eighth model MD8 illustrated in FIG. 2. The gain G of the eighth model MD8 is 103. The values of the alternating currents supplied to the first to fourth interconnects 51 to 54 are set to values corresponding to the external magnetic field Hex at which the maximum slope is obtained in the R-H characteristic illustrated in FIG. 15. A frequency f of the alternating current is 1 MHz. The magnetoresistance change rate ($\Delta R/R$) is 200% for each of the first to fourth elements E1 to E4. A saturation magnetic field Hs is 0.5 mT for each of the first to fourth magnetic parts 10A to 10D. The bias voltage Vb is 0.5 V.

For each of the first to fourth magnetic layers 11L to 14L, the length in the X-axis direction is 15 μm; and the length in the Y-axis direction is 20 μm. The major noise generated in the sensor is the 1/f noise; and the other noise is sufficiently small. The Hooge constant α of the 1/f noise is $2\times10^{-9}$ m². The 1/f noise Vn and the signal Vsig obtained as the output are obtained by the following formulas.

$$Vsig = 2 \times Vb \times G \times (\Delta R/R)/Hs$$

$$Vn = (\alpha \times Vd \times Vd/A/f)^{1/2}$$

In the formulas recited above, "A" is the surface area in the X-Y plane of each of the first to fourth stacked bodies SB1 to SB4 and is 18×18 μm². As a result of the simulation, a signal Vsig of 0.2 μV/pT is obtained; and the 1/f noise Vn of 0.08 μV/(Hz)$^{1/2}$ is obtained. The minimum detected magnetic field at which the SN ratio is 1 is 0.4 pT. Thus, according to the embodiment, it is possible to detect a micro magnetic field of 1 pT or less.

An example of an application of the magnetic sensor according to the embodiment will now be described.

Figure 25:
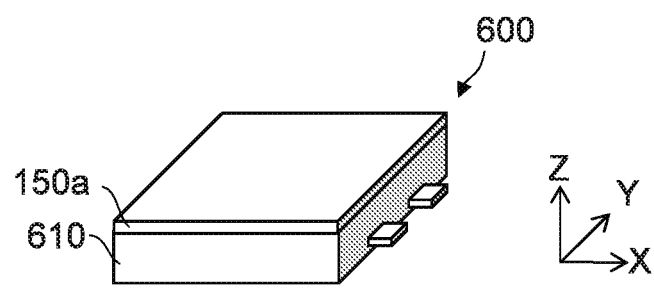
FIG. 25 is a schematic perspective view showing an application example of the magnetic sensor according to the embodiment.

FIG. 25 is a schematic perspective view showing an application example of the magnetic sensor according to the embodiment.

Figure 26:
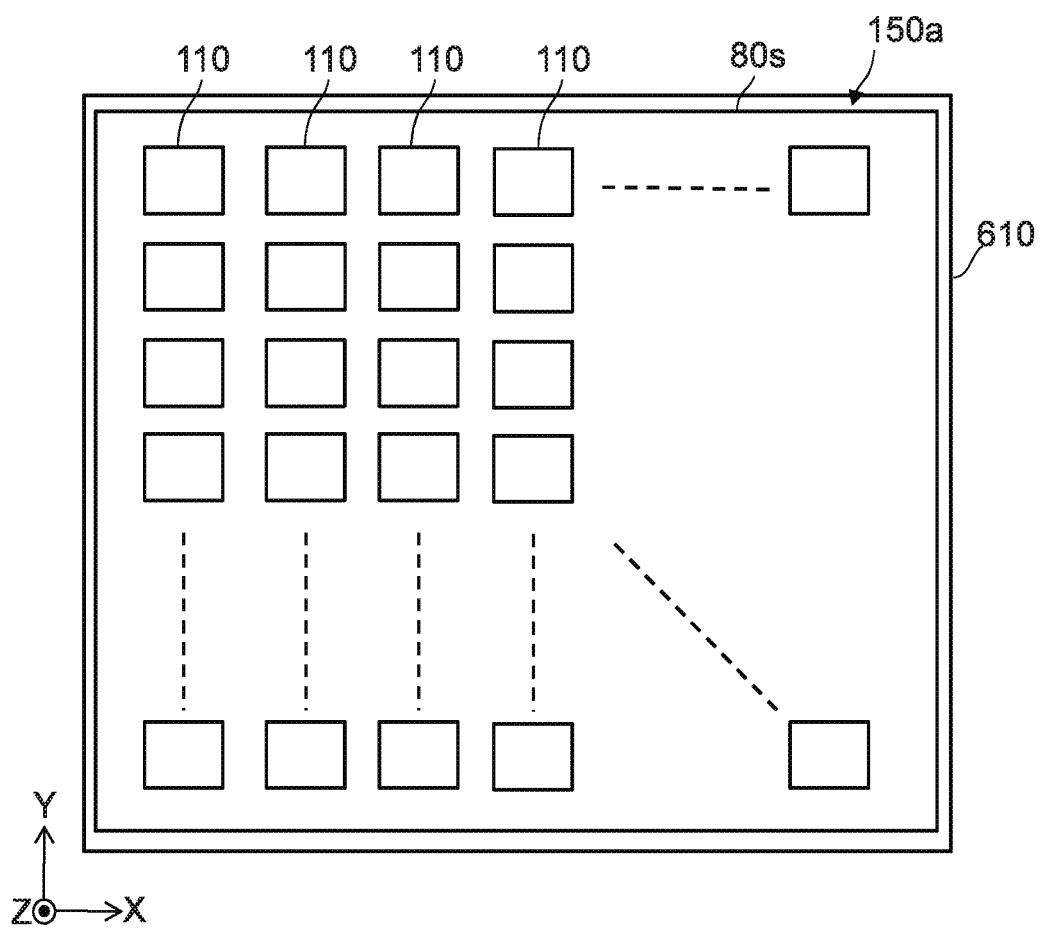
FIG. 26 is a schematic plan view showing the application example of the magnetic sensor according to the embodiment.

FIG. 26 is a schematic plan view showing the application example of the magnetic sensor according to the embodiment.

As shown in FIG. 25 and FIG. 26, the magnetic sensor 150a according to the embodiment may be used with a battery 610. For example, a battery system 600 includes the battery 610 and the magnetic sensor 150a. The magnetic sensor 150a can detect a magnetic field generated by a current flowing in the battery 610.

For example, as shown in FIG. 26, the magnetic sensor 150a includes multiple magnetic sensors according to the embodiment. In the example, the magnetic sensor 150a includes the multiple magnetic sensors 110 (or 110A, 110B, 110a, 110b, 111, 120, 121, etc.). For example, the multiple magnetic sensors are arranged in two directions (e.g., the X-axis direction and the Y-axis direction). For example, the multiple magnetic sensors 110 are provided on a substrate 80s.

The magnetic sensor 150a can detect the magnetic field generated by the current flowing in the battery 610. For example, there are cases where an abnormal current flows in the battery 610 when the battery 610 approaches an abnormal state. The change of the state of the battery 610 can be known by the magnetic sensor 150a detecting the abnormal current. For example, the entire battery 610 can be inspected in a short period of time by using bidirectional sensor group drive means in a state in which the magnetic sensor 150a is placed proximally to the battery 610. The magnetic sensor 150a may be used to inspect the battery 610 in the manufacturing of the battery 610.

For example, the magnetic sensor according to the embodiment is applicable to a diagnostic device, etc. An example of a diagnostic device using the magnetic sensor according to the embodiment will now be described.

Third Embodiment

Figure 27:
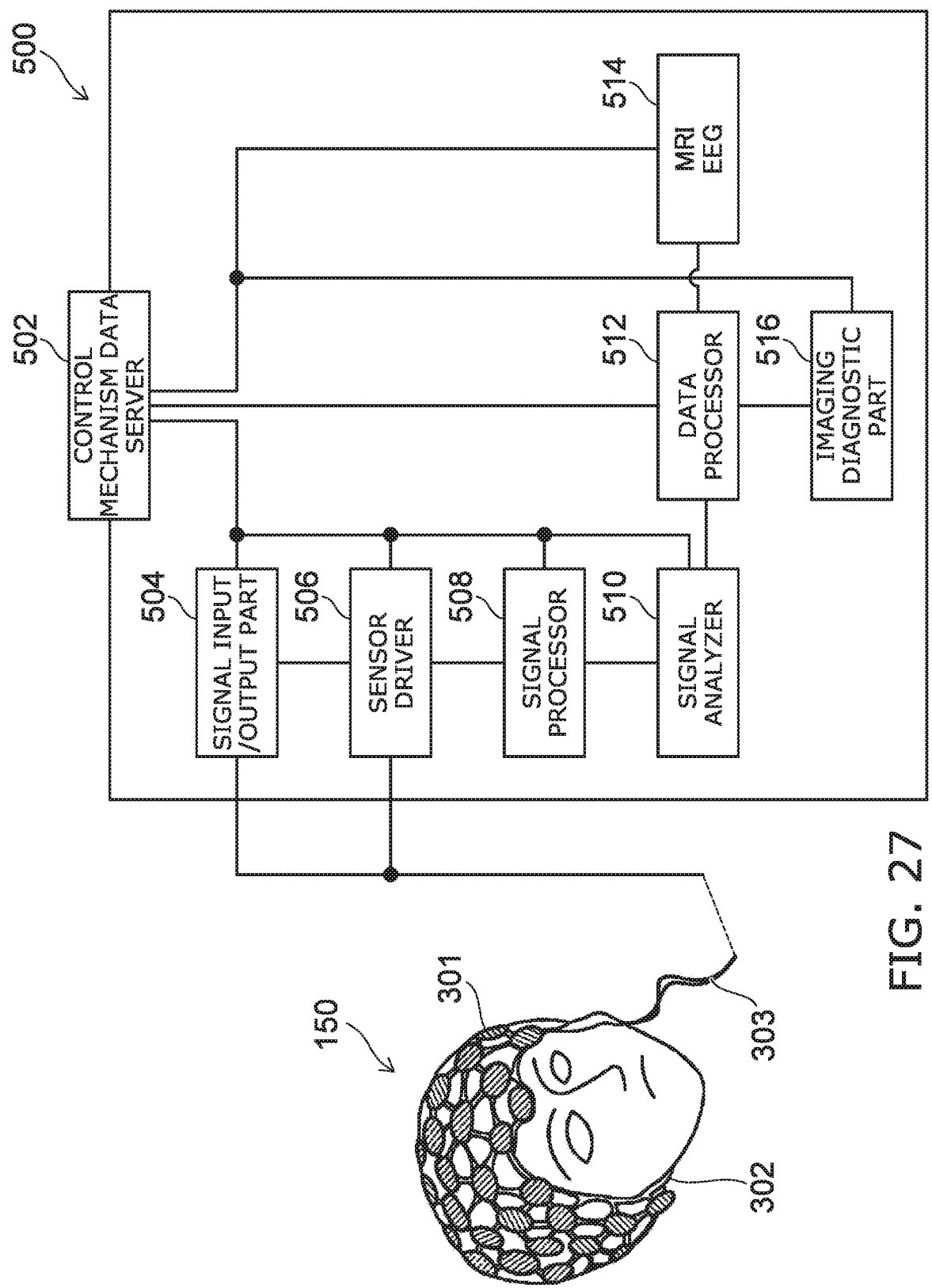
FIG. 27 is a schematic view showing a magnetic sensor and a diagnostic device according to a third embodiment.

FIG. 27 is a schematic view showing a magnetic sensor and a diagnostic device according to a third embodiment.

As shown in FIG. 27, the diagnostic device 500 includes the magnetic sensor 150. The magnetic sensor 150 includes the magnetic sensors (and the magnetic sensor devices) described in reference to the first embodiment and the second embodiment and modifications of the magnetic sensors (and the magnetic sensor devices).

In the diagnostic device 500, the magnetic sensor 150 is, for example, a magnetoencephalograph device. The magnetoencephalograph device detects a magnetic field generated by cranial nerves. In the case where the magnetic sensor 150 is included in a magnetoencephalograph device, the size of the magnetic element included in the magnetic sensor 150 is, for example, not less than 1 mm but less than 10 mm. The size is, for example, the length including the MFC.

As shown in FIG. 27, the magnetic sensor 150 (the magnetoencephalograph device) is mounted to, for example, the head of a human body. The magnetic sensor 150 (the magnetoencephalograph device) includes a sensor part 301 (a first sensor part SU1 or the like). The magnetic sensor 150 (the magnetoencephalograph device) may include multiple sensor parts 301 (the first sensor part SU1, a second sensor part SU2, etc.). The number of the multiple sensor parts 301 is, for example, about 100 (e.g., not less than 50 and not more than 150). The multiple sensor parts 301 are provided in a base body 302 that is pliable.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 (the magnetic sensors described in reference to the first embodiment and the second embodiment) is small compared to the size of a conventional SQUID magnetic sensor. Therefore, the mounting of the multiple sensor parts 301 is easy. The mounting of the multiple sensor parts 301 and the other circuits is easy. It is easy for the multiple sensor parts 301 to coexist with the other sensors.

The base body 302 may include, for example, an elastic body such as a silicone resin, etc. For example, the multiple sensor parts 301 are linked to each other and provided in the base body 302. For example, the base body 302 can be closely adhered to the head.

An input/output cord 303 of the sensor part 301 is connected to a sensor driver 506 and a signal input/output part 504 of the diagnostic device 500. Magnetic field measurement is performed in the sensor part 301 based on the electrical power from the sensor driver 506 and the control signal from the signal input/output part 504. The result is input to the signal input/output part 504. The signal that is obtained by the signal input/output part 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis to match the signal phases is performed in the signal analyzer 510.

The output of the signal analyzer 510 (the data for which the signal analysis has ended) is supplied to a data processor 512. Data analysis is performed in the data processor 512. It is possible to include image data such as, for example, MRI (Magnetic Resonance Imaging), etc., in the data analysis. It is possible to include, for example, scalp potential information such as an EEG (Electroencephalogram), etc., in the data analysis. For example, nerve firing point analysis, inverse analysis, or the like is performed by the data analysis.

For example, the result of the data analysis is supplied to an imaging diagnostic part 516. Imaging is performed by the imaging diagnostic part 516. The diagnosis is supported by the imaging.

For example, the series of operations recited above is controlled by a control mechanism 502. For example, necessary data such as preliminary signal data, metadata partway through the data processing, or the like is stored in a data server. The data server and the control mechanism may be integrated.

The diagnostic device 500 according to the embodiment includes the magnetic sensor 150, and a processor that processes the output signal obtained from the magnetic sensor 150. The processor includes, for example, at least one of the signal processor 508 or the data processor 512. The processor includes, for example, a computer, etc.

In the magnetic sensor 150 shown in FIG. 27, the sensor part 301 is mounted to the head of a human body. The sensor part 301 may be mounted to the chest of the human body. Magnetocardiography is possible thereby. For example, the sensor part 301 may be mounted to the abdomen of a pregnant woman. Palmoscopy of the fetus can be performed thereby.

It is favorable for the magnetic sensor device including the participant to be mounted inside a shielded room. For example, the effects of geomagnetism or magnetic noise can be suppressed thereby.

For example, a mechanism may be provided to locally shield the sensor part 301 or the measurement section of the human body. For example, a shield mechanism may be provided in the sensor part 301. For example, the signal analysis or the data processing may be effectively shielded.

In the embodiment, the base body 302 may be pliable or substantially may not be pliable. In the example shown in FIG. 27, the base body 302 is a continuous film that is patterned into a hat-like configuration. The base body 302 may have a net configuration. For example, good wearability is obtained thereby. For example, the adhesion of the base body 302 with the human body improves. The base body 302 may have a hard helmet-like configuration.

Figure 28:
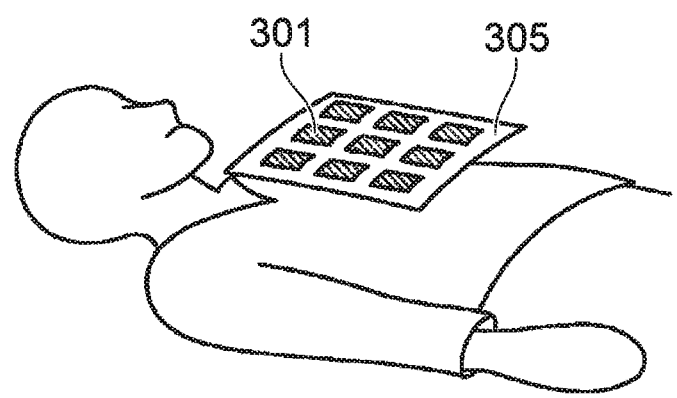
FIG. 28 is a schematic view showing the magnetic sensor according to the third embodiment.

FIG. 28 is a schematic view showing the magnetic sensor according to the third embodiment.

FIG. 28 is an example of a magnetic detection instrument. In the example shown in FIG. 28, the sensor part 301 is provided on a hard base body 305 having a flat plate configuration.

The input and output of the signal obtained from the sensor part 301 in the example shown in FIG. 28 is similar to the input and output described in reference to FIG. 27. The processing of the signal obtained from the sensor part 301 in the example shown in FIG. 28 is similar to the processing described in reference to FIG. 27.

There is a reference example in which a SQUID (Superconducting Quantum Interference Device) magnetic sensor is used as a device to measure a faint magnetic field such as a magnetic field generated from a living body, etc. Because superconductivity is used in the reference example, the device is large; and the power consumption is large. The burden on the measurement object (the patient) is large.

According to the embodiment, the device can be small. The power consumption can be suppressed. The burden on the measurement object (the patient) can be reduced. According to the embodiment, the SN ratio of the magnetic field detection can be improved. The sensitivity can be increased.

The embodiments may include the following configurations (e.g., technological proposals).

Configuration 1

A magnetic sensor, comprising a first element,
the first element including:
a first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length;
a first magnetic layer, a direction from the first portion toward the first magnetic layer being aligned with the second direction;
a first nonmagnetic portion provided between the first portion and the first magnetic layer;
a first intermediate magnetic layer provided between the first portion and the first nonmagnetic portion; and
a first interconnect including a portion extending along the third direction and overlapping at least a portion of the first portion in the second direction.

Configuration 2

The magnetic sensor according to Configuration 1, wherein a magnetization of the first magnetic layer is aligned with the third direction.

Configuration 3

The magnetic sensor according to Configuration 1 or 2, wherein an electrical resistance between the first magnetic part and the first magnetic layer has an even-function characteristic of a magnetic field applied to the first element.

Configuration 4

The magnetic sensor according to Configuration 1 or 2, wherein an electrical resistance between the first magnetic part and the first magnetic layer has a first value when a first magnetic field is applied to the first element, has a second value when a second magnetic field is applied to the first element, and has a third value when a third magnetic field is applied to the first element, an absolute value of the first magnetic field is less than an absolute value of the second magnetic field and less than an absolute value of the third magnetic field, an orientation of the second magnetic field is the reverse of an orientation of the third magnetic field, and the first value is less than the second value and less than the third value.

Configuration 5

The magnetic sensor according to Configuration 3 or 4, further comprising a circuit part, the circuit part including:
 a current supply circuit configured to supply an alternating current to the first interconnect; and
 a detection circuit configured to detect a value corresponding to the electrical resistance.

Configuration 6

The magnetic sensor according to any one of Configurations 1 to 5, wherein a portion of the first intermediate magnetic layer overlaps the second portion and the third portion in the second direction.

Configuration 7

The magnetic sensor according to any one of Configurations 1 to 6, wherein the first element further includes a first magnetic member, the first magnetic member includes at least one selected from the group consisting of Ir—Mn, Pt—Mn, and Ni—Mn, and the first magnetic layer is between the first nonmagnetic portion and the first magnetic member in the second direction.

Configuration 8

The magnetic sensor according to any one of Configurations 1 to 4, further comprising a second element, a third element, and a fourth element, the first element further including the first interconnect including a portion extending along the third direction, the second element including a second magnetic part, a second magnetic layer, a second nonmagnetic portion, a second intermediate magnetic layer, and a second interconnect, the second magnetic part including a fourth portion, a fifth portion, and a sixth portion, a direction from the fifth portion toward the sixth portion being aligned with a fourth direction, the fourth portion being between the fifth portion and the sixth portion in the fourth direction, the fourth portion having a seventh length and an eighth length, the seventh length being along a fifth direction crossing the fourth direction, the eighth length being along a sixth direction crossing a plane including the fourth direction and the fifth direction, the fifth portion having at least one of a ninth length along the fifth direction or a tenth length along the sixth direction, the ninth length being longer than the seventh length, the tenth length being longer than the eighth length, the sixth portion having at least one of an eleventh length along the fifth direction or a twelfth length along the sixth direction, the eleventh length being longer than the seventh length, the twelfth length being longer than the eighth length, a direction from the fourth portion toward the second magnetic layer being aligned with the fifth direction, the second nonmagnetic portion being provided between the fourth portion and the second magnetic layer, the second intermediate magnetic layer being provided between the fourth portion and the second nonmagnetic portion, the second interconnect including a portion extending along the sixth direction, the third element including a third magnetic part, a third magnetic layer, a third nonmagnetic portion, a third intermediate magnetic layer, and a third interconnect, the third magnetic part including a seventh portion, an eighth portion, and a ninth portion, a direction from the eighth portion toward the ninth portion being aligned with a seventh direction, the seventh portion being between the eighth portion and the ninth portion in the seventh direction, the seventh portion having a thirteenth length and a fourteenth length, the thirteenth length being along an eighth direction crossing the seventh direction, the fourteenth length being along a ninth direction crossing a plane including the seventh direction and the eighth direction, the eighth portion having at least one of a fifteenth length along the eighth direction or a sixteenth length along the ninth direction, the fifteenth length being longer than the thirteenth length, the sixteenth length being longer than the fourteenth length, the ninth portion having at least one of a seventeenth length along the eighth direction or an eighteenth length along the ninth direction, the seventeenth length being longer than the thirteenth length, the eighteenth length being longer than the fourteenth length, a direction from the seventh portion toward the third magnetic layer being aligned with the eighth direction, the third nonmagnetic portion being provided between the seventh portion and the third magnetic layer, the third intermediate magnetic layer being provided between the seventh portion and the third nonmagnetic portion, the third interconnect including a portion extending along the ninth direction, the fourth element including a fourth magnetic part, a fourth magnetic layer, a fourth nonmagnetic portion, a fourth intermediate magnetic layer, and a fourth interconnect, the fourth magnetic part including a tenth portion, an eleventh portion, and a twelfth portion, a direction from the eleventh portion toward the twelfth portion being aligned with a tenth direction, the tenth portion being between the eleventh portion and the twelfth portion in the tenth direction, the tenth portion having a nineteenth length and a twentieth length, the nineteenth length being along an eleventh direction crossing the tenth direction, the twentieth length being along a twelfth direction crossing a plane including the seventh direction and the eighth direction, the eleventh portion having at least one of a twenty-first length along the eleventh direction or a twenty-second length along the twelfth direction, the twenty-first length being longer than the nineteenth length, the twenty-second length being longer than the twentieth length, the twelfth portion having at least one of a twenty-third length along the eleventh direction or a twenty-fourth length along the twelfth direction, the twenty-third length being longer than the nineteenth length, the twenty-fourth length being longer than the twentieth length, a direction from the tenth portion toward the fourth magnetic layer being aligned with the eleventh direction, the fourth nonmagnetic portion being provided between the tenth portion and the fourth magnetic layer, the fourth intermediate magnetic layer being provided between the tenth portion and the fourth nonmagnetic portion, the fourth interconnect including a portion extending along the twelfth direction.

Configuration 9

The magnetic sensor according to Configuration 8, further comprising a circuit part, the circuit part including a current supply circuit, the current supply circuit being configured to supply a first alternating current to the first interconnect, configured to supply a second alternating current to the second interconnect, configured to supply a third alternating current to the third interconnect, and configured to supply a fourth alternating current to the fourth interconnect, an orientation of a first current magnetic field having a reverse component of an orientation of a second current magnetic field and having a reverse component of an orientation of a third current magnetic field, the first current magnetic field being generated by the first alternating current and applied to the first portion, the second current magnetic field being generated by the second alternating current and applied to the fourth portion, the third current magnetic field being generated by the third alternating current and applied to the seventh portion, an orientation of a fourth current magnetic field having the reverse component of the orientation of the second current magnetic field and having the reverse component of the orientation of the third current magnetic field, the fourth current magnetic field being generated by the fourth alternating current and applied to the tenth portion.

Configuration 10

The magnetic sensor according to Configuration 9, wherein the circuit part further includes a detection circuit, the detection circuit being configured to output a signal corresponding to a potential difference between a first connection point and a second connection point, a first current path and a third current path are electrically connected to each other in series at the first connection point, the first current path including the first magnetic part and the first magnetic layer, the third current path including the third magnetic part and the third magnetic layer, and a second current path and a fourth current path are electrically connected to each other in series at the second connection point, the second current path including the second magnetic part and the second magnetic layer, the fourth current path including the fourth magnetic part and the fourth magnetic layer.

Configuration 11

A magnetic sensor, comprising a first element, the first element including:

a first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length, a first counter magnetic part including a fourth portion, a fifth portion, and a sixth portion, a direction from the first portion toward the fourth portion being aligned with the second direction, a direction from the second portion toward the fifth portion being aligned with the second direction, a direction from the third portion toward the sixth portion being aligned with the second direction, the fourth portion being between the fifth portion and the sixth portion in the first direction, the fourth portion having a seventh length along the second direction and an eighth length along the third direction, the fifth portion having at least one of a ninth length along the second direction or a tenth length along the third direction, the ninth length being longer than the seventh length, the tenth length being longer than the eighth length, the sixth portion having at least one of an eleventh length along the second direction or a twelfth length along the third direction, the eleventh length being longer than the seventh length, the twelfth length being longer than the eighth length, a first nonmagnetic portion provided between the first portion and the fourth portion, a first intermediate magnetic layer provided between the first portion and the first nonmagnetic portion;

a first counter intermediate magnetic layer provided between the first nonmagnetic portion and the fourth portion; and a first interconnect including a portion extending along the third direction and overlapping the first portion in the second direction.

Configuration 12

The magnetic sensor according to Configuration 11, wherein a magnetization of the fifth portion is aligned with a reverse orientation of a magnetization of the second portion, and a magnetization of the sixth portion is aligned with a reverse orientation of a magnetization of the third portion.

Configuration 13

The magnetic sensor according to Configuration 11 or 12, wherein an electrical resistance between the first magnetic part and the first counter magnetic part has an even-function characteristic of a magnetic field applied to the first element.

Configuration 14

The magnetic sensor according to Configuration 11 or 12, wherein an electrical resistance between the first magnetic part and the first counter magnetic part has a first value when a first magnetic field is applied to the first element, has a second value when a second magnetic field is applied to the first element, and has a third value when a third magnetic field is applied to the first element, an absolute value of the first magnetic field is less than an absolute value of the second magnetic field and less than an absolute value of the third magnetic field, an orientation of the second magnetic field is the reverse of an orientation of the third magnetic field, and the first value is greater than the second value and greater than the third value.

Configuration 15

The magnetic sensor according to Configuration 13 or 14, further comprising a circuit part, the circuit part including:
a current supply circuit configured to supply an alternating current to the first interconnect; and
a detection circuit configured to detect a value corresponding to the electrical resistance.

Configuration 16

The magnetic sensor according to any one of Configurations 11 to 15, wherein the first element further includes a first film, a second film, a third film, and a fourth film, the first film and the second film include one of a first material or a second material, the third film and the fourth film include the other of the first material or the second material, the first material includes at least one of Ru, Ir, or Rh, the second material includes at least one of Co, Fe, or Ni, the second portion includes a first partial region and a second partial region, a direction from the first partial region toward the second partial region being aligned with the third direction, the fifth portion includes a third partial region and a fourth partial region, a direction from the third partial region toward the fourth partial region being aligned with the third direction, the first element further includes a first magnetic member, a second magnetic member, a third magnetic member, and a fourth magnetic member, the first magnetic member, the second magnetic member, the third magnetic member, and the fourth magnetic member include at least one selected from the group consisting of Ir—Mn, Pt—Mn, and Ni—Mn, the first film is provided between the first partial region and the first magnetic member, the second film is provided between the second partial region and the second magnetic member, the third film is provided between the third partial region and the third magnetic member, and the fourth film is provided between the fourth partial region and the fourth magnetic member.

Configuration 17

The magnetic sensor according to Configuration 16, wherein the first element further includes a fifth film, a sixth film, a seventh film, and an eighth film, the fifth film and the sixth film include the one of the first material or the second material, the seventh film and the eighth film include the other of the first material or the second material, the third portion includes a fifth partial region and a sixth partial region, a direction from the fifth partial region toward the sixth partial region being aligned with the third direction, the sixth portion includes a seventh partial region and an eighth partial region, a direction from the seventh partial region toward the eighth partial region being aligned with the third direction, the first element further includes a fifth magnetic member, a sixth magnetic member, a seventh magnetic member, and an eighth magnetic member, the fifth magnetic member, the sixth magnetic member, the seventh magnetic member, and the eighth magnetic member include at least one selected from the group consisting of Ir—Mn, Pt—Mn, and Ni—Mn, the fifth film is provided between the fifth partial region and the fifth magnetic member, the sixth film is provided between the sixth partial region and the sixth magnetic member, the seventh film is provided between the seventh partial region and the seventh magnetic member, and the eighth film is provided between the eighth partial region and the eighth magnetic member.

Configuration 18

The magnetic sensor according to any one of Configurations 11 to 14, further comprising a circuit part, a second element, a third element, and a fourth element, the second element including a second magnetic part, a second counter magnetic part, a second nonmagnetic portion, a second intermediate magnetic layer, a second counter intermediate magnetic layer, and a second interconnect, the second magnetic part including a seventh portion, an eighth portion, and a ninth portion, a direction from the eighth portion toward the ninth portion being aligned with a fourth direction, the seventh portion being between the eighth portion and the ninth portion in the fourth direction, the seventh portion having a thirteenth length and a fourteenth length, the thirteenth length being along a fifth direction crossing the fourth direction, the fourteenth length being along a sixth direction crossing a plane including the fourth direction and the fifth direction, the eighth portion having at least one of a fifteenth length along the fifth direction or a sixteenth length along the sixth direction, the fifteenth length being longer than the thirteenth length, the sixteenth length being longer than the fourteenth length, the ninth portion having at least one of a seventeenth length along the fifth direction or an eighteenth length along the sixth direction, the seventeenth length being longer than the thirteenth length, the eighteenth length being longer than the fourteenth length, the second counter magnetic part including a tenth portion, an eleventh portion, and a twelfth portion, a direction from the seventh portion toward the tenth portion being aligned with the fifth direction, a direction from the eighth portion toward the eleventh portion being aligned with the fifth direction, a direction from the ninth portion toward the twelfth portion being aligned with the fifth direction, the tenth portion being between the eleventh portion and the twelfth portion in the fourth direction, the tenth portion having a nineteenth length along the fifth direction and a twentieth length along the sixth direction, the eleventh portion having at least one of a twenty-first length along the fifth direction or a twenty-second length along the sixth direction, the twenty-first length being longer than the nineteenth length, the twenty-second length being longer than the twentieth length, the twelfth portion having at least one of a twenty-third length along the fifth direction or a twenty-fourth length along the sixth direction, the twenty-third length being longer than the nineteenth length, the twenty-fourth length being longer than the twentieth length, the second nonmagnetic portion being provided between the seventh portion and the tenth portion, the second intermediate magnetic layer being provided between the seventh portion and the second nonmagnetic portion, the second counter intermediate magnetic layer being provided between the second nonmagnetic portion and the tenth portion, the second interconnect including a portion extending along the sixth direction, the third element including a third magnetic part, a third counter magnetic part, a third nonmagnetic portion, a third intermediate magnetic layer, a third counter intermediate magnetic layer, and a third interconnect, the third magnetic part including a thirteenth portion, a fourteenth portion, and a fifteenth portion, a direction from the fourteenth portion toward the fifteenth portion being aligned with a seventh direction, the thirteenth portion being between the fourteenth portion and the fifteenth portion in the seventh direction, the thirteenth portion having a twenty-fifth length and a twenty-sixth length, the twenty-fifth length being along an eighth direction crossing the seventh direction, the twenty-sixth length being along a ninth direction crossing a plane including the seventh direction and the eighth direction, the fourteenth portion having at least one of a twenty-seventh length along the eighth direction or a twenty-eighth length along the ninth direction, the twenty-seventh length being longer than the twenty-fifth length, the twenty-eighth length being longer than the twenty-sixth length, the fifteenth portion having at least one of a twenty-ninth length along the eighth direction or a thirtieth length along the ninth direction, the twenty-ninth length being longer than the twenty-fifth length, the thirtieth length being longer than the twenty-sixth length, the third counter magnetic part including a sixteenth portion, a seventeenth portion, and an eighteenth portion, a direction from the thirteenth portion toward the sixteenth portion being aligned with the eighth direction, a direction from the fourteenth portion toward the seventeenth portion being aligned with the eighth direction, a direction from the fifteenth portion toward the eighteenth portion being aligned with the eighth direction, the sixteenth portion being between the seventeenth portion and the eighteenth portion in the seventh direction, the sixteenth portion having a thirty-first length along the eighth direction and a thirty-second length along the ninth direction, the seventeenth portion having at least one of a thirty-third length along the eighth direction or a thirty-fourth length along the ninth direction, the thirty-third length being longer than the thirty-first length, the thirty-fourth length being longer than the thirty-second length, the eighteenth portion having at least one of a thirty-fifth length along the eighth direction or a thirty-sixth length along the ninth direction, the thirty-fifth length being longer than the thirty-first length, the thirty-sixth length being longer than the thirty-second length, the third nonmagnetic portion being provided between the thirteenth portion and the sixteenth portion, the third intermediate magnetic layer being provided between the thirteenth portion and the third nonmagnetic portion, the third counter intermediate magnetic layer being provided between the third nonmagnetic portion and the sixteenth portion, the third interconnect including a portion extending along the ninth direction, the fourth element including a fourth magnetic part, a fourth counter magnetic part, a fourth nonmagnetic portion, a fourth intermediate magnetic layer, a fourth counter intermediate magnetic layer, and a fourth interconnect, the fourth magnetic part including a nineteenth portion, a twentieth portion, and a twenty-first portion, a direction from the twentieth portion toward the twenty-first portion being aligned with a tenth direction, the nineteenth portion being between the twentieth portion and the twenty-first portion in the tenth direction, the nineteenth portion having a thirty-seventh length and a thirty-eighth length, the thirty-seventh length being along an eleventh direction crossing the tenth direction, the thirty-eighth length being along a twelfth direction crossing a plane including the tenth direction and the eleventh direction, the twentieth portion having at least one of a thirty-ninth length along the eleventh direction or a fortieth length along the twelfth direction, the thirty-ninth length being longer than the thirty-seventh length, the fortieth length being longer than the thirty-eighth length, the twenty-first portion having at least one of a forty-first length along the eleventh direction or a forty-second length along the twelfth direction, the forty-first length being longer than the thirty-seventh length, the forty-second length being longer than the thirty-eighth length, the fourth counter magnetic part including a twenty-second portion, a twenty-third portion, and a twenty-fourth portion, a direction from the twenty-third portion toward the twenty-fourth portion being aligned with the eleventh direction, a direction from the twentieth portion toward the twenty-third portion being aligned with the eleventh direction, a direction from the twenty-first portion toward the twenty-fourth portion being aligned with the eleventh direction, the twenty-second portion being between the twenty-third portion and the twenty-fourth portion in the tenth direction, the twenty-second portion having a forty-third length along the eleventh direction and a forty-fourth length along the twelfth direction, the twenty-third portion having at least one of a forty-fifth length along the eleventh direction or a forty-sixth length along the twelfth direction, the forty-fifth length being longer than the forty-third length, the forty-sixth length being longer than the forty-fourth length, the twenty-fourth portion having at least one of a forty-seventh length along the eleventh direction or a forty-eighth length along the twelfth direction, the forty-seventh length being longer than the forty-third length, the forty-eighth length being longer than the forty-fourth length, the fourth nonmagnetic portion being provided between the nineteenth portion and the twenty-second portion, the fourth intermediate magnetic layer being provided between the nineteenth portion and the fourth nonmagnetic portion, the fourth counter intermediate magnetic layer being provided between the fourth nonmagnetic portion and the twenty-second portion, the fourth interconnect including a portion extending along the twelfth direction, the circuit part including a current supply circuit, the current supply circuit being configured to supply a first alternating current to the first interconnect, configured to supply a second alternating current to the second interconnect, configured to supply a third alternating current to the third interconnect, and configured to supply a fourth alternating current to the fourth interconnect, an orientation of a first current magnetic field having a reverse component of an orientation of a second current magnetic field and having a reverse component of an orientation of a third current magnetic field, the first current magnetic field being generated by the first alternating current and applied to the first portion, the second current magnetic field being generated by the second alternating current and applied to the seventh portion, the third current magnetic field being generated by the third alternating current and applied to the thirteenth portion, an orientation of a fourth current magnetic field having the reverse component of the orientation of the second current magnetic field and having the reverse component of the orientation of the third current magnetic field, the fourth current magnetic field being generated by the fourth alternating current and applied to the nineteenth portion.

Configuration 19

The magnetic sensor according to Configuration 18, wherein
the circuit part further includes a detection circuit,
the detection circuit configured to output a signal corresponding to a potential difference between a first connection point and a second connection point,
a first current path and a third current path are electrically connected to each other in series at the first connection point, the first current path including the first magnetic part and the first magnetic layer, the third current path including the third magnetic part and the third magnetic layer, and
a second current path and a fourth current path are electrically connected to each other in series at the second connection point, the second current path including the second magnetic part and the second magnetic layer, the fourth current path including the fourth magnetic part and the fourth magnetic layer.

Configuration 20

The magnetic sensor according to any one of Configurations 1 to 19, wherein the first nonmagnetic portion includes magnesium and oxygen.

Configuration 21

A diagnostic device, comprising:
the magnetic sensor according to any one of Configurations 1 to 20; and
a processor processing an output signal obtained from the magnetic sensor.

Fourth Embodiment

FIG. 29A to FIG. 29D are schematic views illustrating a magnetic sensor according to a fourth embodiment.

FIG. 29A is a plan view as viewed along arrow AR of FIG. 29C and FIG. 29D. FIG. 29B is a line B1-B2 cross-sectional view of FIG. 29A. FIG. 29C is a line A1-A2 cross-sectional view of FIG. 29A. FIG. 29D is a line A3-A4 cross-sectional view of FIG. 29A.

As shown in FIG. 29A to FIG. 29D, the magnetic sensor 130 according to the embodiment includes a first structure body 81. The first structure body 81 includes the first magnetic part 10A, the second magnetic part 10B, a first conductive member 21, the first magnetic layer 11L, the second magnetic layer 12L, the first nonmagnetic portion 11n, and the second nonmagnetic portion 12n.

The first magnetic part 10A includes the first portion p1, the second portion p2, and the third portion p3. The direction from the second portion p2 toward the third portion p3 is aligned with the first direction D1. The first portion p1 is between the second portion p2 and the third portion p3 in the first direction D1. The first direction D1 is, for example, the X-axis direction.

The first portion p1 has the first length L1 along the second direction D2 crossing the first direction D1, and the second length L2 along the third direction D3 crossing a plane including the first direction D1 and the second direction D2. The second direction D2 is, for example, the Z-axis direction. The third direction D3 is, for example, the Y-axis direction.

The second portion p2 includes at least one of the third length L3 along the second direction D2 that is longer than the first length L1, or the fourth length L4 along the third direction D3 that is longer than the second length L2. In the example, the third length L3 is longer than the first length L1.

The third portion p3 has at least one of the fifth length L5 along the second direction D2 that is longer than the first length L1, or the sixth length L6 along the third direction D3 that is longer than the second length L2. In the example, the fifth length L5 is longer than the first length L1.

The second magnetic part 10B includes the fourth portion p4, the fifth portion p5, and the sixth portion p6. The direction from the fifth portion p5 toward the sixth portion p6 is aligned with the first direction D1. The fourth portion p4 is between the fifth portion p5 and the sixth portion p6 in the first direction D1.

The fourth portion p4 has the seventh length L7 along the second direction D2 and the eighth length L8 along the third direction D3. The fifth portion p5 has at least one of the ninth length L9 along the second direction D2 that is longer than the seventh length L7, or the tenth length L10 along the third direction D3 that is longer than the eighth length L8. The sixth portion p6 has at least one of the eleventh length L11 along the second direction D2 that is longer than the seventh length L7, or the twelfth length L12 along the third direction D3 that is longer than the eighth length L8.

For example, the first conductive member 21 opposes the first portion p1 of the first magnetic part 10A and the fourth portion p4 of the second magnetic part 10B in the Z-axis direction.

For example, the direction from a portion of the first portion p1 toward a portion 21p of the first conductive member 21 is aligned with the second direction D2. The direction from a portion of the fourth portion p4 toward another portion 21q of the first conductive member 21 is aligned with the second direction D2.

The first magnetic layer 11L is provided between the portion of the first portion p1 recited above and the portion 21p of the first conductive member 21. The second magnetic layer 12L is provided between the portion of the fourth portion p4 recited above and the other portion 21q of the first conductive member 21.

The first nonmagnetic portion 11n is provided between the portion of the first portion p1 recited above and the first magnetic layer 11L. The second nonmagnetic portion 12n is provided between the portion of the fourth portion p4 recited above and the second magnetic layer 12L.

For example, the first magnetic part 10A and the second magnetic part 10B function as MFCs. For example, the first portion p1 and the fourth portion p4 function as free magnetic layers. The first magnetic layer 11L and the second magnetic layer 12L function as reference layers. For example, the first magnetic layer 11L and the second magnetic layer 12L are fixed magnetic layers.

The portion of the first portion p1 recited above, the first magnetic layer 11L, and the first nonmagnetic portion 11n are included in one element. The portion of the fourth portion p4 recited above, the second magnetic layer 12L, and the second nonmagnetic portion 12n are included in another one element. The electrical resistances of these elements can change according to an external magnetic field. These elements are connected in series by the first conductive member 21. The effects of the noise can be suppressed. A magnetic sensor can be provided in which the sensitivity can be increased further. By providing multiple elements (e.g., TMR elements) in the magnetic sensor 130, the element surface area (e.g., the TMR junction surface area) is large. High sensitivity is obtained easily thereby.

As shown in FIG. 29A to FIG. 29D, the magnetic sensor 130 according to the embodiment may further include the first interconnect 51. At least a portion of the first interconnect 51 is along the third direction D3. For example, the first interconnect 51 includes the portion 51p extending along the third direction D3. In the example, at least a portion (the portion 51p) of the first interconnect 51 overlaps at least a portion of the first portion p1 and at least a portion of the fourth portion p4 in the second direction D2. For example, higher sensitivity is obtained by providing such a first interconnect 51 and by applying the configuration described in reference to FIG. 3 and FIG. 4A to FIG. 4C. The magnetic field (the current magnetic field) generated by the current flowing through the first interconnect 51 is applied to the first magnetic layer 11L. For example, the position in the Z-axis direction of the portion 51p is different from the position in the Z-axis direction of the first conductive member 21. The position in the Z-axis direction of the portion 51p is different from the position in the Z-axis direction of the first magnetic layer 11L.

For example, the magnetic sensor 130 may include the circuit part 70, and the circuit part may include the current supply circuit 70a configured to supply an alternating current to the first interconnect 51. The circuit part may include the detection circuit 70d configured to detect a value corresponding to an electrical resistance between the first magnetic part 10A and the first magnetic layer 11L.

Multiple configurations including the first magnetic part 10A and the second magnetic part 10B illustrated in FIG. 29A may be provided. For example, the magnetic sensor 130 may include multiple first structure bodies 81. For example, the multiple first structure bodies 81 are arranged along the third direction D3. The first magnetic part 10A of one of the multiple first structure bodies 81 and the second magnetic part 10B of another one of the multiple first structure bodies 81 are electrically connected to each other. The electrical connection is performed by a magnetic layer (e.g., a magnetic layer similar to the first magnetic layer 11L).

FIG. 30A to FIG. 30D are schematic views illustrating a magnetic sensor according to the fourth embodiment.

FIG. 30A is a plan view as viewed along arrow AR of FIG. 30C and FIG. 30D. FIG. 30B is a line B1-B2 cross-sectional view of FIG. 30A. FIG. 30C is a line A1-A2 cross-sectional view of FIG. 30A. FIG. 30D is a line A3-A4 cross-sectional view of FIG. 30A.

As shown in FIG. 30A to FIG. 30D, the magnetic sensor 131 according to the embodiment also includes the first structure body 81. The configurations of the first magnetic part 10A and the second magnetic part 10B of the magnetic sensor 131 are different from those of the magnetic sensor 130. Otherwise, the configuration of the magnetic sensor 131 is similar to the configuration of the magnetic sensor 130.

In the example as shown in FIG. 30A and FIG. 30C, the second portion p2 has the third length L3 along the second direction D2 that is longer than the first length L1, and the fourth length L4 along the third direction D3 that is longer than the second length L2. The third portion p3 has the fifth length L5 along the second direction D2 that is longer than the first length L1, and the sixth length L6 along the third direction D3 that is longer than the second length L2.

The fifth portion p5 has the ninth length L9 along the second direction D2 that is longer than the seventh length L7, and the tenth length L10 along the third direction D3 that is longer than the eighth length L8. The sixth portion p6 has the eleventh length L11 along the second direction D2 that is longer than the seventh length L7, and the twelfth length L12 along the third direction D3 that is longer than the eighth length L8.

In the magnetic sensor 131 as well, a magnetic sensor can be provided in which the sensitivity can be increased further.

Figure 31:
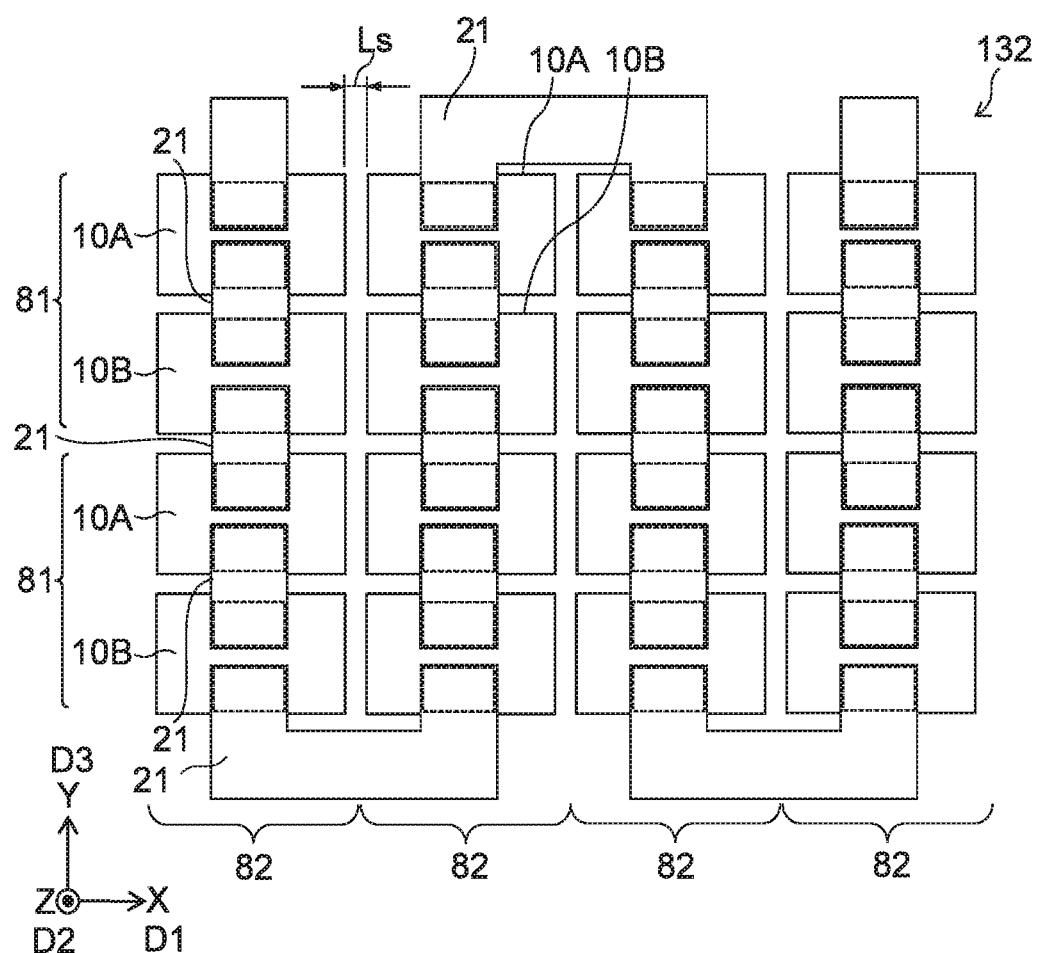
FIG. 31 is a schematic plan view illustrating a magnetic sensor according to the fourth embodiment.

FIG. 31 is a schematic plan view illustrating a magnetic sensor according to the fourth embodiment.

As shown in FIG. 31, the magnetic sensor 132 according to the embodiment includes multiple second structure bodies 82. For example, one of the multiple second structure bodies 82 includes multiple first structure bodies 81. The multiple first structure bodies 81 are arranged along the third direction D3.

The first magnetic part 10A of one of the multiple first structure bodies 81 and the second magnetic part 10B of another one of the multiple first structure bodies 81 are electrically connected to each other. For example, the electrical connection is performed by one of the multiple first conductive members 21. The other one of the multiple first structure bodies 81 is next to the one of the multiple first structure bodies 81.

The multiple second structure bodies 82 are arranged along the first direction D1. One of the multiple second structure bodies 82 and another one of the multiple second structure bodies 82 are electrically connected to each other. For example, the electrical connection is performed by one of the multiple first conductive members 21. The multiple second structure bodies 82 are connected in a meandering configuration.

In such a magnetic sensor 132, for example, the noise can be reduced further.

In the magnetic sensor 132, the direction from the first magnetic part 10A included in one of the multiple second structure bodies 82 toward the first magnetic part 10A included in another one of the multiple second structure bodies 82 is aligned with the first direction D1. Two first magnetic parts 10A that are arranged along the first direction D1 are insulated from each other. In such a case, it is favorable for the magnetic flux to pass between the two first magnetic parts 10A arranged along the first direction D1 substantially without attenuating. For example, the distance (the gap) between the two first magnetic parts 10A arranged along the first direction D1 is set appropriately.

For example, as shown in FIG. 31, the distance along the first direction D1 between the first magnetic part 10A of one of the multiple first structure bodies 81 included in one of the multiple second structure bodies 82 and the first magnetic part 10A of another one of the multiple first structure bodies 81 included in another one of the multiple second structure bodies 82 is taken as a distance Ls. In the embodiment, it is favorable for the distance Ls to be shorter than at least one of the third length L3 (referring to FIG. 29C) or the fifth length L5 (referring to FIG. 29C). The other one of the multiple second structure bodies 82 is next to the one of the multiple second structure bodies 82. Thereby, the magnetic flux easily passes between the two adjacent first magnetic parts 10A substantially without attenuating. The external magnetic field can inflow into the element more effectively.

As shown in FIG. 31, the magnetic field sensor 132 includes the multiple first structure bodies 81. For example, the multiple first structure bodies 81 are arranged along the first direction D1. For example, the distance Ls along the first direction D1 between the first magnetic part 10A of one of the multiple first structure bodies 81 and the first magnetic part 10A of another one of the multiple first structure bodies 81 is shorter than at least one of the third length L3 or the fifth length L5. The other one of the multiple first structure bodies 81 is next to the one of the multiple first structure bodies 81.

Figure 32:
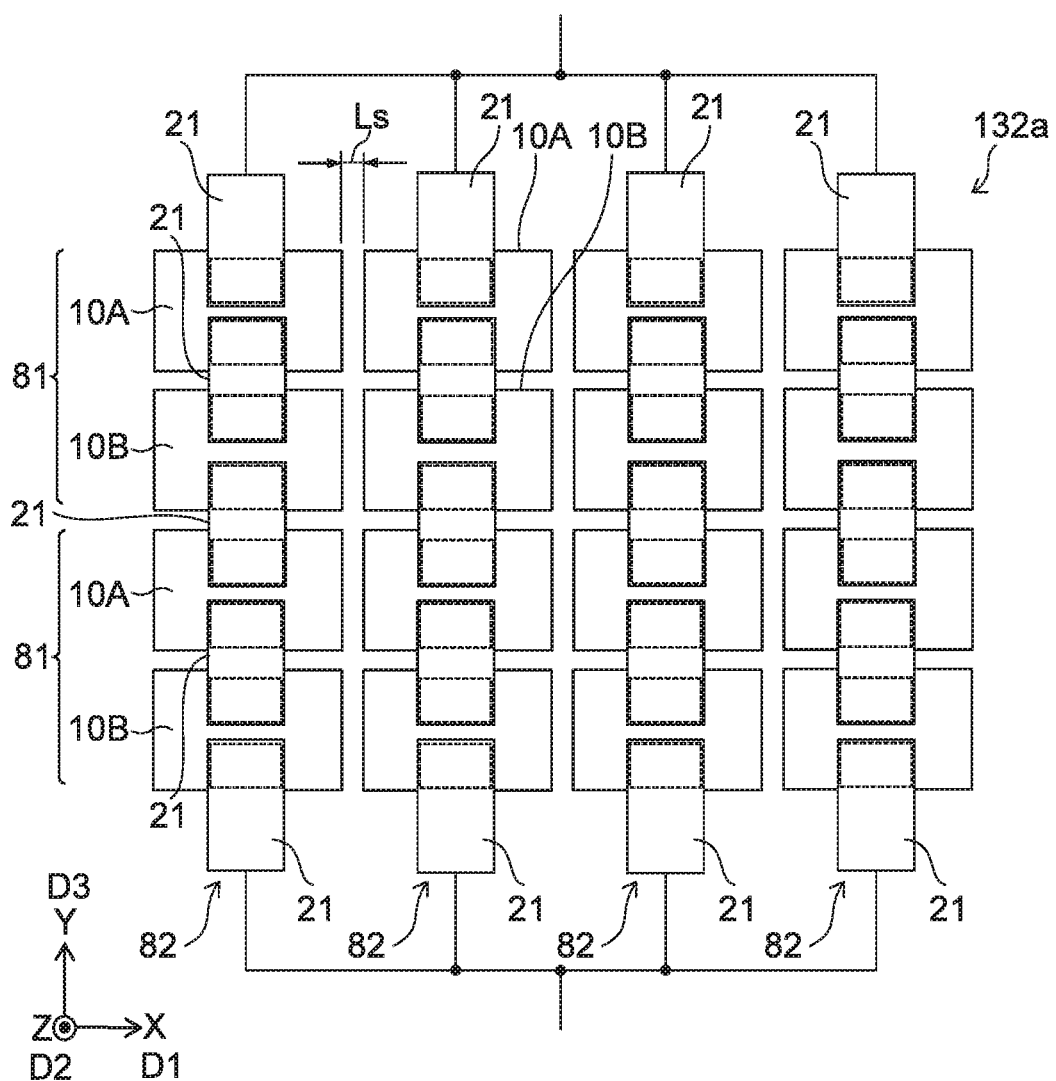
FIG. 32 is a schematic plan view illustrating a magnetic sensor according to the fourth embodiment.

FIG. 32 is a schematic plan view illustrating a magnetic sensor according to the fourth embodiment.

As shown in FIG. 32, the magnetic sensor 132a according to the embodiment includes the multiple second structure bodies 82. For example, one of the multiple second structure bodies 82 includes the multiple first structure bodies 81. The multiple first structure bodies 81 are arranged along the third direction D3. The multiple second structure bodies 82 are electrically connected in parallel in the magnetic sensor 132a. In the magnetic sensor 132a as well, for example, the noise can be reduced further.

Figure 33A:
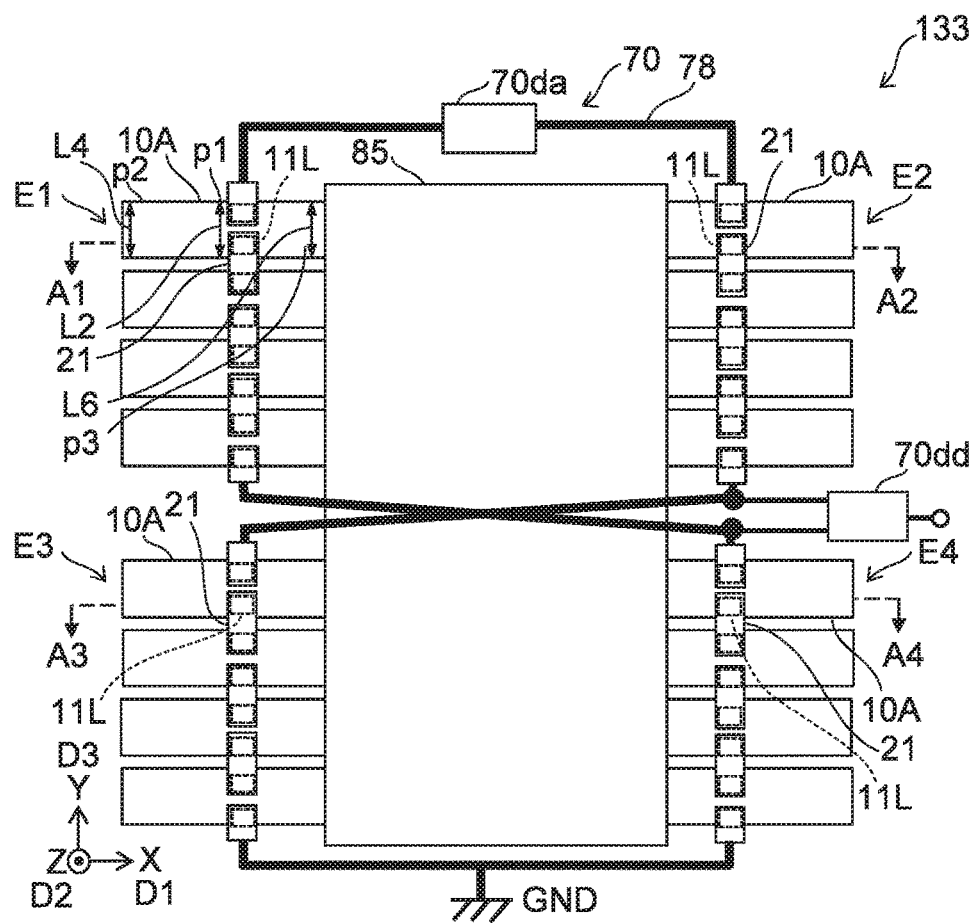
FIG. 33A to FIG. 33C are schematic views illustrating a magnetic sensor according to the fourth embodiment.
Figure 33B:
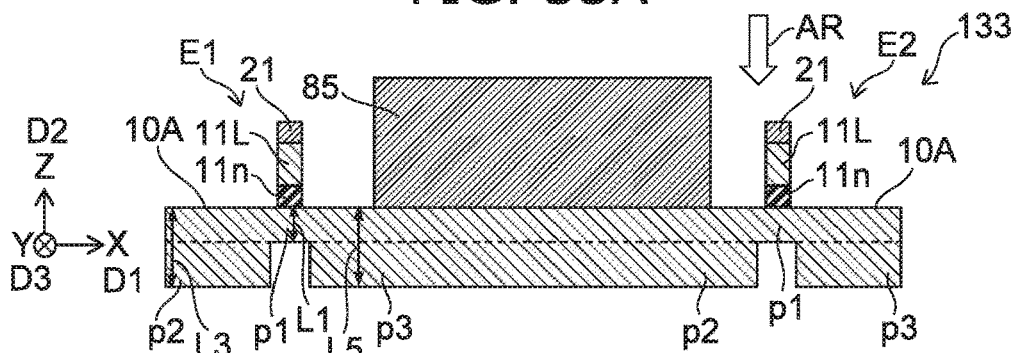
Figure 33C:
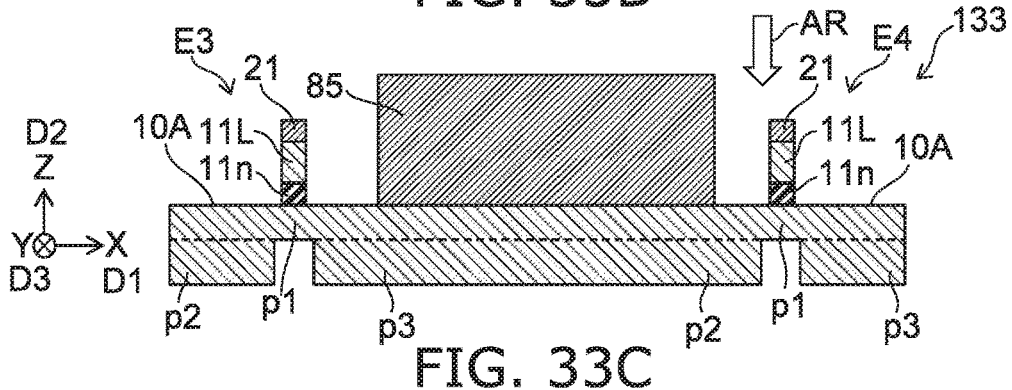

FIG. 33A to FIG. 33C are schematic views illustrating a magnetic sensor according to the fourth embodiment.

FIG. 33A is a plan view as viewed along arrow AR of FIG. 33B and FIG. 33C. FIG. 33B is a line A1-A2 cross-sectional view of FIG. 33A. FIG. 33C is a line A3-A4 cross-sectional view of FIG. 33A.

As shown in FIG. 33A to FIG. 33C, the magnetic sensor 133 according to the embodiment includes the first element E1, the second element E2, the third element E3, the fourth element E4, and a first magnetic section 85. Each of the first element E1, the second element E2, the third element E3, and the fourth element E4 include the first magnetic part 10A, the first conductive member 21, and the first magnetic layer 11L. These elements each may further include the first nonmagnetic portion 11n (referring to FIG. 29B).

The first magnetic part 10A includes the first portion p1, the second portion p2, and the third portion p3. The direction from the second portion p2 toward the third portion p3 is aligned with the first direction D1. The first portion p1 is between the second portion p2 and the third portion p3 in the first direction D1.

The first portion p1 has the first length L1 along the second direction D2 crossing the first direction D1, and the second length L2 along the third direction D3 crossing a plane including the first direction D1 and the second direction D2. The second portion p2 has at least one of the third length L3 along the second direction D2 that is longer than the first length L1, or the fourth length L4 along the third direction D3 that is longer than the second length L2. The third portion p3 has at least one of the fifth length L5 along the second direction D2 that is longer than the first length L1, or the sixth length L6 along the third direction D3 that is longer than the second length L2. In the example, the third length L3 is longer than the first length L1. The fifth length L5 is longer than the first length L1.

Similarly to the magnetic sensor 130, the first magnetic layer 11L is between at least a portion of the first portion p1 and at least a portion of the first conductive member 21 in the second direction D2. The first nonmagnetic portion 11n is between the first magnetic layer 11L and at least a portion of the first portion p1 in the second direction D2.

As shown in FIG. 33A, the direction from the first element E1 toward the second element E2 is aligned with the first direction D1. The direction from the third element E3 toward the fourth element E4 is aligned with the first direction D1. In the example, the direction from the third element E3 toward the first element E1 is aligned with the third direction D3. The direction from the fourth element E4 toward the second element E2 is aligned with the third direction D3.

In the example as shown in FIG. 33B, the third portion p3 of the first element E1 is continuous with the second portion p2 of the second element E2. As shown in FIG. 33C, the third portion p3 of the third element E3 is continuous with the second portion p2 of the fourth element E4.

As shown in FIG. 33B, the direction from the third portion p3 of the first magnetic part 10A of the first element E1 toward a portion of the first magnetic section 85 is aligned with the second direction D2. The direction from the second portion p2 of the first magnetic part 10A of the second element E2 toward a portion of the first magnetic section 85 is aligned with the second direction D2.

As shown in FIG. 33C, the direction from the third portion p3 of the first magnetic part 10A of the third element E3 toward a portion of the first magnetic section 85 is aligned with the second direction D2. The direction from the second portion p2 of the first magnetic part 10A of the fourth element E4 toward a portion of the first magnetic section 85 is aligned with the second direction D2.

For example, the external magnetic field which is the detection object is applied to the first magnetic section 85. For example, the external magnetic field may have a component in the second direction D2. The magnetic flux that has the component in the second direction D2 enters the first magnetic section 85, enters the first magnetic part 10A, becomes magnetic flux having a component in the first direction D1, and concentrates in the first portion p1. For example, the orientation of the magnetic flux applied to the first portion p1 of the first element E1 is the reverse of the orientation of the magnetic flux applied to the first portion p1 of the second element E2. The orientation of the magnetic flux applied to the first portion p1 of the third element E3 is the reverse of the orientation of the magnetic flux applied to the first portion p1 of the fourth element E4. The orientation of the magnetic flux applied to the first portion p1 of the first element E1 is the same as the orientation of the magnetic flux applied to the first portion p1 of the third element E3. The orientation of the magnetic flux applied to the first portion p1 of the second element E2 is the same as the orientation of the magnetic flux applied to the first portion p1 of the fourth element E4. For example, the first magnetic section 85 functions as a MFC.

The first magnetic section 85 may be considered to be a portion of the first magnetic part 10A. In such a case, for example, the sum of the fifth length L5 and the thickness along the second direction D2 of the first magnetic section 85 may be considered to be the "length along the second direction of the third portion".

In the example, the first magnetic section 85 contacts the first magnetic part 10A. In the embodiment, a gap may be provided between the first magnetic section 85 and the first magnetic part 10A. If the gap is sufficiently small compared to the size where the first magnetic part 10A and the first magnetic section 85 contact each other (e.g., the width of the region where the first magnetic part 10A and the first magnetic section 85 contact each other), the magnetic flux can pass between the first magnetic section 85 and the first magnetic part 10A substantially without attenuating.

As shown in FIG. 33A, the first conductive member 21 of the first element E1 is electrically connected to the first conductive member 21 of the fourth element E4. The first conductive member 21 of the second element E2 is electrically connected to the first conductive member 21 of the third element E3. These electrical connections are performed by an interconnect 78, etc.

In the example, each of the first element E1, the second element E2, the third element E3, and the fourth element E4 includes multiple first magnetic parts 10A. One of the multiple first magnetic layers 11L is between a portion of one first conductive member 21 and one of the multiple first magnetic parts 10A. Another one of the multiple first magnetic layers 11L is between another portion of the one first conductive member 21 and another one of the multiple first magnetic parts 10A. The other one of the multiple first magnetic parts 10A is next to the one of the multiple first magnetic parts 10A.

A bridge is formed of the first to fourth elements E1 to E4. For example, a detection can be performed in which the noise is suppressed by detecting the potential (the signal) between the connection point between the first element E1 and the fourth element and the connection point between the second element E2 and the third element E3.

The circuit part 70 is provided in the example. The circuit part 70 includes, for example, the bias voltage application part 70*da* and the detector 70*dd*. The circuit part 70 (e.g., the bias voltage application part 70*da*) supplies a current to the first element E1, the second element E2, the third element E3, and the fourth element E4.

In the example, a voltage (e.g., a direct current voltage) is applied to the first conductive member 21 of the first element E1 and the first conductive member 21 of the second element E2 by the bias voltage application part 70*da*. The first conductive member 21 of the third element E3 and the first conductive member 21 of the fourth element E4 are electrically connected to a ground GND.

The orientation of the current flowing through the first conductive member 21 of the first element E1 includes a component having the same orientation as the current flowing through the first conductive member 21 of the second element E2. The orientation of the current flowing through the first conductive member 21 of the first element E1 includes a component having the same orientation as the current flowing through the first conductive member 21 of the fourth element E4. The orientation of the current flowing through the first conductive member 21 of the third element E3 includes a component having the same orientation as the current flowing through the first conductive member 21 of the second element E2. For example, the current flowing through the first conductive member 21 of the first element E1, the current flowing through the first conductive member 21 of the second element E2, the current flowing through the first conductive member 21 of the third element E3, and the current flowing through the first conductive member 21 of the fourth element E4 are along the third direction D3.

For example, the detector 70*dd* detects the potential (the signal) between the connection point between the first element E1 and the fourth element E4 and the connection point between the second element E2 and the third element E3.

A detection can be performed in which the noise is suppressed.

In the example, a portion of the first magnetic section 85 is between the first magnetic layer 11L of the first element E1 and the first magnetic layer 11L of the second element E2 in the first direction D1. Another portion of the first magnetic section 85 is between the first magnetic layer 11L of the third element E3 and the first magnetic layer 11L of the fourth element E4 in the first direction D1.

Figure 34A:
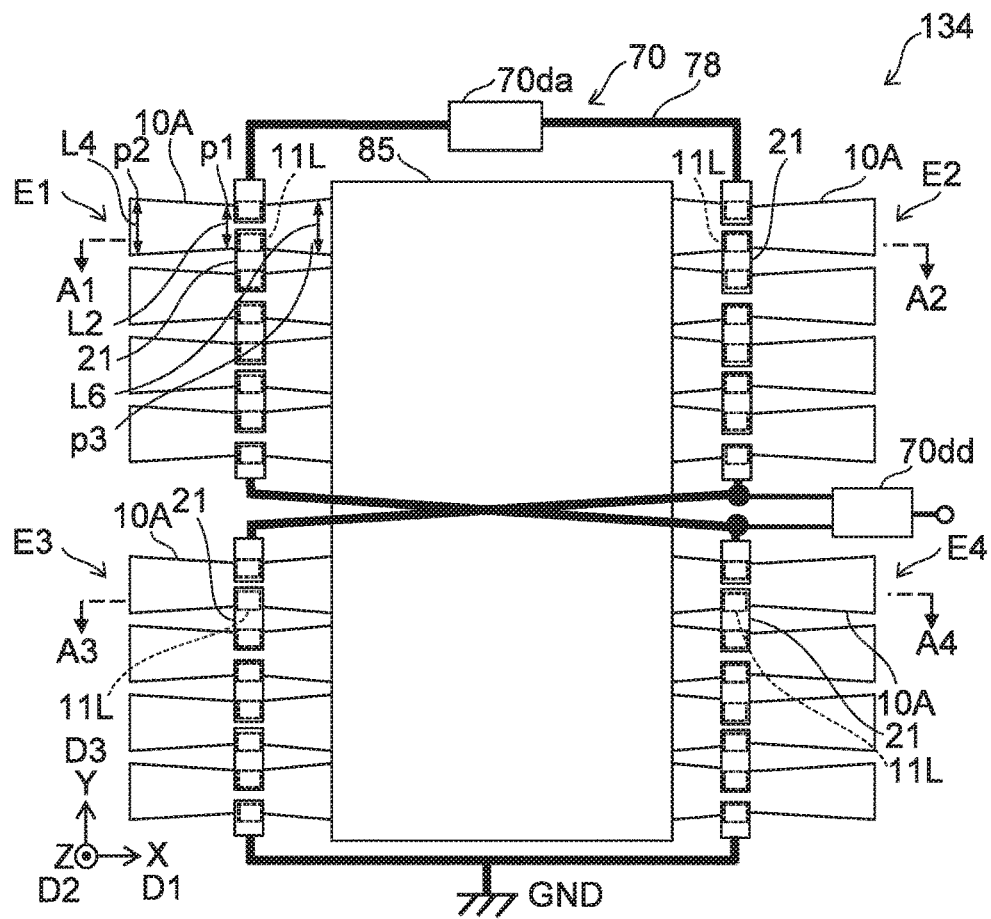
FIG. 34A to FIG. 34C are schematic views illustrating a magnetic sensor according to the fourth embodiment.
Figure 34B:
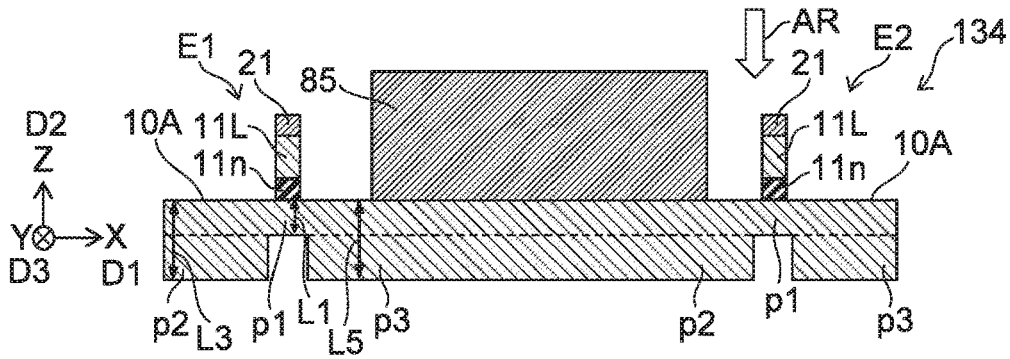
Figure 34C:
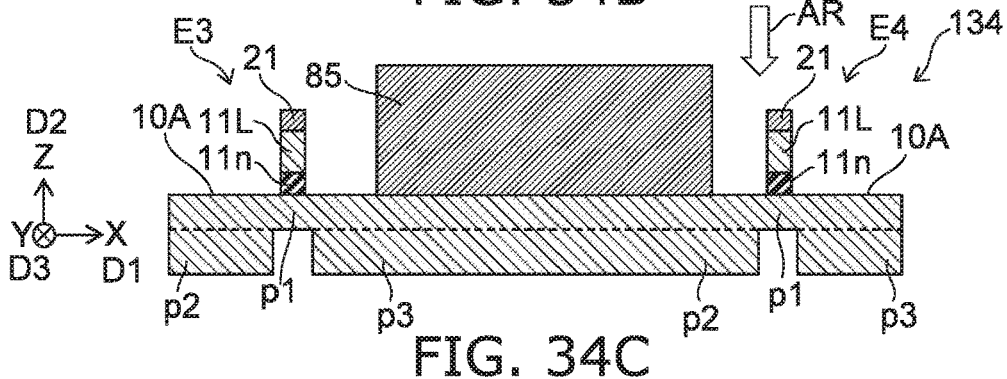

FIG. 34A to FIG. 34C are schematic views illustrating a magnetic sensor according to the fourth embodiment.

FIG. 34A is a plan view as viewed along arrow AR of FIG. 34B and FIG. 34C. FIG. 34B is a line A1-A2 cross-sectional view of FIG. 34A. FIG. 34C is a line A3-A4 cross-sectional view of FIG. 34A.

As shown in FIG. 34A to FIG. 34C, the magnetic sensor 134 according to the embodiment also includes the first element E1, the second element E2, the third element E3, the fourth element E4, and the first magnetic section 85. The configuration of the first magnetic part 10A of the magnetic sensor 134 is different from that of the magnetic sensor 133. Otherwise, the configuration of the magnetic sensor 134 may be the same as the configuration of the magnetic sensor 133.

In the magnetic sensor 134 as shown in FIG. 34A and FIG. 34B, the second portion p2 has the third length L3 along the second direction D2 that is longer than the first length L1 and the fourth length L4 along the third direction D3 that is longer than the second length L2. The third portion p3 has the fifth length L5 along the second direction D2 that is longer than the first length L1, and the sixth length L6 along the third direction D3 that is longer than the second length L2.

In the magnetic sensors 133 and 134 as well, a magnetic sensor can be provided in which the sensitivity can be increased.

FIG. 35A to FIG. 35C and FIG. 36 are schematic views illustrating a magnetic sensor according to the fourth embodiment.

Figure 35A:
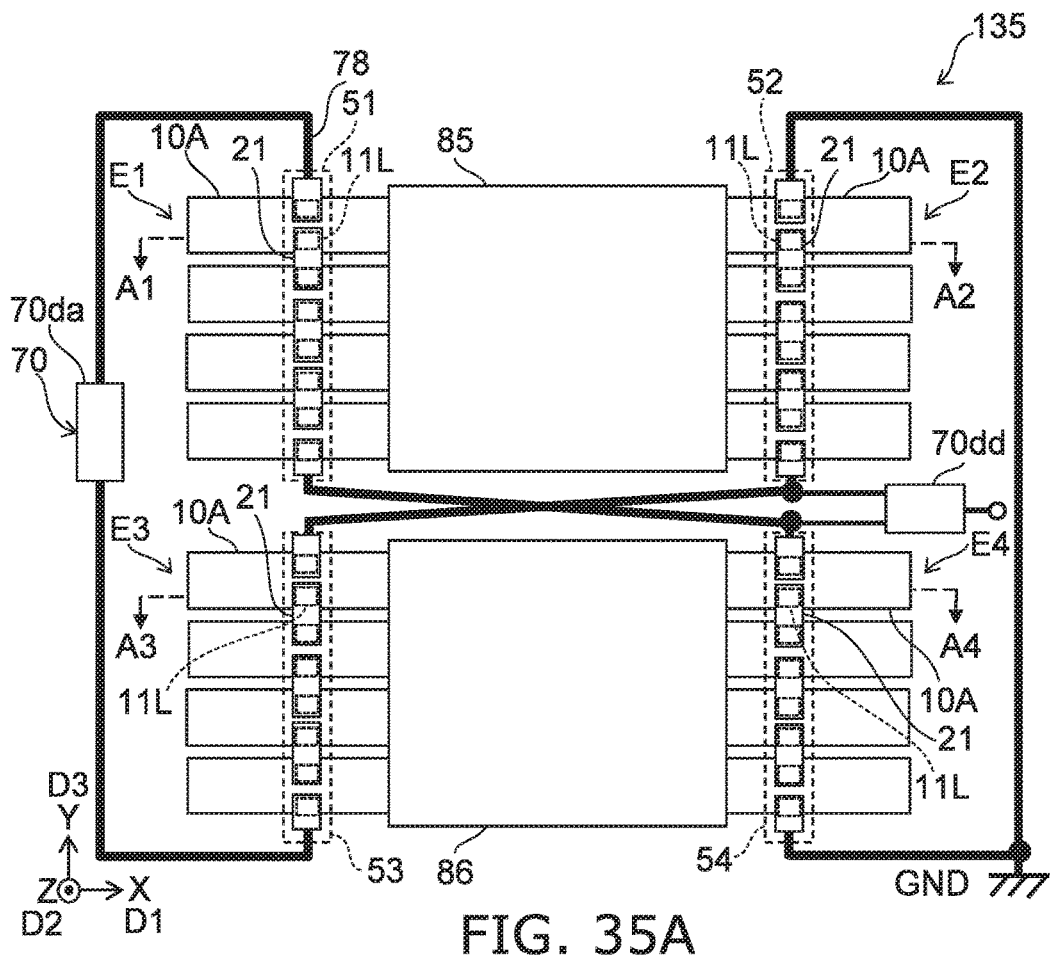
FIG. 35A to FIG. 35C are schematic views illustrating a magnetic sensor according to the fourth embodiment.
Figure 35B:
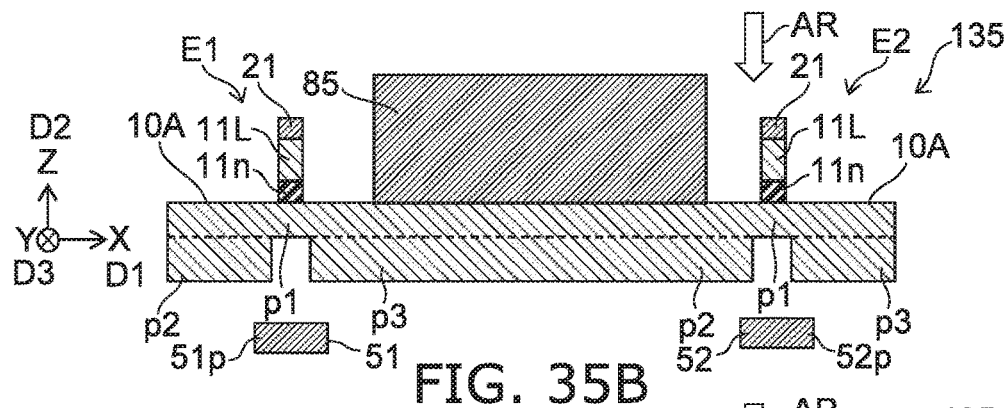
Figure 35C:
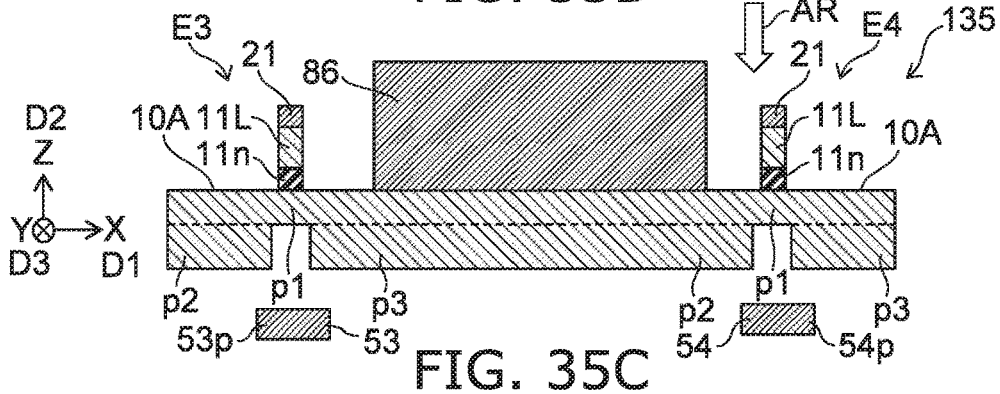
Figure 36:
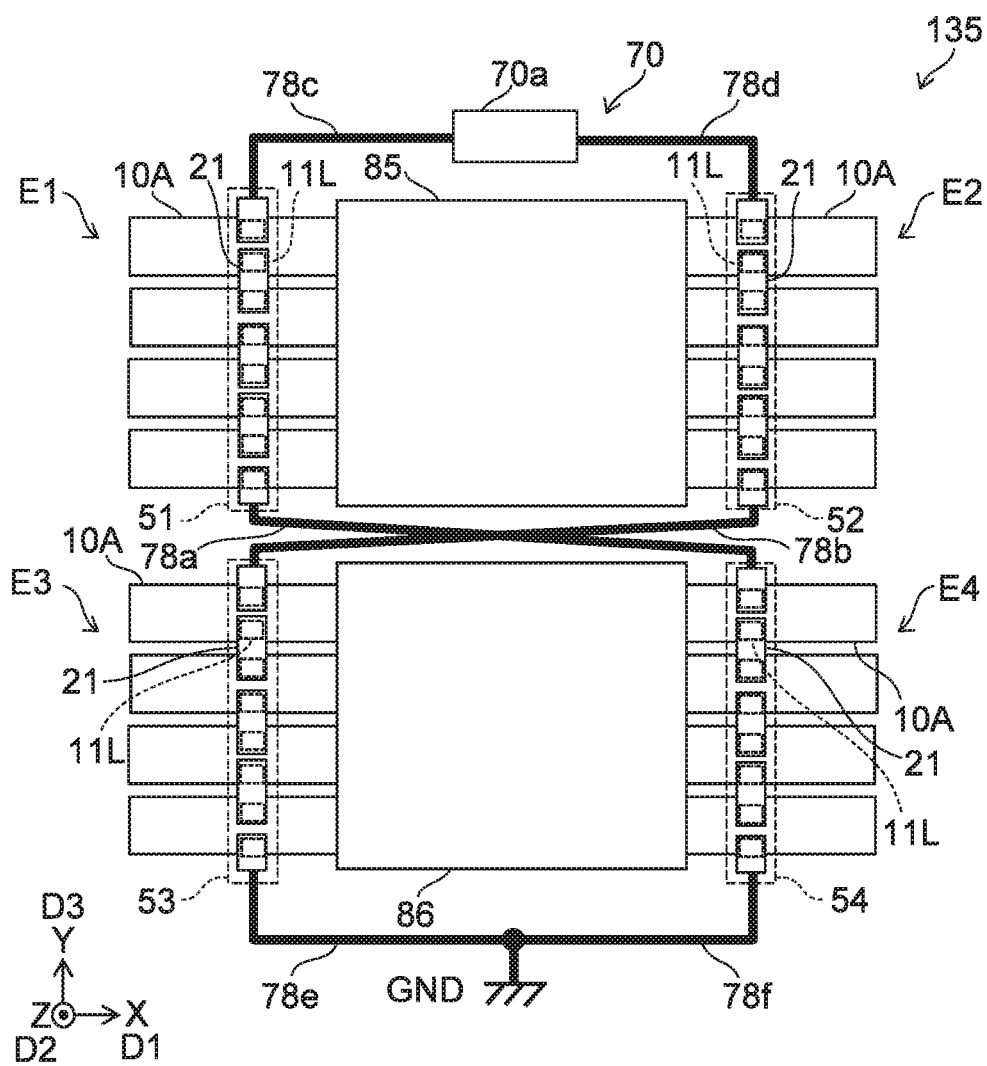
FIG. 36 is a schematic view illustrating the magnetic sensor according to the fourth embodiment.

FIG. 35A and FIG. 36 are plan views when viewed along arrow AR of FIG. 35B and FIG. 35C. FIG. 35B is a line A1-A2 cross-sectional view of FIG. 35A. FIG. 35C is a line A3-A4 cross-sectional view of FIG. 35A.

As shown in FIG. 35A to FIG. 35C, the magnetic sensor 135 according to the embodiment includes the first element E1, the second element E2, the third element E3, the fourth element E4, the first magnetic section 85, and a second magnetic section 86. The first to fourth interconnects 51 to 54 are provided in the magnetic sensor 135. The electrical connections of the first to fourth elements E1 to E4 of the magnetic sensor 135 are different from those of the magnetic sensor 133. Otherwise, the configuration of the magnetic sensor 135 (e.g., the configurations of the first to fourth elements E1 to E4) may be the same as the configuration of the magnetic sensor 133.

For example, in the magnetic sensor 135 as well, the first magnetic layer 11L is between at least a portion of the first portion p1 and at least a portion of the first conductive member 21 in the second direction D2. For example, the direction from the first element E1 toward the second element E2 is aligned with the first direction D1. The direction from the third element E3 toward the fourth element E4 is aligned with the first direction D1.

As shown in FIG. 35B, the direction from the third portion p3 of the first magnetic part 10A of the first element E1 toward a portion of the first magnetic section 85 is aligned with the second direction D2. The direction from the second portion p2 of the first magnetic part 10A of the second element E2 toward a portion of the first magnetic section 85 is aligned with the second direction D2. As shown in FIG. 35C, the direction from the third portion p3 of the first magnetic part 10A of the third element E3 toward a portion of the second magnetic section 86 is aligned with the second direction D2. The direction from the second portion p2 of the first magnetic part 10A of the fourth element E4 toward a portion of the second magnetic section 86 is aligned with the second direction D2.

As shown in FIG. 35A, the first conductive member 21 of the first element E1 is electrically connected to the first conductive member 21 of the fourth element E4. The first conductive member 21 of the second element E2 is electrically connected to the first conductive member 21 of the third element E3. These electrical connections are performed by the interconnect 78, etc.

For example, the circuit part 70 is provided as shown in FIG. 35A. The circuit part 70 includes, for example, the bias voltage application part 70*da* and the detector 70*dd*. The circuit part 70 (e.g., the bias voltage application part 70*da*) supplies a current to the first element E1, the second element E2, the third element E3, and the fourth element E4.

The orientation of the current flowing through the first conductive member 21 of the first element E1 includes a reverse component of the orientation of the current flowing through the first conductive member 21 of the second element E2. The orientation of the current flowing through the first conductive member 21 of the first element E1 includes a component having the same orientation as the current flowing through the first conductive member 21 of the fourth element E4. The orientation of the current flowing through the first conductive member 21 of the third element E3 includes a component having the same orientation as the current flowing through the first conductive member 21 of the second element E2.

For example, the detector 70dd detects the potential (the signal) between the connection point between the first element E1 and the fourth element and the connection point between the second element E2 and the third element E3. A detection can be performed in which the noise is suppressed.

In the magnetic sensor 135 as shown in FIG. 35B, the first magnetic section 85 is between the first magnetic layer 11L of the first element E1 and the first magnetic layer 11L of the second element E2 in the first direction D1. As shown in FIG. 35C, the second magnetic section 86 is between the first magnetic layer 11L of the third element E3 and the first magnetic layer 11L of the fourth element E4 in the first direction D1.

In the example as shown in FIG. 35A to FIG. 35C, at least a portion (e.g., the portion 51p) of the first interconnect 51 overlaps the first portion p1 of the first magnetic part 10A of the first element E1 and the first portion p1 of the first magnetic part 10A of the second element E2 in the second direction D2. In the example, at least a portion of the second interconnect 52 overlaps the first portion p1 of the first magnetic part 10A of the second element E2 and the first portion p1 of the first magnetic part 10A of the fourth element E4 in the second direction D2. The current that flows through at least a portion (e.g., the portion 51p) of the first interconnect 51 and the current that flows through at least a portion of the second interconnect 52 are along the third direction D3.

For example, the magnetic field that is generated by the current flowing through the first interconnect 51 is applied to the first element E1. The magnetic field that is generated by the current flowing through the second interconnect 52 is applied to the second element E2. For example, the magnetic field that is generated by the current flowing through the third interconnect 53 is applied to the third element E3. For example, the magnetic field that is generated by the current flowing through the fourth interconnect 54 is applied to the fourth element E4. For example, the position in the Z-axis direction of the first interconnect 51 is different from the position in the Z-axis direction of the first element E1. For example, the position in the Z-axis direction of the second interconnect 52 is different from the position in the Z-axis direction of the second element E2. For example, the position in the Z-axis direction of the third interconnect 53 is different from the position in the Z-axis direction of the third element E3. For example, the position in the Z-axis direction of the fourth interconnect 54 is different from the position in the Z-axis direction of the fourth element E4.

As shown in FIG. 36, one end of the first interconnect 51 is electrically connected to one end of the fourth interconnect 54. One end of the second interconnect 52 is electrically connected to one end of the third interconnect 53. These electrical connections are performed by an interconnect 78a and an interconnect 78b.

The magnetic sensor 135 includes the current supply circuit 70a. For example, the current supply circuit 70a supplies an alternating current to a current path including the first interconnect 51 and the fourth interconnect 54 and supplies an alternating current to a current path including the second interconnect 52 and the third interconnect 53. As shown in FIG. 36, for example, the connections between the current supply circuit 70a and these current paths are performed by an interconnect 78c and an interconnect 78d. For example, the connections between the ground GND and these current paths are performed by, for example, an interconnect 78e and an interconnect 78f.

The alternating currents are supplied to the first to fourth interconnects 51 to 54 thus connected; and the first to fourth elements E1 to E4 have a bridge connection. For example, the alternating current magnetic field that is applied to the first element E1 has the same phase as the alternating current magnetic field applied to the fourth element E4. For example, the alternating current magnetic field that is applied to the second element E2 has the same phase as the alternating current magnetic field applied to the third element E3. The alternating current magnetic field that is applied to the first element E1 and the alternating current magnetic field that is applied to the fourth element E4 have the reverse phases of the alternating current magnetic field applied to the second element E2 and the alternating current magnetic field applied to the third element E3. The noise can be reduced further. The sensitivity can be increased further.

FIG. 37A to FIG. 37C and FIG. 38 are schematic views illustrating a magnetic sensor according to the fourth embodiment.

Figure 37A:
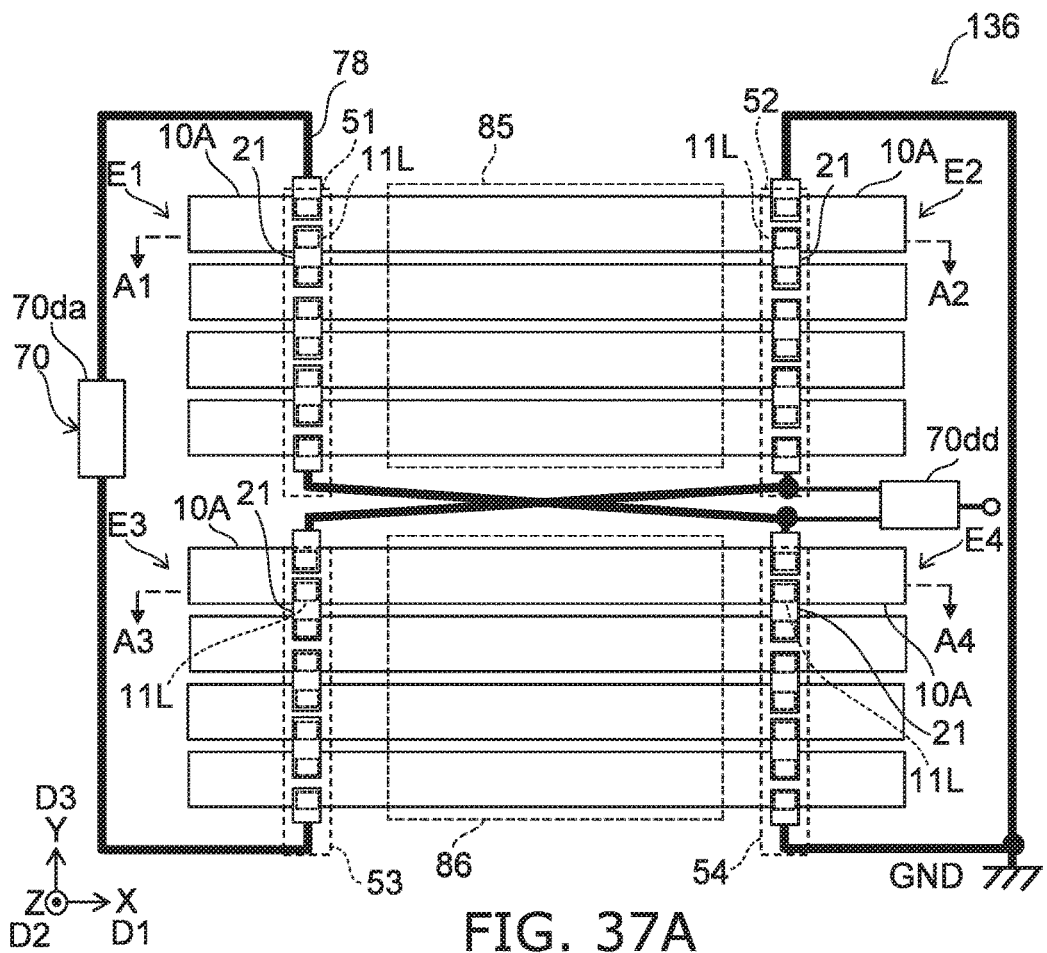
FIG. 37A to FIG. 37C are schematic views illustrating a magnetic sensor according to the fourth embodiment.
Figure 37B:
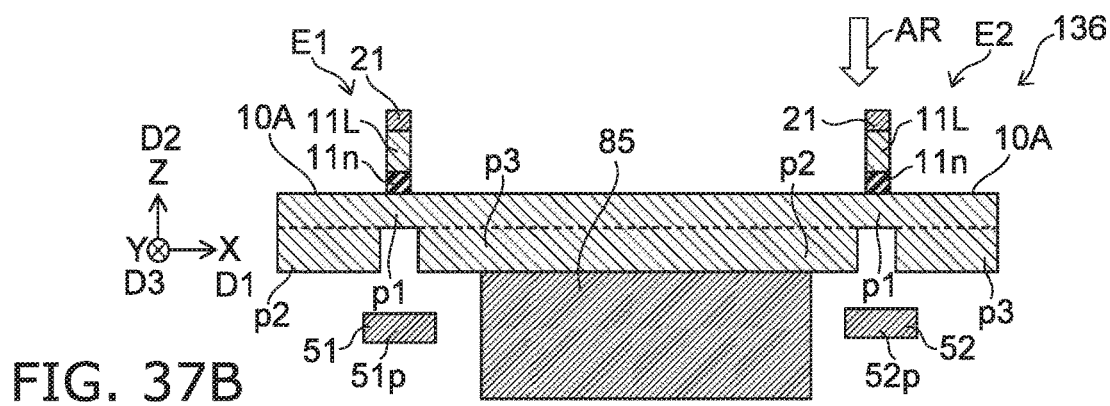
Figure 37C:
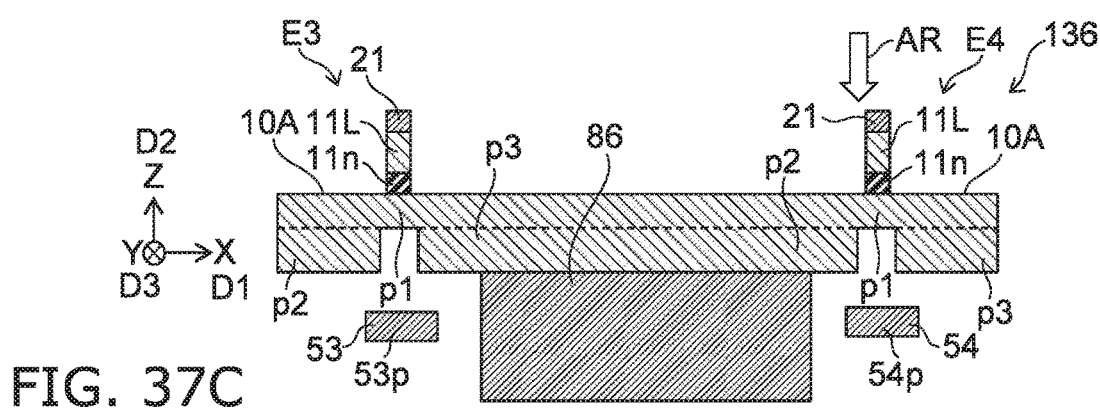
Figure 38:
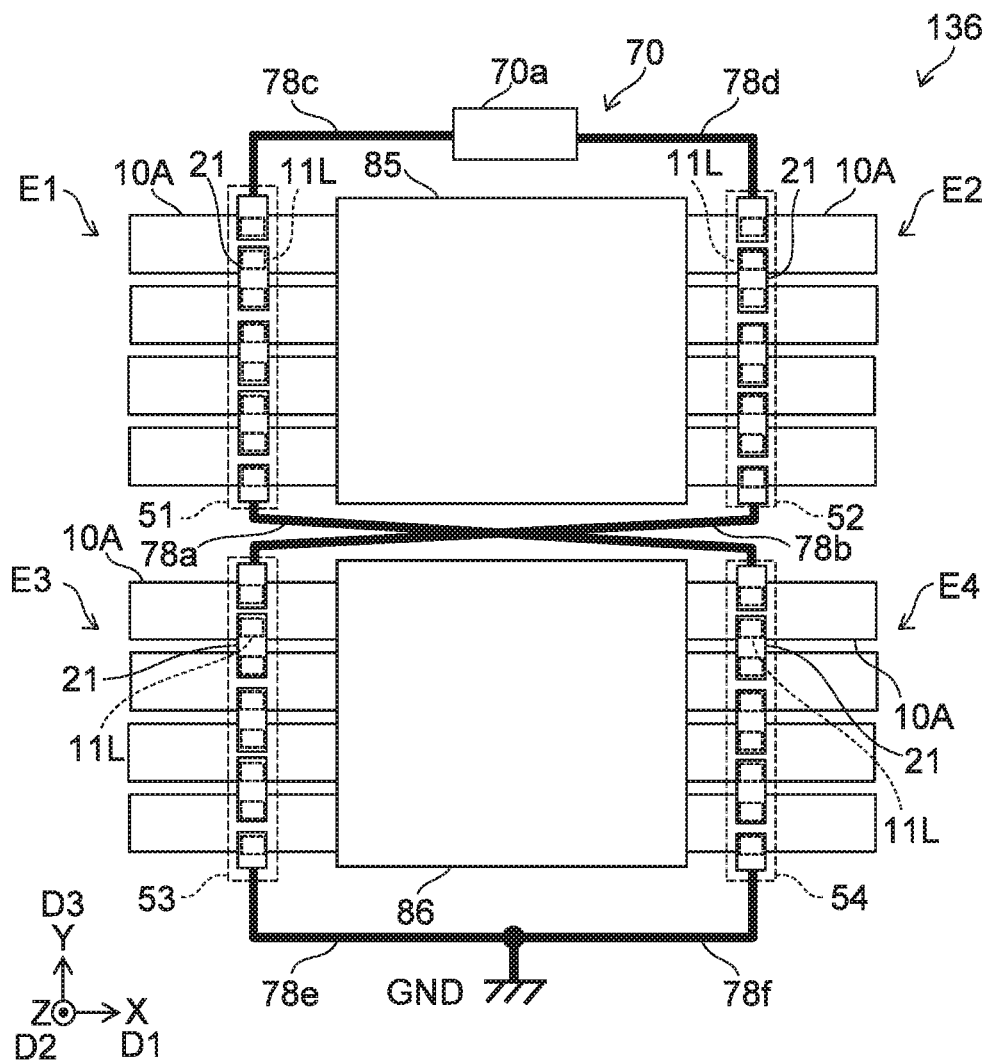
FIG. 38 is a schematic view illustrating the magnetic sensor according to the fourth embodiment.

FIG. 37A and FIG. 38 are plan views when viewed along arrow AR of FIG. 37B and FIG. 37C. FIG. 37B is a line A1-A2 cross-sectional view of FIG. 37A. FIG. 37C is a line A3-A4 cross-sectional view of FIG. 37A.

As shown in FIG. 37A to FIG. 37C, the magnetic sensor 136 according to the embodiment also includes the first element E1, the second element E2, the third element E3, the fourth element E4, the first magnetic section 85, and the second magnetic section 86. The positions of the first magnetic section 85 and the second magnetic section 86 of the magnetic sensor 136 are different from those of the magnetic sensor 135. Otherwise, the configuration of the magnetic sensor 136 may be the same as the configuration of the magnetic sensor 135.

In the magnetic sensor 136 as shown in FIG. 37B and FIG. 37C, the first magnetic section 85 is between the first interconnect 51 and the second interconnect 52 in the first direction D1. The second magnetic section 86 is between the third interconnect 53 and the fourth interconnect 54 in the first direction D1.

In the magnetic sensor 136 as shown in FIG. 38 as well, an alternating current is supplied to the first to fourth interconnects 51 to 54; and the first to fourth elements E1 to E4 have a bridge connection. The noise can be reduced further thereby. The sensitivity can be increased further.

In the magnetic sensors 135 and 136 as well, a magnetic sensor can be provided in which the sensitivity can be increased. The first to fourth interconnects 51 to 54 are provided proximally to the first magnetic section 85 and the second magnetic section 86. For example, the magnetic field that is due to the current flowing in the first interconnect 51 and the second interconnect 52 is applied to the first magnetic section 85. For example, the magnetic field that is due to the current flowing in the third interconnect 53 and the fourth interconnect 54 is applied to the second magnetic section 86. The first to fourth interconnects 51 to 54 respectively may not overlap the first to fourth elements E1 to E4 in the second direction D2.

FIG. 39A to FIG. 39D are schematic views illustrating a magnetic sensor according to the fourth embodiment.

FIG. 39A is a plan view as viewed along arrow AR of FIG. 39C and FIG. 39D. FIG. 39B is a line B1-B2 cross-sectional view of FIG. 39A. FIG. 39C is a line A1-A2 cross-sectional view of FIG. 39A. FIG. 39D is a line A3-A4 cross-sectional view of FIG. 39A.

As shown in FIG. 39A to FIG. 39D, the magnetic sensor 137a according to the embodiment includes the first structure body 81. The first structure body 81 includes the first magnetic part 10A, the second magnetic part 10B, the first magnetic layer 11L, the first nonmagnetic portion 11n, and the second nonmagnetic portion 12n.

The configurations of the first magnetic part 10A and the second magnetic part 10B of the magnetic sensor 133 are applicable to the first magnetic part 10A and the second magnetic part 10B of the magnetic sensor 137a.

As shown in FIG. 39B and FIG. 39C, for example, the direction from a portion of the first portion p1 toward the portion 11Lp of the first magnetic layer 11L is aligned with the second direction D2. As shown in FIG. 39B and FIG. 39D, for example, the direction from a portion of the fourth portion p4 toward the other portion 11Lq of the first magnetic layer 11L is aligned with the second direction D2.

The first nonmagnetic portion 11n is provided between the portion of the first portion p1 recited above and the portion 11Lp of the first magnetic layer 11L recited above. The second nonmagnetic portion 12n is provided between the portion of the fourth portion p4 recited above and the other portion 11Lq of the first magnetic layer 11L recited above.

The portion of the first portion p1 recited above, the portion 11Lp of the first magnetic layer 11L recited above, and the first nonmagnetic portion 11n are included in one element. The portion of the fourth portion p4 recited above, the other portion 11Lq of the first magnetic layer 11L recited above, and the second nonmagnetic portion 12n are included in another one element. The electrical resistances of these elements can change according to an external magnetic field. These elements are connected in series by the first magnetic layer 11L. The effects of the noise can be suppressed. A magnetic sensor can be provided in which the sensitivity can be increased further.

FIG. 40A to FIG. 40D are schematic views illustrating a magnetic sensor according to the fourth embodiment.

FIG. 40A is a plan view as viewed along arrow AR of FIG. 40C and FIG. 40D. FIG. 40B is a line B1-B2 cross-sectional view of FIG. 40A. FIG. 40C is a line A1-A2 cross-sectional view of FIG. 40A. FIG. 40D is a line A3-A4 cross-sectional view of FIG. 40A.

As shown in FIG. 40A to FIG. 40D, the magnetic sensor 137b according to the embodiment also includes the first structure body 81. The configurations of the first magnetic part 10A and the second magnetic part 10B of the magnetic sensor 137b are different from those of the magnetic sensor 137a. Otherwise, the configuration of the magnetic sensor 137b is similar to the configuration of the magnetic sensor 137a.

In the example as shown in FIG. 40A and FIG. 40C, the second portion p2 has the third length L3 along the second direction D2 that is longer than the first length L1, and the fourth length L4 along the third direction D3 that is longer than the second length L2. The third portion p3 has the fifth length L5 along the second direction D2 that is longer than the first length L1, and the sixth length L6 along the third direction D3 that is longer than the second length L2.

The fifth portion p5 has the ninth length L9 along the second direction D2 that is longer than the seventh length L7, and the tenth length L10 along the third direction D3 that is longer than the eighth length L8. The sixth portion p6 has the eleventh length L11 along the second direction D2 that is longer than the seventh length L7, and the twelfth length L12 along the third direction D3 that is longer than the eighth length L8.

Figure 41:
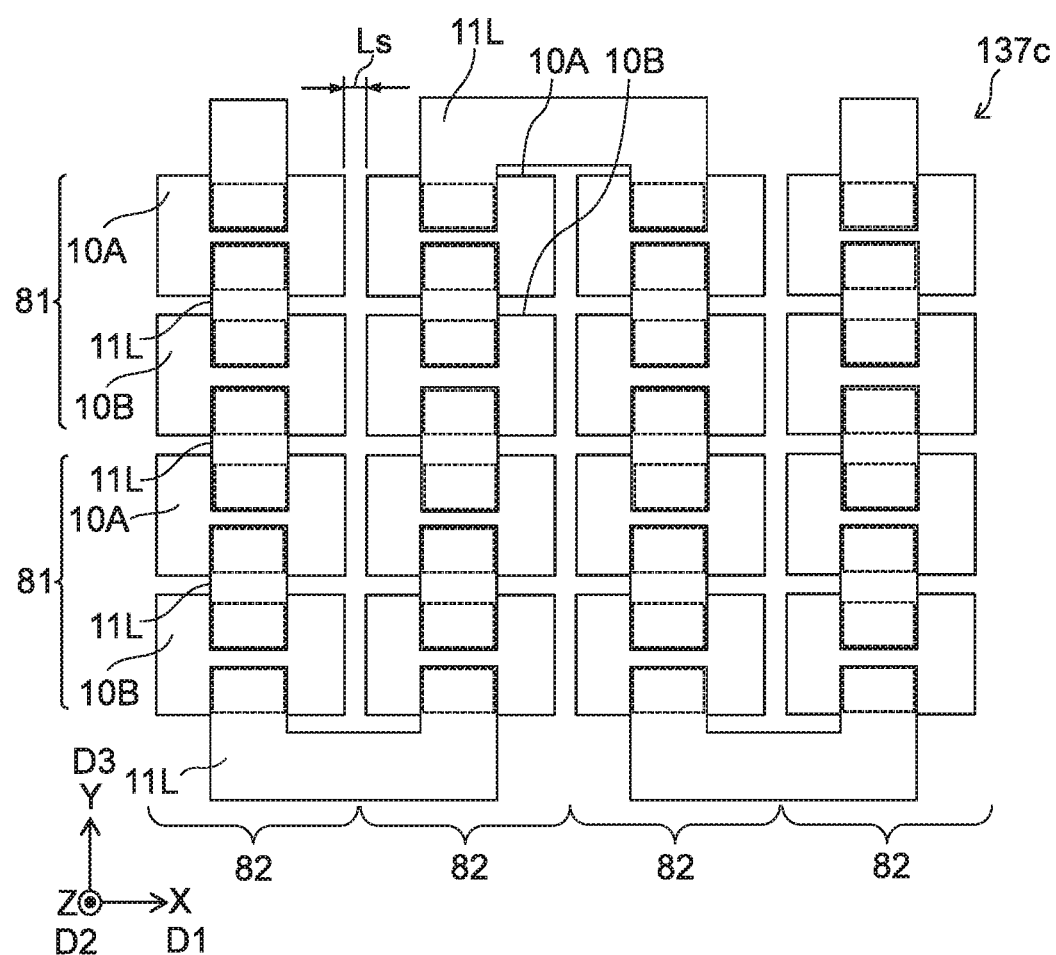
FIG. 41 is a schematic plan view illustrating a magnetic sensor according to the fourth embodiment.

FIG. 41 is a schematic plan view illustrating a magnetic sensor according to the fourth embodiment.

As shown in FIG. 41, the magnetic sensor 137c according to the embodiment includes the multiple second structure bodies 82. For example, one of the multiple second structure bodies 82 includes the multiple first structure bodies 81. The multiple first structure bodies 81 are arranged along the third direction D3.

The first magnetic part 10A of one of the multiple first structure bodies 81 and the second magnetic part 10B of another one of the multiple first structure bodies 81 are electrically connected to each other. For example, the electrical connection is performed by one of the multiple first magnetic layers 11L. The other one of the multiple first structure bodies 81 is next to the one of the multiple first structure bodies 81.

The multiple second structure bodies 82 are arranged along the first direction D1. One of the multiple second structure bodies 82 and another one of the multiple second structure bodies 82 are electrically connected to each other. For example, the electrical connection is performed by one of the multiple first magnetic layers 11L.

In the magnetic sensor 137c, it is favorable for the distance Ls to be shorter than at least one of the third length L3 or the fifth length L5.

Figure 42A:
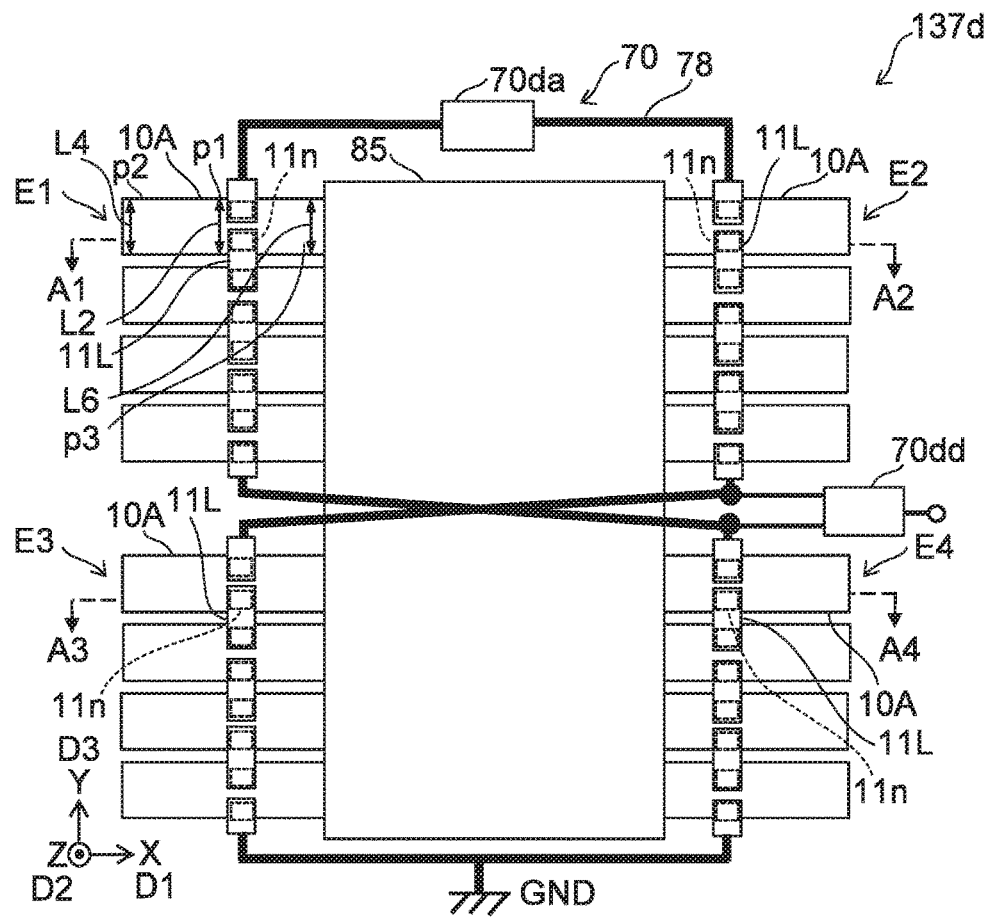
FIG. 42A to FIG. 42C are schematic views illustrating a magnetic sensor according to the fourth embodiment.
Figure 42B:
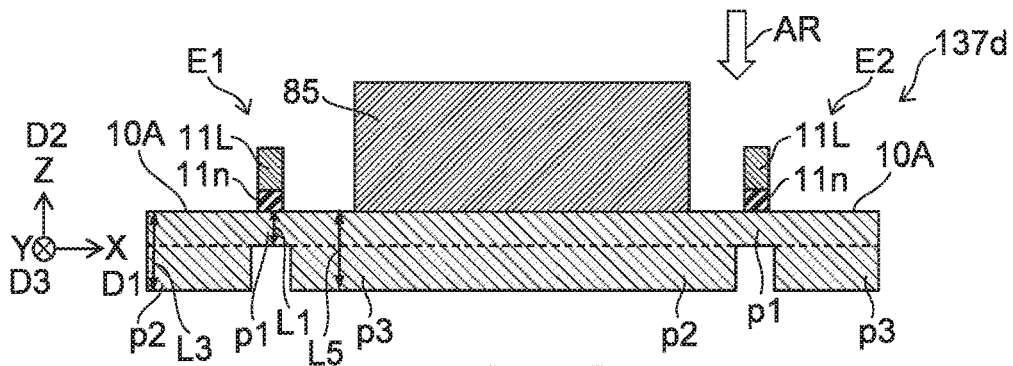
Figure 42C:
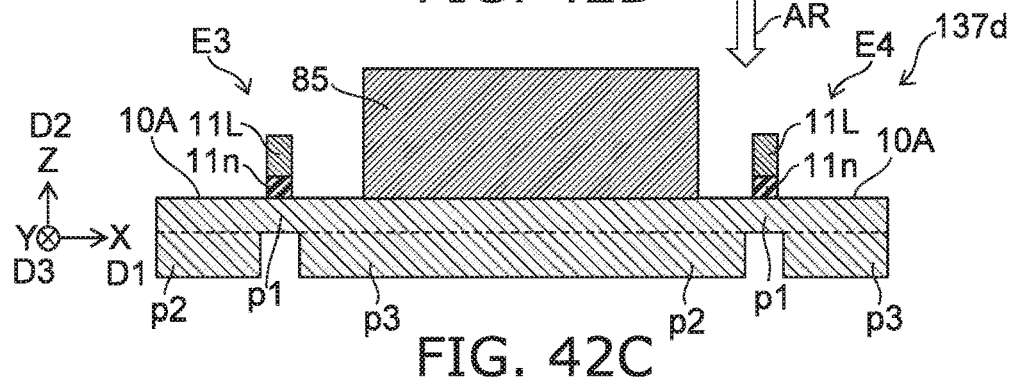

FIG. 42A to FIG. 42C are schematic views illustrating a magnetic sensor according to the fourth embodiment.

FIG. 42A is a plan view as viewed along arrow AR of FIG. 42B and FIG. 42C. FIG. 42B is a line A1-A2 cross-sectional view of FIG. 42A. FIG. 42C is a line A3-A4 cross-sectional view of FIG. 42A.

As shown in FIG. 42A to FIG. 42C, the magnetic sensor 137d according to the embodiment includes the first element E1, the second element E2, the third element E3, the fourth element E4, and the first magnetic section 85. Each of the first element E1, the second element E2, the third element E3, and the fourth element E4 includes the first magnetic part 10A, the first magnetic layer 11L, and the first nonmagnetic portion 11n.

The configurations of the first magnetic part 10A and the second magnetic part 10B of the magnetic sensor 133 are applicable to the first magnetic part 10A and the second magnetic part 10B of the magnetic sensor 137d.

As shown in FIG. 42B, the direction from the third portion p3 of the first magnetic part 10A of the first element E1 toward a portion of the first magnetic section 85 is aligned with the second direction D2. The direction from the second portion p2 of the first magnetic part 10A of the second element E2 toward a portion of the first magnetic section 85 is aligned with the second direction D2.

As shown in FIG. 42C, the direction from the third portion p3 of the first magnetic part 10A of the third element E3 toward a portion of the first magnetic section 85 is aligned with the second direction D2. The direction from the second portion p2 of the first magnetic part 10A of the fourth element E4 toward a portion of the first magnetic section 85 is aligned with the second direction D2.

Figure 43A:
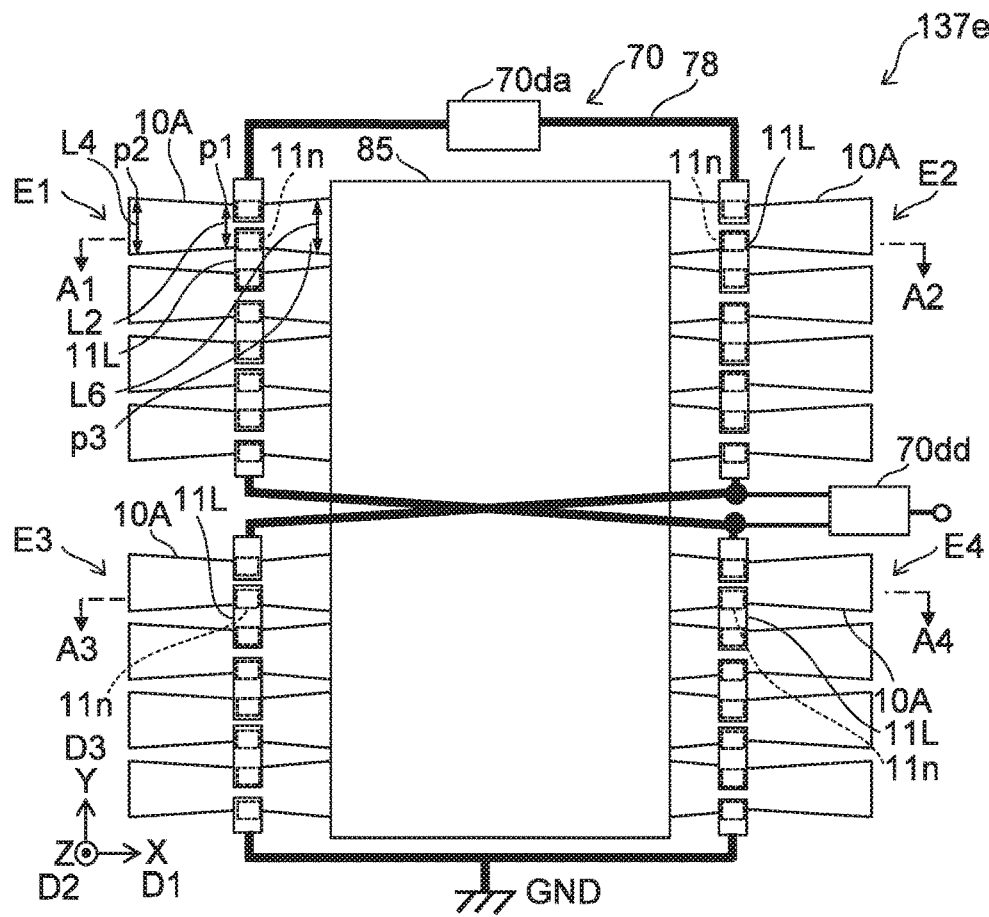
FIG. 43A to FIG. 43C are schematic views illustrating a magnetic sensor according to the fourth embodiment.
Figure 43B:
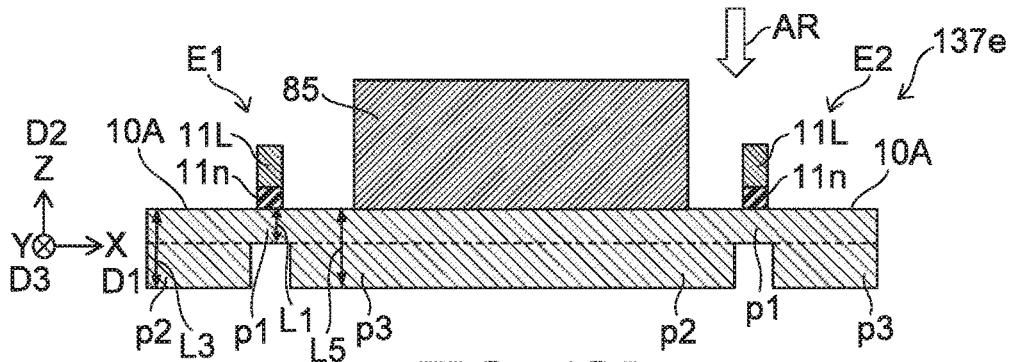
Figure 43C:
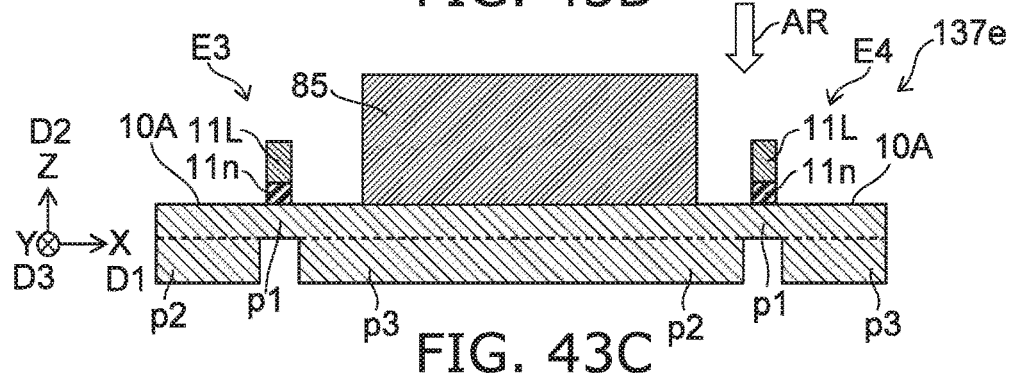

FIG. 43A to FIG. 43C are schematic views illustrating a magnetic sensor according to the fourth embodiment.

FIG. 43A is a plan view as viewed along arrow AR of FIG. 43B and FIG. 43C. FIG. 43B is a line A1-A2 cross-sectional view of FIG. 43A. FIG. 43C is a line A3-A4 cross-sectional view of FIG. 43A.

As shown in FIG. 43A to FIG. 43C, the magnetic sensor 137e according to the embodiment also includes the first element E1, the second element E2, the third element E3, the fourth element E4, and the first magnetic section 85. The configuration of the first magnetic part 10A of the magnetic sensor 137e is different from that of the magnetic sensor 137d. Otherwise, the configuration of the magnetic sensor 137e may be the same as the configuration of the magnetic sensor 137d.

In the magnetic sensor 137e as shown in FIG. 43A and FIG. 43B, the second portion p2 has the third length L3 along the second direction D2 that is longer than the first length L1, and the fourth length L4 along the third direction D3 that is longer than the second length L2. The third portion p3 has the fifth length L5 along the second direction D2 that is longer than the first length L1, and the sixth length L6 along the third direction D3 that is longer than the second length L2.

In the magnetic sensors 137a to 137e as well, a magnetic sensor can be provided in which the sensitivity can be increased.

As in the magnetic sensor 137a, the first conductive member 21 may not be provided in one element in at least one of the magnetic sensor 135 or the magnetic sensor 136. As in the magnetic sensor 137a, one element may include a portion of the first portion p1, the portion 11Lp of the first magnetic layer 11L, and the first nonmagnetic portion 11n in at least one of the magnetic sensor 135 or the magnetic sensor 136. As in the magnetic sensor 137a, one element may include a portion of the fourth portion p4, the portion 11Lq of the first magnetic layer 11L, and the second nonmagnetic portion 12n. In such a magnetic sensor as well, a magnetic sensor can be provided in which the sensitivity can be increased.

Figure 44:
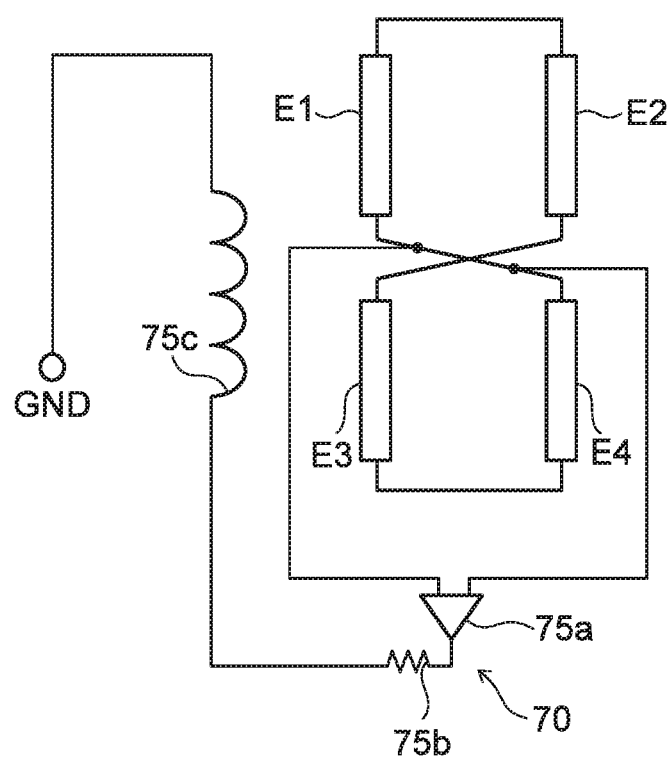
FIG. 44 is a schematic view illustrating a magnetic sensor according to the fourth embodiment.

FIG. 44 is a schematic view illustrating a magnetic sensor according to the fourth embodiment.

FIG. 44 illustrates the configuration of a portion of the circuit part 70. In the example, the first element E1 and the fourth element E4 are connected electrically in series. The second element E2 and the third element E3 are connected electrically in series. The potential difference between the connection point between the first element E1 and the fourth element E4 and the connection point between the second element E2 and the third element E3 is input to an amplifier 75a. The amplifier 75a is, for example, a differential amplifier. The output of the amplifier 75a is electrically connected to the ground GND via a resistance 75b and an inductor 75c. For example, the inductor 75c corresponds to the first to fourth interconnects 54, etc. Such a circuit is, for example, a negative feedback circuit. By using such a circuit, the detection of the magnetic field which is the detection object is possible in a state in which the feedback of the change of the characteristics of these elements, e.g., the fluctuation of the operating points of the first to fourth elements E1 to E4 due to the magnetic field, is suppressed. For example, the operating point fluctuation of the elements is suppressed; and a stable detection output is obtained. Such a circuit is applicable to any magnetic sensor recited above.

The magnetic sensors 130 to 136 and 137a to 137e may be included in a diagnostic device 500. The diagnostic device 500 according to the embodiment includes the magnetic sensor according to the fourth embodiment, and a processor processing an output signal obtained from the magnetic sensor. The processor includes, for example, at least one of a signal processor 508 or a data processor 512. The processor includes, for example, a computer, etc.

The embodiments may include the following configurations (e.g., technological proposals).

Configuration A12

A magnetic sensor, comprising a first structure body, the first structure body including:

a first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length;

a second magnetic part including a fourth portion, a fifth portion, and a sixth portion, a direction from the fifth portion toward the sixth portion being aligned with the first direction, the fourth portion being between the fifth portion and the sixth portion in the first direction, the fourth portion having a seventh length along the second direction and an eighth length along the third direction, the fifth portion having at least one of a ninth length along the second direction or a tenth length along the third direction, the ninth length being longer than the seventh length, the tenth length being longer than the eighth length, the sixth portion having at least one of an eleventh length along the second direction or a twelfth length along the third direction, the eleventh length being longer than the seventh length, the twelfth length being longer than the eighth length;

a first conductive member, a direction from a portion of the first portion toward a portion of the first conductive member being aligned with the second direction, a direction from a portion of the fourth portion toward an other portion of the first conductive member being aligned with the second direction;

a first magnetic layer provided between the portion of the first portion and the portion of the first conductive member;

a second magnetic layer provided between the portion of the fourth portion and the other portion of the first conductive member;

a first nonmagnetic portion provided between the first magnetic layer and the portion of the first portion; and a second nonmagnetic portion provided between the second magnetic layer and the portion of the fourth portion.

Configuration A13

The magnetic sensor according to Configuration A12, further comprising a first interconnect, at least a portion of the first interconnect being along the third direction.

Configuration A14

The magnetic sensor according to Configuration A12 or A13, comprising a plurality of the first structure bodies, the plurality of first structure bodies being arranged along the third direction, the first magnetic part of one of the plurality of first structure bodies and the second magnetic part of an other one of the plurality of first structure bodies being electrically connected to each other.

Configuration A15

The magnetic sensor according to Configuration A12, further comprising a plurality of second structure bodies, one of the plurality of second structure bodies including a plurality of the first structure bodies, the plurality of first structure bodies being arranged along the third direction, the first magnetic part of one of the plurality of first structure bodies and the second magnetic part of an other one of the plurality of first structure bodies being electrically connected to each other, the plurality of second structure bodies being arranged along the first direction, one of the plurality of second structure bodies and an other one of the plurality of second structure bodies being electrically connected to each other.

Configuration A16

The magnetic sensor according to Configuration A15, wherein a distance along the first direction between the first magnetic part of one of the plurality of first structure bodies included in the one of the plurality of second structure bodies and the first magnetic part of an other one of the plurality of first structure bodies included in the other one of the plurality of second structure bodies is shorter than at least one of the third length or the fifth length.

Configuration A17

A magnetic sensor, comprising:
a first element;
a second element;
a third element;
a fourth element; and
a first magnetic section, each of the first element, the second element, the third element, and the fourth element including a first magnetic part, a first conductive member, and a first magnetic layer, the first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length, the first magnetic layer being between at least a portion of the first portion and at least a portion of the first conductive member in the second direction, a direction from the first element toward the second element being aligned with the first direction, a direction from the third element toward the fourth element being aligned with the first direction, a direction from the third portion of the first magnetic part of the first element toward a portion of the first magnetic section being aligned with the second direction, a direction from the second portion of the first magnetic part of the second element toward a portion of the first magnetic section being aligned with the second direction, a direction from the third portion of the first magnetic part of the third element toward a portion of the first magnetic section being aligned with the second direction, a direction from the second portion of the first magnetic part of the fourth element toward a portion of the first magnetic section being aligned with the second direction, the first conductive member of the first element being electrically connected to the first conductive member of the fourth element, the first conductive member of the second element being electrically connected to the first conductive member of the third element.

Configuration A18

The magnetic sensor according to Configuration A17, further comprising a circuit part, the circuit part being configured to supply a current to the first element, the second element, the third element, and the fourth element, an orientation of the current flowing through the first conductive member of the first element includes a component having a same orientation as the current flowing through the first conductive member of the second element, the orientation of the current flowing through the first conductive member of the first element includes a component having a same orientation as the current flowing through the first conductive member of the fourth element, an orientation of the current flowing through the first conductive member of the third element includes a component having the same orientation as the current flowing through the first conductive member of the second element.

Configuration A19

A magnetic sensor, comprising:
a first element;
a second element;
a third element;
a fourth element;
a first magnetic section; and
a second magnetic section, each of the first element, the second element, the third element, and the fourth element including a first magnetic part, a first conductive member, and a first magnetic layer, the first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length, the first magnetic layer being between at least a portion of the first portion and at least a portion of the first conductive member in the second direction, a direction from the first element toward the second element being aligned with the first direction, a direction from the third element toward the fourth element being aligned with the first direction, a direction from the third portion of the first magnetic part of the first element toward a portion of the first magnetic section being aligned with the second direction, a direction from the second portion of the first magnetic part of the second element toward a portion of the first magnetic section being aligned with the second direction, a direction from the third portion of the first magnetic part of the third element toward a portion of the second magnetic section being aligned with the second direction, a direction from the second portion of the first magnetic part of the fourth element toward a portion of the second magnetic section being aligned with the second direction, the first conductive member of the first element being electrically connected to the first conductive member of the fourth element, the first conductive member of the second element being electrically connected to the first conductive member of the third element.

Configuration A20

The magnetic sensor according to Configuration A17, further comprising a circuit part, the circuit part being configured to supply a current to the first element, the second element, the third element, and the fourth element, an orientation of the current flowing through the first conductive member of the first element includes a reverse component of an orientation of the current flowing through the first conductive member of the second element, the orientation of the current flowing through the first conductive member of the first element includes a component having a same orientation as the current flowing through the first conductive member of the fourth element, an orientation of the current flowing through the first conductive member of the third element includes a component having the same orientation as the current flowing through the first conductive member of the second element.

Configuration A21

The magnetic sensor according to Configuration A20, further comprising:

a first interconnect;

a second interconnect;

a third interconnect;

a fourth interconnect; and a current supply circuit, one end of the first interconnect being electrically connected to one end of the fourth interconnect, one end of the second interconnect being electrically connected to one end of the third interconnect, the current supply circuit being configured to supply an alternating current to a current path including the first interconnect and the fourth interconnect, and supplying an alternating current to a current path including the second interconnect and the third interconnect.

Configuration A22

A magnetic sensor, comprising a first structure body, the first structure body including:

a first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length;

a second magnetic part including a fourth portion, a fifth portion, and a sixth portion, a direction from the fifth portion toward the sixth portion being aligned with the first direction, the fourth portion being between the fifth portion and the sixth portion in the first direction, the fourth portion having a seventh length along the second direction and an eighth length along the third direction, the fifth portion having at least one of a ninth length along the second direction or a tenth length along the third direction, the ninth length being longer than the seventh length, the tenth length being longer than the eighth length, the sixth portion having at least one of an eleventh length along the second direction or a twelfth length along the third direction, the eleventh length being longer than the seventh length, the twelfth length being longer than the eighth length;

a first magnetic layer, a direction from a portion of the first portion toward a portion of the first magnetic layer being aligned with the second direction, a direction from a portion of the fourth portion toward an other portion of the first magnetic layer being aligned with the second direction;

a first nonmagnetic portion provided between the portion of the first portion and the portion of the first magnetic layer; and a second nonmagnetic portion provided between the portion of the fourth portion and the other portion of the first magnetic layer.

Configuration A23

The magnetic sensor according to Configuration A22, further comprising a first interconnect, at least a portion of the first interconnect being along the third direction.

Configuration A24

The magnetic sensor according to Configuration A22 or A23, comprising a plurality of the first structure bodies, the plurality of first structure bodies being arranged along the third direction, the first magnetic part of one of the plurality of first structure bodies and the second magnetic part of an other one of the plurality of first structure bodies being electrically connected to each other.

Configuration A25

The magnetic sensor according to Configuration A22, further comprising a plurality of second structure bodies, one of the plurality of second structure bodies including a plurality of the first structure bodies, the plurality of first structure bodies being arranged along the third direction, the first magnetic part of one of the plurality of first structure bodies and the second magnetic part of an other one of the plurality of first structure bodies being electrically connected to each other, the plurality of second structure bodies being arranged along the first direction, one of the plurality of second structure bodies and an other one of the plurality of second structure bodies being electrically connected to each other, a distance along the first direction between the first magnetic part of one of the plurality of first structure bodies included in the one of the plurality of second structure bodies and the first magnetic part of an other one of the plurality of first structure bodies included in the other one of the plurality of second structure bodies being shorter than at least one of the third length or the fifth length.

Configuration A26

A magnetic sensor, comprising:
a first element;
a second element;
a third element;
a fourth element; and
a magnetic section, each of the first element, the second element, the third element, and the fourth element including a first magnetic part, a first magnetic layer, and a first nonmagnetic portion, the first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length, the first nonmagnetic portion being between at least a portion of the first portion and at least a portion of the first magnetic layer in the second direction, a direction from the first element toward the second element being aligned with the first direction, a direction from the third element toward the fourth element being aligned with the first direction, a direction from the third portion of the first magnetic part of the first element toward a portion of the magnetic section being aligned with the second direction, a direction from the second portion of the first magnetic part of the second element toward a portion of the magnetic section being aligned with the second direction, a direction from the third portion of the first magnetic part of the third element toward a portion of the magnetic section being aligned with the second direction, a direction from the second portion of the first magnetic part of the fourth element toward a portion of the magnetic section being aligned with the second direction, the first magnetic layer of the first element being electrically connected to the first magnetic layer of the fourth element, the first magnetic layer of the second element being electrically connected to the first magnetic layer of the third element.

Configuration A27

A magnetic sensor, comprising:
a first element;
a second element;
a third element;
a fourth element;
a first magnetic section; and
a second magnetic section, each of the first element, the second element, the third element, and the fourth element including a first magnetic part, a first conductive member, and a first magnetic layer, the first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length, the first magnetic layer being between at least a portion of the first portion and at least a portion of the first conductive member in the second direction, a direction from the first element toward the second element being aligned with the first direction, a direction from the third element toward the fourth element being aligned with the first direction, a direction from the third portion of the first magnetic part of the first element toward a portion of the first magnetic section being aligned with the second direction, a direction from the second portion of the first magnetic part of the second element toward a portion of the first magnetic section being aligned with the second direction, a direction from the third portion of the first magnetic part of the third element toward a portion of the second magnetic section being aligned with the second direction, a direction from the second portion of the first magnetic part of the fourth element toward a portion of the second magnetic section being aligned with the second direction, the first magnetic layer of the first element being electrically connected to the first magnetic layer of the fourth element, the first magnetic layer of the second element being electrically connected to the first magnetic layer of the third element.

Configuration A28

The magnetic sensor according to Configuration A27, further comprising:
a first interconnect;
a second interconnect;
a third interconnect;
a fourth interconnect; and
a current supply circuit.

Configuration A29

A diagnostic device, comprising:
the magnetic sensor according to any one of Configurations A12 to A28; and
a processor processing an output signal obtained from the magnetic sensor.

According to the embodiments, a magnetic sensor and a diagnostic device can be provided in which the sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as magnetic layers, nonmagnetic portions, interconnects, resistance portions, circuit parts, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, and diagnostic devices practicable by an appropriate design modification by one skilled in the art based on the magnetic sensors, and the diagnostic devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising a first element, the first element including:
    a first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length;
    a first magnetic layer, a direction from the first portion toward the first magnetic layer being aligned with the second direction;
    a first nonmagnetic portion provided between the first portion and the first magnetic layer; and
    a first intermediate magnetic layer provided between the first portion and the first nonmagnetic portion.

2. The magnetic sensor according to claim 1, further comprising:
    a first interconnect including a portion extending along the third direction and overlapping at least a portion of the first portion in the second direction,
    a magnetization of the first magnetic layer being aligned with the third direction.

3. The magnetic sensor according to claim 1, further comprising:
    a first interconnect including a portion extending along the third direction and overlapping at least a portion of the first portion in the second direction,
    an electrical resistance between the first magnetic part and the first magnetic layer has an even-function characteristic of a magnetic field applied to the first element.

4. The magnetic sensor according to claim 1, further comprising:
    a first interconnect including a portion extending along the third direction and overlapping at least a portion of the first portion in the second direction,
    an electrical resistance between the first magnetic part and the first magnetic layer having a first value when a first magnetic field is applied to the first element, having a second value when a second magnetic field is applied to the first element, and having a third value when a third magnetic field is applied to the first element,
    an absolute value of the first magnetic field being less than an absolute value of the second magnetic field and less than an absolute value of the third magnetic field,
    an orientation of the second magnetic field being the reverse of an orientation of the third magnetic field, and
    the first value being less than the second value and less than the third value.

5. The magnetic sensor according to claim 3, further comprising a circuit part,
    the circuit part including:
        a current supply circuit configured to supply an alternating current to the first interconnect; and
        a detection circuit configured to detect a value corresponding to the electrical resistance.

6. The magnetic sensor according to claim 1, further comprising a second element, a third element, and a fourth element,
    the first element further including the first interconnect including a portion extending along the third direction,
    the second element including a second magnetic part, a second magnetic layer, a second nonmagnetic portion, a second intermediate magnetic layer, and a second interconnect,
    the second magnetic part including a fourth portion, a fifth portion, and a sixth portion, a direction from the fifth portion toward the sixth portion being aligned with a fourth direction, the fourth portion being between the fifth portion and the sixth portion in the fourth direction, the fourth portion having a seventh length and an eighth length, the seventh length being along a fifth direction crossing the fourth direction, the eighth length being along a sixth direction crossing a plane including the fourth direction and the fifth direction, the fifth portion having at least one of a ninth length along the fifth direction or a tenth length along the sixth direction, the ninth length being longer than the seventh length, the tenth length being longer than the eighth length, the sixth portion having at least one of an eleventh length along the fifth direction or a twelfth length along the sixth direction, the eleventh length being longer than the seventh length, the twelfth length being longer than the eighth length, a direction from the fourth portion toward the second magnetic layer being aligned with the fifth direction, the second nonmagnetic portion being provided between the fourth portion and the second magnetic layer, the second intermediate magnetic layer being provided between the fourth portion and the second nonmagnetic portion, the second interconnect including a portion extending along the sixth direction, the third element including a third magnetic part, a third magnetic layer, a third nonmagnetic portion, a third intermediate magnetic layer, and a third interconnect, the third magnetic part including a seventh portion, an eighth portion, and a ninth portion, a direction from the eighth portion toward the ninth portion being aligned with a seventh direction, the seventh portion being between the eighth portion and the ninth portion in the seventh direction, the seventh portion having a thirteenth length and a fourteenth length, the thirteenth length being along an eighth direction crossing the seventh direction, the fourteenth length being along a ninth direction crossing a plane including the seventh direction and the eighth direction, the eighth portion having at least one of a fifteenth length along the eighth direction or a sixteenth length along the ninth direction, the fifteenth length being longer than the thirteenth length, the sixteenth length being longer than the fourteenth length, the ninth portion having at least one of a seventeenth length along the eighth direction or an eighteenth length along the ninth direction, the seventeenth length being longer than the thirteenth length, the eighteenth length being longer than the fourteenth length, a direction from the seventh portion toward the third magnetic layer being aligned with the eighth direction, the third nonmagnetic portion being provided between the seventh portion and the third magnetic layer, the third intermediate magnetic layer being provided between the seventh portion and the third nonmagnetic portion, the third interconnect including a portion extending along the ninth direction, the fourth element including a fourth magnetic part, a fourth magnetic layer, a fourth nonmagnetic portion, a fourth intermediate magnetic layer, and a fourth interconnect, the fourth magnetic part including a tenth portion, an eleventh portion, and a twelfth portion, a direction from the eleventh portion toward the twelfth portion being aligned with a tenth direction, the tenth portion being between the eleventh portion and the twelfth portion in the tenth direction, the tenth portion having a nineteenth length and a twentieth length, the nineteenth length being along an eleventh direction crossing the tenth direction, the twentieth length being along a twelfth direction crossing a plane including the seventh direction and the eighth direction, the eleventh portion having at least one of a twenty-first length along the eleventh direction or a twenty-second length along the twelfth direction, the twenty-first length being longer than the nineteenth length, the twenty-second length being longer than the twentieth length, the twelfth portion having at least one of a twenty-third length along the eleventh direction or a twenty-fourth length along the twelfth direction, the twenty-third length being longer than the nineteenth length, the twenty-fourth length being longer than the twentieth length, a direction from the tenth portion toward the fourth magnetic layer being aligned with the eleventh direction, the fourth nonmagnetic portion being provided between the tenth portion and the fourth magnetic layer, the fourth intermediate magnetic layer being provided between the tenth portion and the fourth nonmagnetic portion, the fourth interconnect including a portion extending along the twelfth direction.

7. The magnetic sensor according to claim 6, further comprising a circuit part, the circuit part including a current supply circuit, the current supply circuit being configured to supply a first alternating current to the first interconnect, configured to supply a second alternating current to the second interconnect, configured to supply a third alternating current to the third interconnect, and configured to supply a fourth alternating current to the fourth interconnect, an orientation of a first current magnetic field having a reverse component of an orientation of a second current magnetic field and having a reverse component of an orientation of a third current magnetic field, the first current magnetic field being generated by the first alternating current and applied to the first portion, the second current magnetic field being generated by the second alternating current and applied to the fourth portion, the third current magnetic field being generated by the third alternating current and applied to the seventh portion, an orientation of a fourth current magnetic field having the reverse component of the orientation of the second current magnetic field and having the reverse component of the orientation of the third current magnetic field, the fourth current magnetic field being generated by the fourth alternating current and applied to the tenth portion.

8. The magnetic sensor according to claim 7, wherein the circuit part further includes a detection circuit, the detection circuit being configured to output a signal corresponding to a potential difference between a first connection point and a second connection point, a first current path and a third current path are electrically connected to each other in series at the first connection point, the first current path including the first magnetic part and the first magnetic layer, the third current path including the third magnetic part and the third magnetic layer, and a second current path and a fourth current path are electrically connected to each other in series at the second connection point, the second current path including the second magnetic part and the second magnetic layer, the fourth current path including the fourth magnetic part and the fourth magnetic layer.

9. A diagnostic device, comprising:
the magnetic sensor according to claim 1; and
a processor configured to process an output signal obtained from the magnetic sensor.

10. A magnetic sensor, comprising a first structure body, the first structure body including:
- a first magnetic part including a first portion, a second portion, and a third portion, a direction from the second portion toward the third portion being aligned with a first direction, the first portion being between the second portion and the third portion in the first direction, the first portion having a first length and a second length, the first length being along a second direction crossing the first direction, the second length being along a third direction crossing a plane including the first direction and the second direction, the second portion having at least one of a third length along the second direction or a fourth length along the third direction, the third length being longer than the first length, the fourth length being longer than the second length, the third portion having at least one of a fifth length along the second direction or a sixth length along the third direction, the fifth length being longer than the first length, the sixth length being longer than the second length;
- a second magnetic part including a fourth portion, a fifth portion, and a sixth portion, a direction from the fifth portion toward the sixth portion being aligned with the first direction, the fourth portion being between the fifth portion and the sixth portion in the first direction, the fourth portion having a seventh length along the second direction and an eighth length along the third direction, the fifth portion having at least one of a ninth length along the second direction or a tenth length along the third direction, the ninth length being longer than the seventh length, the tenth length being longer than the eighth length, the sixth portion having at least one of an eleventh length along the second direction or a twelfth length along the third direction, the eleventh length being longer than the seventh length, the twelfth length being longer than the eighth length;
- a first conductive member, a direction from a portion of the first portion toward a portion of the first conductive member being aligned with the second direction, a direction from a portion of the fourth portion toward an other portion of the first conductive member being aligned with the second direction;
- a first magnetic layer provided between the portion of the first portion and the portion of the first conductive member;
- a second magnetic layer provided between the portion of the fourth portion and the other portion of the first conductive member;
- a first nonmagnetic portion provided between the first magnetic layer and the portion of the first portion; and
- a second nonmagnetic portion provided between the second magnetic layer and the portion of the fourth portion.

11. The sensor according to claim 10, further comprising a first interconnect,
at least a portion of the first interconnect being along the third direction.

12. The sensor according to claim 10, comprising a plurality of the first structure bodies,
the first structure bodies being arranged along the third direction,
the first magnetic part of one of the first structure bodies and the second magnetic part of an other one of the first structure bodies being electrically connected to each other.

13. The sensor according to claim 10, further comprising a plurality of second structure bodies,
one of the second structure bodies including a plurality of the first structure bodies,
the first structure bodies being arranged along the third direction,
the first magnetic part of one of the first structure bodies and the second magnetic part of an other one of the first structure bodies being electrically connected to each other,
the second structure bodies being arranged along the first direction,
one of the second structure bodies and an other one of the second structure bodies being electrically connected to each other.

14. The sensor according to claim 13, wherein a distance along the first direction between the first magnetic part of one of the first structure bodies included in the one of the second structure bodies and the first magnetic part of an other one of the first structure bodies included in the other one of the second structure bodies is shorter than at least one of the third length or the fifth length.

15. The sensor according to claim 11, further comprising a current supply circuit configured to supply an alternating current to the first interconnect.

16. The sensor according to claim 15, further comprising a detection circuit configured to detect a value corresponding to an electrical resistance between the first magnetic part and the first magnetic layer.

* * * * *